(12) United States Patent
Yang et al.

(10) Patent No.: US 7,329,638 B2
(45) Date of Patent: Feb. 12, 2008

(54) DRUG DELIVERY COMPOSITIONS

(75) Inventors: Victor C. Yang, Ann Arbor, MI (US);
Yoon Jeong Park, Seoul (KR);
Junfeng Liang, Westfield, NJ (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/835,151

(22) Filed: Apr. 29, 2004

(65) Prior Publication Data
US 2005/0042753 A1     Feb. 24, 2005

Related U.S. Application Data

(60) Provisional application No. 60/466,804, filed on Apr. 30, 2003, provisional application No. 60/466,811, filed on Apr. 30, 2003.

(51) Int. Cl.
*A61K 38/00* (2006.01)
*A61K 39/00* (2006.01)

(52) U.S. Cl. .................. 514/2; 424/185.1; 977/705

(58) Field of Classification Search ............... 435/455; 530/300, 350
See application file for complete search history.

(56) References Cited

U.S. PATENT DOCUMENTS

2003/0219378 A1* 11/2003 Piwnica-Worms ......... 424/1.69
2005/0130167 A1*  6/2005 Bao et al. .................... 435/6

OTHER PUBLICATIONS

Liang, J. et al. Journal of Pharmaceutical Sciences 89(5): 664-673 (2000).*
Lanza, G. et al. Circulation 106: 2842-2847 (2002).*
Lewin, M. et al. Nature Biotechnology 18: 410-414 (2000).*
Falnes et al. Biochemistry 40: 4349-4358 (2001) "Ability of the Tat Basic Domain and VP22 to mediate cell binding, but not membrane translocation of the Diphtheria Toxin-A-Fragment".*
Violini et al. Biochemistry 41: 12652-12661 (2002) "Evidence for a plasma membrane-mediated permeability barrier to Tat Basic Domain in well-differentiated epithelial cells: lack of correlation with Heparan Sulfate".*
Crommelin et al. Journal of Controlled Release 87: 81-88 (2003) "Nanotechnological approaches for the delivery of macromolecules".*
Duvvuri et al. Expert Opin. Biol. Ther. 3(1): 45-56 (2003) "Drug delivery to the retina: challenges and opportunities".*
K. Bosslet et al., Cancer Res., 58:1195-1201 [1998].
R.K. Jain, Int. J. Radiat. Biol., 60:85-100 [1991].
R.K. Jain and L.T. Baxter, Cancer Res., 48:7022-7032 [1998].
K.N. Syrigos and A.A. Epenetos Anticancer Res., 19:605-613 [1999].
J.F. Liang et al., J. Controlled Release, 78:67-79 [2002].
R.V.J. Chari, Adv. Drug Deliv. Rev., 31:89-104 [1998].
D. Putnam and J. Kopecek, Adv. Polymer Sci., 122:55-123 [1995 ].

K.N. Syrigos and A.A. Epenetos, Anticancer Res., 19:606-614 [1999].
K.D. Bagshawe Brit. J. Cancer, 56:531-532 [1987]).
Liang et al., J. Controlled Release, 72:145-156 [2001].
G.J. Russell-Jones and D.H. Alpers, Pharm. Biotechnol., 12:493-520 [1999].
R.B. Greenwald et al., Critical Rev. Therapeutic Drug Carrier Syst., 17:101-161 [2000].
I. Mellman, Annu. Rev. Cell Dev. Biol., 12:575-625 [1996].
U. Niesner et al., Bioconjugate Chem., 13:729-736 [2002].
S. Fawell et al., Proc. Natl. Acad. Sci, USA, 91:664-668 [1994].
P.A. Leland et al., J. Biol. Chem., 276(46):43095-43102 [2001].
C.P. Adams et al., Cancer Res., 58:485-490 [1998].
M. Juweid et al., Cancer Res., 52:5144-5153 [1992]).
R. Chakrabarti et al., J. Biol. Chem., 264(26):15494-15500 [1989].
T. Suzuki et al., J. Biol. Chem. 277:2437-2443 [2002].
B.C. Laguzza et al., J. Med. Chem., 32:548-555 [1989].
A. Trouet, Proc. Natl. Acad. Sci. USA, 79:626-629 [1982].
D. Schneck et al., Clin. Pharmacol. Ther., 47:36-41 [1990].
L.C. Chang et al., AAPS Pharm. Sci., 3(2) Article 17 [2001].
C. Liu et al., Proc. Natl. Acad. Sci. USA, 93:8618-8623 [1996].
H. Maeda et al., J. Controlled Release, 65:271-284 [2000]).
L.C. Chang et al., AAPS Pharm. Sci., 3(2) Article 18 [2001].
J.N. Moreira et al., Biochim Biophys Acta., 515:167-176 [2001].
D.A. Mann and A.D. Frankel, EMBO, J., 10:1733-1739 [1991].
J.D. Cooper et al., Proc. Natl. Acad. Sci. USA, 98:10439-10444 [2001].
E. Vives et al., J. Biol. Chem., 272:16010-16017 [1997].
D. Derossi et al., J. Biol. Chem. 269:10444-10450 [1994].
D. Derossi et al., J. Biol. Chem., 271:18188-18193 [1996].
Schwarze et al., Science, 285:1569-1572 [1999].
L. Josephson et al., Bioconjugate Chem., 10:186-191 [1999].
W.C. Enochs et al., J. Magn. Reson. Imaging, 9:228-232 [1999]).
D. Derossi et al., Trends Cell Bio., 8:84-87 [1998].
S. Futaki et al., Biochemistry, 41:7925-7930 [2002].
M. Wu, Brit. J. Cancer, 75:1347-1355 [1997].
T. Ooya T and N. Yui, Crit. Rev. Ther. Drug Carrier Syst., 16:289-330 [1999].
Z. Mi et al., Molecular Therapy, 2:339-347 [2000].
M. Green and P.M. Loewenstein, Cell, 55:1179-1188 [1988]).
D.J. Mitchell et al., J. Peptide Res., 56:318-325 [2000].
T. Suzuki et al., J. Biol. Chem., 277:2437-2443 [2002]).

* cited by examiner

*Primary Examiner*—Robert Mondesi
*Assistant Examiner*—Anand Desai
(74) *Attorney, Agent, or Firm*—Casimir Jones, S.C.

(57) ABSTRACT

The present invention relates to multicomponent compositions and methods of administering these compositions, which specifically translocate therapeutic molecules (e.g., drugs or prodrugs) across biological membranes thus reducing potential toxic side effects on nontargeted cells and tissues.

18 Claims, 24 Drawing Sheets

Figure 2

SEQ ID NO:1

CDCRGDCFC

SEQ ID NO:2

CNGRCVSGCAGRC

SEQ ID NO:3

GSL

SEQ ID NO: 4

MLSLRGSIRFFKPATATL

SEQ ID NO: 5

PPKKKAKV

SEQ ID NO: 6

YGRKKRRQRRR

Figure 3

SEQ ID NO:7

RQIKIWFQNRRMKWKK

SEQ ID NO:8

KRIHPRLTRSIR

SEQ ID NO:9

PPRLRKRRQLNM

SEQ ID NO:10

RRORRTSKLMKR

Figure 12

SEQ ID NO:11

VSRRRRRGGRRR

Figure 20

YGRKKRRQRRR

SEQ ID NO:12

RQIKIWFQNRRMKWKK

SEQ ID NO:13

KRIHPRLTRSIR

SEQ ID NO:14

PPRLRKRRQLNM

SEQ ID NO:15

RRORRTSKLMKR

SEQ ID NO:16

GRKKRRGRRRGTGC

SEQ ID NO:17

Figure 22

CDCRGDCFC

SEQ ID NO:17

CNGRCVSGCAGRC

SEQ ID NO:18

Gly-Ser-Leu

SEQ ID NO:19

Met-Leu-Ser-Leu-Arg-Gln-Ser-Ile-Arg-Phe-Phe-Lys-Pro-Ala-Thr-Arg-Thr-Leu

SEQ ID NO:20

NH-Pro-Pro-Lys-Lys-Lys-Arg-Lys-Val

SEQ ID NO:21

Figure 23

GRKKRRGRRRGTGC

SEQ ID NO:22

DRUG DELIVERY COMPOSITIONS

The present Applicaton claims priority to U.S. Provisional Application 60/466,804 filed Apr. 30, 2003 and U.S. Provisional Application 60/466,811 filed Apr. 30, 2003, both of which are herein incorporated by reference.

The development of the present invention was funded in part by National Institutes of Health grant Nos.: HL38353 and HL55461. The US Government has certain rights in the invention.

FIELD OF THE INVENTION

The present invention relates to multicomponent compositions and methods of administering these compositions, which specifically translocate therapeutic molecules (e.g., drugs or prodrugs) across biological membranes (e.g. blood brain barrier) thus reducing potential toxic side effects on nontargeted cells and tissues. In certain embodiments, the present invention relates to two component drug delivery compositions comprising a first component for specifically targeting therapeutic agents to cells and tissues of interest and a second component that effectively delivers (e.g., translocates a drug or prodrug carried by the component across a cellular membrane) the agents to targeted cells and tissues. In some embodiments, the present invention relates to drug delivery compositions comprising a nanoparticle (e.g., superparamagnetic iron oxide nanoparticles), a cationic molecule (e.g., a protein transduction domain(s) (hereinafter, "PTD")), and therapeutic agent(s).

BACKGROUND OF THE INVENTION

There have been various attempts to administer therapeutic agents to cancerous and precancerous cells in the hope of promoting their apoptotic removal. Generally, these attempts have had limited success because of inadequacies in the delivery means or the agents themselves. For example, many anticancer agent delivery systems lack sufficient specificity to exclusively target cancer cells. Since most anticancer agents strongly interfere with replication and other cellular functions, nonspecific delivery of these agents to noncancerous cells leads to serious toxic side effects.

In particular, the effective delivery of water-soluble low molecular weight anticancer agents is especially difficult because these agents are rapidly cleared from the subject's bloodstream. Similarly, the effective administration of peptide and nucleic acid anticancer agents is difficult because these agents are subject to proteolytic degradation and/or immunogenicity concerns.

Additionally, many current anticancer agents have difficulty crossing, or are unable to cross, the cellular membrane of cancerous cells. Currently, efficient delivery of therapeutic compounds is best achieved with small (typically less than 1,000 Daltons) hydrophobic molecules. However, low molecular weight cytotoxic drugs often localize more efficiently in normal tissues rather than in tumors (K. Bosslet et al., Cancer Res., 58:1195-1201 [1998]) due to the high interstitial pressure and unfavorable blood flow properties within rapidly growing tumors (R. K. Jain, Int. J. Radiat. Biol., 60:85-100 [1991]; and R. K. Jain and L. T. Baxter, Cancer Res., 48:7022-7032 [1998]). Protein and peptide anticancer agents are especially limited in their ability to enter cancer cells. Moreover, even agents that are capable of entering cancer cells often accumulate in the outer layers of tumor tissues and fail to effectively penetrate to the center of solid tumors thus leaving cancer cells at the tumor core to subsequently reseed the subject with new cancers.

In view of the shortcomings in existing drug delivery systems (e.g., compositions), and anticancer drug delivery systems in particular, what are needed are improved drug delivery systems and methods that provide enhanced target specificity and ability to deliver (e.g., translocate) all types of therapeutic agents (e.g.; including hydrophobic, hydrophilic, small, or macromolecular compounds) that are otherwise incapable of entering target (e.g., cancerous) cells and tissues.

SUMMARY OF THE INVENTION

The present invention relates to multicomponent compositions and methods of administering these compositions, which specifically translocate therapeutic molecules (e.g., drugs or prodrugs) across biological membranes thus reducing potential toxic side effects on nontargeted cells and tissues. In certain embodiments, the present invention relates to two component drug delivery compositions comprising a first component for specifically targeting therapeutic agents to cells and tissues of interest and a second component that effectively delivers (e.g., translocates a drug or prodrug carried by the component across a cellular membrane) the agents to targeted cells and tissues. In some embodiments, the present invention relates to drug delivery compositions comprising a nanoparticle (e.g., superparamagnetic iron oxide nanoparticles), a cationic molecule (e.g., a protein transduction domain(s)), and therapeutic agent(s).

In some embodiments, the present invention provides a composition, comprising, a first targeting component, wherein the first targeting component comprises a molecular recognition element, and an anionic molecule having net negative charge, and; a first drug delivery component, wherein the first drug delivery component comprises, a cationic molecule having a net positive charge, and, at least one therapeutic agent. In some of these embodiments, the positively charged cationic molecule associates with the negatively charged anionic molecule (e.g., electrostatic interaction). In additional embodiments, the cationic molecule comprises a protein transduction domain. While the present invention is not limited to any particular protein transduction domains, preferred embodiments of the present invention comprises TAT peptides, or portions thereof. In some of these embodiments, the TAT proteins comprises SEQ ID NO:6. In other embodiments, the TAT peptides is selected from the from the group of SEQ ID NOs:1-5 and 7-11, however, other sequences are contemplated in further embodiments.

In some compositions, the molecule recognition elements bind to a biological targets (e.g., cells or tissues of interest). Molecular recognition elements contemplated by the present invention include, but are not limited to, antibodies, nucleic acids, peptide signal sequences, and the like.

Biological targets contemplated by the present invention include, but are not limited to, cell surface proteins, cell surface receptors, cell surface polysaccharides, extracellular matrix proteins, intracellular proteins, intracellular nucleic acids, and the like. In some embodiments, the biological target is located on the surface of a diseased cell (e.g., cancerous).

Certain embodiments of the present invention provide drug delivery compositions, wherein the cationic molecule mediates the translocation of the therapeutic agent into targeted cell. In some embodiments, the therapeutic agent comprises a hydrophilic molecule. In other embodiments, the therapeutic agent (e.g., drug molecule) comprises a macromolecule (e.g., a peptide). In some embodiments, the therapeutic agent comprises an anticancer drug. In additional embodiments, the therapeutic agent(s) are attached a cationic molecule (e.g., TAT).

Certain compositions of the present invention also comprise anionic molecules. In some of these embodiments, the anionic molecule comprises heparin.

In certain other embodiments, the drug delivery component of the present invention comprises a multivalent therapeutic agent carrier. In some embodiments the multivalent therapeutic agent carrier comprises polyrotaxane or other like molecule.

The present invention also provides methods for delivering therapeutic agents to target cells, comprising, providing, cells having surface exposed biological targets, a drug delivery composition comprising, a first targeting component, wherein first the targeting component comprises, a molecular recognition element, and an anionic molecule having net negative charge, and; a first drug delivery component, wherein the first drug delivery component comprises, a cationic molecule having a net positive charge, and; at least one therapeutic agent, and administering the drug delivery composition to the cells under conditions such the molecular recognition element binds to the surface exposed biological targets on the cells. In some of these embodiments, the cationic element of the drug delivery composition mediates the translocation of the therapeutic agent into the cells (e.g., diseased cells and cancer cells sin particular). Certain embodiments of the present compositions and methods are used to treat cells and tissues within a subject. A variety of subject types are contemplated for treatment by certain embodiments of the compositions and methods of the present invention. For example, in some embodiments, the subjects are mammals (e.g., humans). In preferred embodiments, the present compositions and methods are optimized to treat humans, however, the present invention is not limited to treating humans. Indeed, the present invention contemplates effective drug delivery compositions and treatment methods for a variety of vertebrate animals including, but not limited to, cows, pigs, sheep, horses, cats, dogs, rodents, birds, fish, and the like.

In some preferred embodiments, the cells and/or tissues being treated are resistant to one or more chemotherapies.

The present invention also provides methods of treating subjects having diseased cells comprising administering to the subject an effective amount of a therapeutic agent using a drug delivery composition, wherein the drug delivery composition comprises: a first targeting component, wherein the first targeting component comprises, a molecular recognition element, and an anionic molecule having net negative charge, and; a first drug delivery component, wherein the first drug delivery component comprises, a cationic. molecule having a net positive charge, and the therapeutic agent; under conditions such that the cationic molecules mediate the translocation of the therapeutic agent into the diseased cells.

In preferred embodiments, the present invention provides drug delivery compositions (e.g., conjugates) that target and deliver (e.g., mediate the translocate of) therapeutic (e.g., anticancer) agents to target cells and tissues (e.g., cancer and tumor cells). In some of these embodiments, administration of the present compositions provides effective methods of treating (e.g., ameliorating) or arresting (e.g., prophylaxis) disease states (e.g., cancer) in a subject. In some embodiments, the drug transported by the present compositions is gelonin. In other embodiments, the drug is doxorubicin. In still other embodiments, the drug is a gossypol or gossypolone compound (and analogues, enantiomers, salts, and bases thereof). Additional embodiments of the present invention provide compositions and methods for targeting and delivering many other therapeutic molecule including, but not limited to: agents that induce apoptosis (e.g., Geranylgeraniol [3,7,11,15-tetramethyl-2,6,10,14-hexadecatraen-1-ol], pro-apoptotic Bcl-2 family proteins including Bax, Bak, Bid, and Bad); polynucleotides (e.g., DNA, RNA, ribozymes, RNAse, siRNAs, etc); polypeptides (e.g., enzymes); photodynamic compounds (e.g., Photofrin (II), ruthenium red compounds [e.g., Ru-diphenyl-phenanthroline and Tris(1-10-phenanthroline)ruthenium(II)chloride], tin ethyl etiopurpurin, protoporphyrin IX, chloroaluminum phthalocyanine, tetra(M-hydroxyphenyl)chlorin)); radiodynamic (i.e., scintillating) compounds (e.g., NaI-125, 2,5-diphenyloxazole (PPO); 2-(4-biphenyl)-6-phenylbenzoxazole; 2,5-bis-(5'-tert-butylbenzoxazoyl-[2'])thiophene; 2-(4-t-butylphenyl)-5-(4-biphenylyl)-1,3,4-oxadiazole; 1,6-diphenyl-1,3,5-hexatriene; trans-p,p'-diphenylstilbene; 2-(1-naphthyl)-5-phenyloxazole; 2-phenyl-5-(4-biphenylyl)-1,3,4-oxadiazole; p-terphenyl; and 1,1,4,4-tetraphenyl-1,3-butadiene); radioactive elements or compounds that emits gamma rays (e.g., $^{111}$In-oxine, $^{59}$Fe, $^{67}$Cu, 1251, $^{99}$Te (Technetium), and $^{14}$Cr); radioactive elements or compounds that emit beta particles (e.g., $^{32}$P, $^{3}$H, $^{35}$S, $^{14}$C,); drugs; biological mimetics; alkaloids; alkylating agents; antitumor antibiotics; antimetabolites; hormones; platinum compounds; monoclonal antibodies conjugated to anticancer drugs, toxins and/or defensins, radionuclides; biological response modifiers (e.g., interferons [e.g., IFN-α, etc], and interleukins [e.g., IL-2]); adoptive immunotherapy agents; hematopoietic growth factors; agents that induce tumor cell differentiation (e.g., all-trans-retinoic acid, etc); gene therapy reagents (e.g., antisense therapy reagents and nucleotides); tumor vaccines; and angiogenesis inhibitors and the like. Those skilled in the art are aware of numerous additional drugs and therapeutic agents suitable for delivery by the compositions of the present invention.

In certain embodiments, the drug delivery compositions comprise antioxidant molecules (e.g., vitamin C) to counteract any oxidizing agents (e.g., radioactive elements) carried by the drug delivery component to prevent oxidation of the composition. Suitable antioxidants or antifade agents include, but are not limited to, ascorbic acid, vitamins C and E, beta-carotene and its derivitives and other dietary antioxidants, phenylalanine, azide, p-phenylenediamine, n-propylgallate, diazabicyclo[2,2,2]octane, and the commercial reagents SLOWFADE and PROLONG (Molecular Probes, Eugene Oreg.).

In preferred embodiments, the anticancer agents carried by the drug delivery component comprise agents that induce or stimulate apoptosis including, but not limited to: kinase inhibitors (e.g., epidermal growth factor receptor kinase inhibitor [EGFR]); vascular growth factor receptor kinase inhibitor [VGFR]; fibroblast growth factor receptor kinase inhibitor [FGFR]; platelet-derived growth factor receptor kinase inhibitor [PGFR]; and Bcr-Ab1 kinase inhibitors such as STI-571, GLEEVEC, and GLIVEC); antisense molecules; antibodies (e.g., HERCEPTIN and RITUXAN); anti-estrogens (e.g., RALOXIFENE and TAMOXIFEN); anti-androgens (e.g., flutamide, bicalutamide, finasteride, aminoglutethamide, ketoconazole, and corticosteroids); cyclooxygenase 2 (COX-2) inhibitors (e.g., Celecoxib, Meloxicam, NS-398); non-steroidal anti-inflammatory drugs (NSAIDs); and chemotherapeutic drugs (e.g., irinotecan [Camptosar], CPT-11, fludarabine [Fludara], dacarbazine [DTIC], dexamethasone, mitoxantrone, Mylotarg, VP-16, cisplatinum, 5-FU, Doxrubicin, Taxotere or taxol); cellular signaling molecules; ceramides and cytokines; and staurosprine and the like.

In some preferred embodiments, various compositions of the present invention provide treatments for a number of conditions including, but not limited to, breast cancer, prostate cancer, lung cancer, lymphomas, skin cancer, pancreatic cancer, colon cancer, melanoma, ovarian cancer, brain cancer, head and neck cancer, liver cancer, bladder cancer, non-small lung cancer, cervical carcinoma, leukemia, neuroblastoma and glioblastoma, and T and B cell mediated autoimmune diseases and the like.

In some preferred embodiments, the drug delivery compositions of the present invention are optimized to target and deliver to cancer cells anticancer drugs/agents including, but not limited to: altretamine; asparaginase; bleomycin; capecitabine; carboplatin; carmustine; BCNU; cladribine; cisplatin; cyclophosphamide; cytarabine; dacarbazine; dactinomycin; actinomycin D; Docetaxel; doxorubicin; imatinib; etoposide; VP-16; fludarabine; fluorouracil; 5-FU; gemcitabine; hydroxyurea; idarubicin; ifosfamide; irinotecan; CPT-11; methotrexate; mitomycin; mitomycin-C; mitotane; mitoxantrone; paclitaxel; topotecan; vinblastine; vincristine; and vinorelbine.

In still other embodiments, the targeted cells or tissues are cancer cells selected from topical cells (e.g., malignant melanoma cells and basal cell carcinomas), ductal cells (e.g., mammary ductal adenocarcinoma cell and bowel cancer cells), and deep tissue cells (e.g., hepatocellular carcinoma cells, CNS primary lymphoma cells, and glioma cells).

In some preferred embodiments, the drug delivery compositions of the present invention are optimized to target and deliver antiretroviral drugs and/or agents to cells that inhibit the growth and replication of the human immunodeficiency virus (HIV). Exemplary drugs and agents in this regard include, but are not limited to: nucleotide analogue reverse transcriptase inhibitors (e.g., tenofovir disoproxil fumarate [DF]); nucleoside analogue reverse transcriptase inhibitors (NRTIs) (e.g., zidovudine, lamivudine, abacavir, zalcitabine, didanosine, stavudine, zidovudine+lamivudine, and abacavir+zidovudine+lamivudine); non-nucleoside reverse transcriptase inhibitors (NNRTIs) (e.g., nevirapine, delavirdine, and efavirenz); protease inhibitors (PIs) (e.g., saquinavir [SQV (HGC)], saquinavir [SQV (SGC)], ritonavir, indinavir, nelfinavir, amprenavir, and lopinavir+ritonavir); and combinations thereof (e.g., highly active anti-retroviral therapy [HAART]).

In still other embodiments, the drug delivery compositions of the present invention are optimized to target and deliver drugs and other therapeutic agents to cells for the treatment of diabetes (e.g., types I and II) or the symptoms that commonly arise from this disease. In this regard, certain embodiments of the present invention target and deliver the following exemplary diabetes treatments: insulin (e.g., rapid acting insulin [e.g., insulin lispro]; short acting insulin [e.g., insulin regular]; intermediate acting [e.g., insulin isophane]; long acting insulin [e.g., insulin zinc extended]; very long acting insulin [e.g., insulin glargine]); sulfonylureas (e.g., first generation sulfonylureas [e.g., acetohexamide, chlorpropamide, tolazamide, and tolbutamide]; second generation sulfonylureas [e.g., glimepiride, gipizide, glyburide]); biguanides (e.g., metformin); sulfonylurea/biguanide combination; α-glucosidase inhibitors (e.g., acarabose, and miglitol); thiazolidinediones (glitazones) (e.g., pioglitazone, rosiglitazone); and meglitinides (e.g., repaglinide, nateglinide).

In other embodiments, the drug delivery compositions of the present invention are optimized to target and deliver to cells drugs and other therapeutic agents for the treatment of psychological health issues including, but not limited to, depression (e.g., minor and depressive illness). Depression is the most common mental health problem in the US. While the exact cause of depression remains unknown, depression is thought to caused by a malfunction of brain neurotransmitters. Antidepressants are often prescribed to treat depressive illnesses. The most common prescribed type of antidepressants are the selective serotonin reuptake inhibitors (SSRIs) (e.g., PROZAC (Fluoxetine hydrochloride), PAXIL (paroxetine hydrocloride), ZOLOFT (sertraline hydrocloride), CELEXA (citalopram HBr), SERZONE (nefazodone), REMERON (mitrazapine), and EFFEXOR (venlafaxine HCl)).

In some embodiments, the biological includes a target epitope. The range of target epitopes is practically unlimited. Indeed, any inter- or intra-biological feature (e.g., glycoprotein) of a cell or tissue is encompassed within the present invention. For example, in some embodiments, target epitopes are selected from cell surface proteins, cell surface receptors, cell surface polysaccharides, extracellular matrix proteins, a viral coat protein, a bacterial cell wall protein, a viral or bacterial polysaccharide, intracellular proteins, and intracellular nucleic acids. In still other embodiments, the drug delivery composition is targeted via a signal peptide to a particular cellular organelle (e.g., mitochondria or the nucleus).

In some embodiments, the drug delivery compositions of the present invention are used to treat (e.g., mediate the translocation of drugs and/or prodrugs into) diseased cells and tissues. In this regard, various diseases are amenable to treatment using the present drug delivery compositions and methods. An exemplary list of diseases includes: breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; neuroblastoma and glioblastoma; T and B cell mediated autoimmune diseases; inflammatory diseases; infections; hyperproliferative diseases; AIDS; degenerative conditions, vascular diseases, and the like. In some embodiments, the treated cancer cells are metastatic.

Still other specific compositions and methods are directed to treating cancer in a subject comprising: administering to a patient having cancer, wherein the cancer is characterized by resistance to cancer therapies (e.g., chemoresistant, radiation resistant, hormone resistant, and the like), an effective amount an anticancer drug or prodrug.

In some embodiments, the present invention provides drug delivery compositions and methods suitable for treating infections or for destroying infectious agents. In this regard, the present invention provides embodiments for treating infections caused by viruses, bacteria, fungi, mycoplasma, and the like. The present invention in not limited, however, to treating any particular infection or to the destruction of any particular infectious agent. For example, in some embodiments, the present invention provides compositions directed to treating (e.g., mediating the translocation of a therapeutic agents) to ameliorate diseases caused by the following exemplary pathogens: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., 0 1 57:H7 and K88), *Ehrlichia chafeensis, Clostridium botulinum, Clostridium perfringens, Clostridium tetani,*

Enterococcusfaecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacterpylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacteriumfortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Ccryptoccus, Cryptosporidum, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other viruses, bacteria, archaea, protozoa, fungi and the like).

Some other embodiments the present invention provides pharmaceutical compositions comprising: a drug delivery composition as described herein; and/or instructions for administering the drug delivery composition to a subject, the subject characterized as having a disease state (e.g., cancer). In some of these embodiments, the subject's cancer is resistant to existing anticancer treatments. In preferred embodiments, the instructions meet US Food and Drug Administrations rules, regulations, and suggestions for the provision of therapeutic compounds.

In some embodiments, the present invention provides drug delivery compositions, comprising a magnetic nanoparticle associated with a positively charged cationic molecule and at least one therapeutic agent. In some of these embodiments, the positively charged cationic molecule of the drug delivery composition comprises at least a portion of a protein transduction domain (e.g., TAT, TAT like peptides, LMWP, and the like).

In some preferred embodiments, the PTD comprises at least a portion of the TAT protein. In some other preferred embodiments, the TAT protein comprises SEQ ID NO:12. In still other embodiments, the TAT protein is encoded by a nucleic acid that encodes for the peptide of SEQ ID NO:12. Alternatively, in other embodiments, the TAT protein comprises SEQ ID NO:17, or is encoded by a nucleic acid that codes for the peptide of SEQ ID NO:17.

In still other embodiments, the positively charged cationic molecule comprises a peptide sequence selected from the group consisting of SEQ ID NOs:13-16. In some of these embodiments, the peptide sequence is encoded by a nucleic acid that encodes for a peptide selected from the group consisting of SEQ ID NOs:13-16.

Other preferred embodiments of the compositions of the present invention comprise a molecular recognition element. The present invention contemplates that the molecule recognition elements interact (e.g., bind) to a biological targets. In some embodiments, the molecular recognition elements comprise at least a portion of an antibody, nucleic acid, or peptide signal sequence, and the like.

Contemplated biological targets include, but are not limited to, cell surface proteins, cell surface receptors, cell surface polysaccharides, extracellular matrix proteins, intracellular proteins and intracellular nucleic acids, and the like.

In particularly preferred embodiments, the biological target is on the surface of a diseased cell (e.g., a diseased neuronal cell). In some of these embodiments, the diseased neuronal cell is afflicted with a neurodegenerative disease (e.g., Parkinson's disease). In other embodiments, the diseased cell comprises a cancer cell.

In preferred embodiments, subjects contemplated for treatment using the compositions and methods of the present invention include, but are not limited to, vertebrate animals. In some embodiments, the vertebrate animal is a mammal. In some additional embodiments, the mammal is a human. The present invention is not limited however, to providing compositions and methods for treating human subjects. Indeed, in other embodiments, the present invention provides compositions and methods for administering therapeutic agents to mammals (e.g., horses, cows, sheep, pigs, goats, dogs, cats, and the like), as well as other vertebrate animals (e.g., birds, fish, and the like).

In some embodiments, the diseased cells (e.g., cancer cells) are resistant to previous administered therapeutic treatments (e.g., chemotherapy, radiotherapy, etc).

In preferred embodiments, the positively charged cationic molecule mediates the translocation of the at least one therapeutic agent into a cell. Suitable therapeutic agents comprise hydrophilic molecules. Other suitable therapeutic agents comprise macromolecules (e.g., peptides). In some of these embodiments, the peptide comprises dopamine. In still other embodiments, the therapeutic agent comprises an anticancer drug.

Other embodiments of the present invention comprise comprises multivalent therapeutic agent carriers (e.g., polyrotaxane and the like).

The present invention also provides methods of delivering therapeutic agents to target cells, comprising: providing: cells; a drug delivery composition comprising a magnetic nanoparticle associated with a positively charged cationic molecule and at least one therapeutic agent; and administering the drug delivery composition to the cells under conditions such the positively charged cationic molecule mediates the translocation of the at least one therapeutic agent across the cell membrane of the cells.

In some embodiments the methods of the present invention are targeted at neuronal cells. In some of these embodiments, the neuronal cells are diseased. Diseases contemplated for treatment by using the compositions and methods of the present invention include neurodegenerative diseases (e.g., Parkinson's disease, HIV related dementia, and the like), cancer (e.g., glioma), and the like.

The cells being treated (administered) the compositions of the present invention are preferably in a subject, however, other cells and tissues are contemplated in in vitro and ex vivo applications. In some embodiments, the subject is a vertebrate animal (e.g., horses, sheep, cows, pigs, goats, dogs, cats, rodents, birds, fish, and the like). In some preferred embodiments, the vertebrate animal is a mammal (e.g., human).

In some embodiments, the cells, tissues, and/or subjects being treated with the compositions and methods of the present invention have failed to respond to previous anticancer therapies.

The present invention also provides methods of treating subjects having diseased cells comprising administering to the subject an effective amount of a therapeutic agent carried by a drug delivery composition, wherein the drug delivery composition comprises a magnetic nanoparticle associated with a positively charged cationic molecule and at least one therapeutic agent.

In preferred embodiments, the present invention provides drug delivery compositions (e.g., conjugates) that target and deliver (e.g., mediate the translocate of) therapeutic (e.g., anticancer) agents to target cells and tissues (e.g., neuronal cells). In some of these embodiments, administration of the present compositions provides effective methods of treating (e.g., ameliorating) or arresting (e.g., prophylaxis) disease states (e.g., Parkinson's disease, Alzheimer's disease, glioma) in a subject. In particularly, preferred embodiments, the present invention provides compositions for targeting and delivering dopamine, peroxidase, and neuronal growth factors (NGFs) to neuronal cells.

In some embodiments, anticancer therapeutic agents, drugs, and prodrugs are transported by the present compositions. Additional embodiments of the present invention provide compositions and methods for targeting and delivering many other therapeutic molecules including, but not limited to: agents that induce apoptosis (e.g., Geranylgeraniol [3,7,11,1 5-tetramethyl-2,6,10,14-hexadecatraen-1-ol], pro-apoptotic Bcl-2 family proteins including Bax, Bak, Bid, and Bad); polynucleotides (e.g., DNA, RNA, ribozymes, RNAse, siRNAs, etc); polypeptides (e.g., enzymes); photodynamic compounds (e.g., Photofrin (II), ruthenium red compounds [e.g., Ru-diphenyl-phenanthroline and Tris(1-10-phenanthroline)ruthenium(II)chloride], tin ethyl etiopurpurin, protoporphyrin IX, chloroaluminum phthalocyanine, tetra(M-hydroxyphenyl)chlorin)); radiodynamic (i.e., scintillating) compounds (e.g., NaI-125, 2,5-diphenyloxazole (PPO); 2-(4-biphenyl)-6-phenylbenzoxazole; 2,5-bis-(5'-tert-butylbenzoxazoyl-[2'])thiophene; 2-(4-t-butylphenyl)-5-(4-biphenylyl)-1,3,4-oxadiazole; 1,6-diphenyl-1,3,5-hexatriene; trans-p,p'-diphenylstilbene; 2-(1-naphthyl)-5-phenyloxazole; 2-phenyl-5-(4-biphenylyl)-1,3,4-oxadiazole; p-terphenyl; and 1,1,4,4-tetraphenyl-1,3-butadiene); radioactive elements or compounds that emits gamma rays (e.g.,$^{111}$In-oxine, $^{59}$Fe, $^{67}$Cu, $^{125}$I, $^{99}$Te (Technetium), and $^{51}$Cr); radioactive elements or compounds that emit beta particles (e.g., $^{32}$P, $^{3}$H, $^{35}$S, $^{14}$C,); drugs; biological mimetics; alkaloids; alkylating agents; antitumor antibiotics; antimetabolites; hormones; platinum compounds; monoclonal antibodies conjugated to anticancer drugs, toxins and/or defensins, radionuclides; biological response modifiers (e.g., interferons [e.g., IFN-α, etc], and interleukins [e.g., IL-2]); adoptive immunotherapy agents; hematopoietic growth factors; agents that induce tumor cell differentiation (e.g., all-trans-retinoic acid, etc); gene therapy reagents (e.g., antisense therapy reagents and nucleotides); tumor vaccines; and angiogenesis inhibitors and the like. Those skilled in the art are aware of numerous additional drugs and therapeutic agents suitable for delivery by the compositions of the present invention.

In certain embodiments, the drug delivery compositions comprise antioxidant molecules (e.g., vitamin C) to counteract any oxidizing agents (e.g., radioactive elements) carried by the drug delivery compositions to prevent oxidation of the composition. Suitable antioxidants or antifade agents include, but are not limited to, ascorbic acid, vitamins C and E, beta-carotene and its derivatives and other dietary antioxidants, phenylalanine, azide, p-phenylenediamine, n-propylgallate, diazabicyclo[2,2,2]octane, and the commercial reagents SLOWFADE and PROLONG (Molecular Probes, Eugene Oreg.).

In preferred embodiments, the anticancer agents carried by the present compositions comprise agents that induce or stimulate apoptosis including, but not limited to: kinase inhibitors (e.g., epidermal growth factor receptor kinase inhibitor [EGFR]); vascular growth factor receptor kinase inhibitor [VGFR]; fibroblast growth factor receptor kinase inhibitor [FGFR]; platelet-derived growth factor receptor kinase inhibitor [PGFR]; and Bcr-Ab1 kinase inhibitors such as STI-571, GLEEVEC, and GLIVEC); antisense molecules; antibodies (e.g., HERCEPTIN and RITUXAN); antiestrogens (e.g., RALOXIFENE and TAMOXIFEN); antiandrogens (e.g., flutamide, bicalutamide, finasteride, aminoglutethamide, ketoconazole, and corticosteroids); cyclooxygenase 2 (COX-2) inhibitors (e.g., Celecoxib, Meloxicam, NS-398); non-steroidal anti-inflammatory drugs (NSAIDs); and chemotherapeutic drugs (e.g., irinotecan [Camptosar], CPT-11, fludarabine [Fludara], dacarbazine [DTIC], dexamethasone, mitoxantrone, Mylotarg, VP-16, cisplatinum, 5-FU, Doxrubicin, Taxotere or taxol); cellular signaling molecules; ceramides and cytokines; and staurosprine and the like.

In some preferred embodiments, various compositions of the present invention provide treatments for a number of conditions including, but not limited to, breast cancer, prostate cancer, lung cancer, lymphomas, skin cancer, pancreatic cancer, colon cancer, melanoma, ovarian cancer, brain cancer, head and neck cancer, liver cancer, bladder cancer, non-small lung cancer, cervical carcinoma, leukemia, neuroblastoma and glioblastoma, and T and B cell mediated autoimmune diseases and the like.

In some preferred embodiments, the drug delivery compositions of the present invention are optimized to target and deliver anticancer drugs/agents including, but not limited to: altretamine; asparaginase; bleomycin; capecitabine; carboplatin; carmustine; BCNU; cladribine; cisplatin; cyclophosphamide; cytarabine; dacarbazine; dactinomycin; actinomycin D; Docetaxel; doxorubicin; imatinib; etoposide; VP-16; fludarabine; fluorouracil; 5-FU; gemcitabine; hydroxyurea; idarubicin; ifosfamide; irinotecan; CPT-11; methotrexate; mitomycin; mitomycin-C; mitotane; mitoxantrone; paclitaxel; topotecan; vinblastine; vincristine; and vinorelbine.

In still other embodiments, the targeted cells or tissues are cancer cells selected from topical cells (e.g., malignant melanoma cells and basal cell carcinomas), ductal cells (e.g., mammary ductal adenocarcinoma cell and bowel cancer cells), and deep tissue cells (e.g., hepatocellular carcinoma cells, CNS primary lymphoma cells, and glioma cells).

In some preferred embodiments, the drug delivery compositions of the present invention are optimized to target and deliver antiretroviral drugs and/or agents to cells that inhibit the growth and replication of the human immunodeficiency virus (HIV). Exemplary drugs and agents in this regard include, but are not limited to: nucleotide analogue reverse transcriptase inhibitors (e.g., tenofovir disoproxil fumarate [DF]); nucleoside analogue reverse transcriptase inhibitors (NRTIs) (e.g., zidovudine, lamivudine, abacavir, zalcitabine, didanosine, stavudine, zidovudine+lamivudine, and abacavir+zidovudine+lamivudine); non-nucleoside reverse transcriptase inhibitors (NNRTIs) (e.g., nevirapine, delavirdine, and efavirenz); protease inhibitors (PIs) (e.g., saquinavir [SQV (HGC)], saquinavir [SQV (SGC)], ritonavir, indinavir, nelfinavir, amprenavir, and lopinavir+ritonavir); and combinations thereof (e.g., highly active anti-retroviral therapy [HAART]).

In still other embodiments, the drug delivery compositions of the present invention are optimized to target and deliver drugs and other therapeutic agents to cells for the treatment of diabetes (e.g., types I and II) or the symptoms that commonly arise from this disease. In this regard, certain embodiments of the present invention target and deliver the following exemplary diabetes treatments: insulin (e.g., rapid acting insulin [e.g., insulin lispro]; short acting insulin [e.g., insulin regular]; intermediate acting [e.g., insulin isophane]; long acting insulin [e.g., insulin zinc extended]; very long acting insulin [e.g., insulin glargine]); sulfonylureas (e.g., first generation sulfonylureas [e.g., acetohexamide, chlorpropamide, tolazamide, and tolbutamide]; second generation sulfonylureas [e.g., glimepiride, gipizide, glyburide]); biguanides (e.g., metformin); sulfonylurea/biguanide combination; α-glucosidase inhibitors (e.g., acarabose, and miglitol); thiazolidinediones (glitazones) (e.g., pioglitazone, rosiglitazone); and meglitinides (e.g., repaglinide, nateglinide).

In other embodiments, the drug delivery compositions of the present invention are optimized to target and deliver to cells drugs and other therapeutic agents for the treatment of psychological health issues including, but not limited to, depression (e.g., minor and depressive illness). Depression is the most common mental health problem in the US. While the exact cause of depression remains unknown, depression is thought to caused by a malfunction of brain neurotransmitters. Antidepressants are often prescribed to treat depressive illnesses. The most common prescribed type of antidepressants are the selective serotonin reuptake inhibitors (SSRIs) (e.g., PROZAC (Fluoxetine hydrochloride), PAXIL (paroxetine hydrochloride), ZOLOFT (sertraline hydrochloride), CELEXA (citalopram HBr), SERZONE (nefazodone), REMERON (mitrazapine), and EFFEXOR (venlafaxine HCl)).

In some embodiments, the biological target includes a target epitope. The range of target epitopes is practically unlimited. Indeed, any inter- or intra-biological feature (e.g., glycoprotein) of a cell or tissue is encompassed within the present invention. For example, in some embodiments, target epitopes are selected from cell surface proteins, cell surface receptors, cell surface polysaccharides, extracellular matrix proteins, a viral coat protein, a bacterial cell wall protein, a viral or bacterial polysaccharide, intracellular proteins, and intracellular nucleic acids. In still other embodiments, the drug delivery composition is targeted via a signal peptide to a particular cellular organelle (e.g., mitochondria or the nucleus).

In some embodiments, the drug delivery compositions of the present invention are used to treat (e.g., mediate the translocation of drugs and/or prodrugs into) diseased cells and tissues. In this regard, various diseases are amenable to treatment using the present drug delivery compositions and methods. An exemplary list of diseases includes: breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; neuroblastoma and glioblastoma; T and B cell mediated autoimmune diseases; inflammatory diseases; infections; hyperproliferative diseases; AIDS; degenerative conditions, vascular diseases, and the like. In some embodiments, the treated cancer cells are metastatic.

Still other specific compositions and methods are directed to treating cancer in a subject comprising: administering to a patient having cancer, wherein the cancer is characterized by resistance to cancer therapies (e.g., chemoresistant, radiation resistant, hormone resistant, and the like), an effective amount an anticancer drug or prodrug.

In some embodiments, the present invention provides drug delivery compositions and methods suitable for treating infections or for destroying infectious agents. In this regard, the present invention provides embodiments for treating infections caused by viruses, bacteria, fungi, mycoplasma, and the like. The present invention in not limited, however, to treating any particular infection or to the destruction of any particular infectious agent. For example, in some embodiments, the present invention provides compositions directed to treating (e.g., mediating the translocation of a therapeutic agents) to ameliorate diseases caused by the following exemplary pathogens: *Bartonella henselae, Borrelia burgdorferi, Campylobacter jejuni, Campylobacterfetus, Chlamydia trachomatis, Chlamydia pneumoniae, Chylamydia psittaci, Simkania negevensis, Escherichia coli* (e.g., 0157:H7 and K88), *Ehrlichia chafeensis, Clostridium botulinum, Clostridium perfringens, Clostridium tetani, Enterococcusfaecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum,* Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Ccryptoccus, Cryptosporidum, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other viruses, bacteria, archaea, protozoa, fungi and the like).

In certain embodiments, the compositions of the present invention are used for simultaneous tumor imaging and drug therapy. Some other embodiments the present invention provide pharmaceutical compositions comprising: a drug delivery composition as described herein; and/or instructions for administering the drug delivery composition to a subject, the subject characterized as having a disease state (e.g., cancer). In some of these embodiments, the subject's cancer is resistant to existing anticancer treatments. In preferred embodiments, the instructions meet US Food and Drug Administrations rules, regulations, and suggestions for the provision of therapeutic compounds.

DESCRIPTION OF THE FIGURES

FIG. 1 further provides a schematic of one contemplated mechanism of specific delivery of a therapeutic agent to a target cell (e.g., a cancer cell).

FIG. 2 provides sequences for SEQ ID NOs: 1, 2, 3, 4, 5, and 6, respectively, as they are used in certain embodiments of the present invention.

FIG. 3 provides sequences for SEQ ID NOs: 7, 8, 9, and 10 respectively,.as they are used in certain embodiments of the present invention.

FIG. 11B shows tumors excised from mice treated with: Lane No. 1: PBS solution (average tumor mass: 3.16±0.65 g; N=5); Lane No. 2: 300 μg of RNase (2.92±0.47 g; N=5); Lane No. 3: 350 μg of TAT-RNase conjugates (equivalent to 300 μg of RNase) (0.18+0.08 g; N=5); Lane No. 4: 350 μg TAT-RNase conjugates+80 μg heparin (2.77±0.63 g; N=5); and Lane No. 5: 350 μg TAT-RNase conjugates+80 μg heparin+240 μg protamine (0.09±0.05 g; N=6). Drugs were administered by intratumoral injection. Injections were started 3 weeks after tumor cell implantation when tumors reached the size about 100 mm³. Thirty days after initial treatment, mice were sacrificed and their tumors were excised, weighed, and photographed.

FIG. 12 provides the sequence for SEQ ID NO: 11, as used in certain embodiments of the present invention.

FIG. 20 provides sequences for SEQ ID NOs: 12, 13, 14, 15, and 16, respectively, as they are used in certain embodiments of the present invention.

FIG. 22 provides sequences for SEQ ID NOs: 17, 18, 19, 20, and 21, respectively, as they are used in certain embodiments of the present invention.

FIG. 23 provides the sequence for SEQ ID NOs: 22 it is used in certain embodiments of the present invention.

DEFINITIONS

Figure 1:
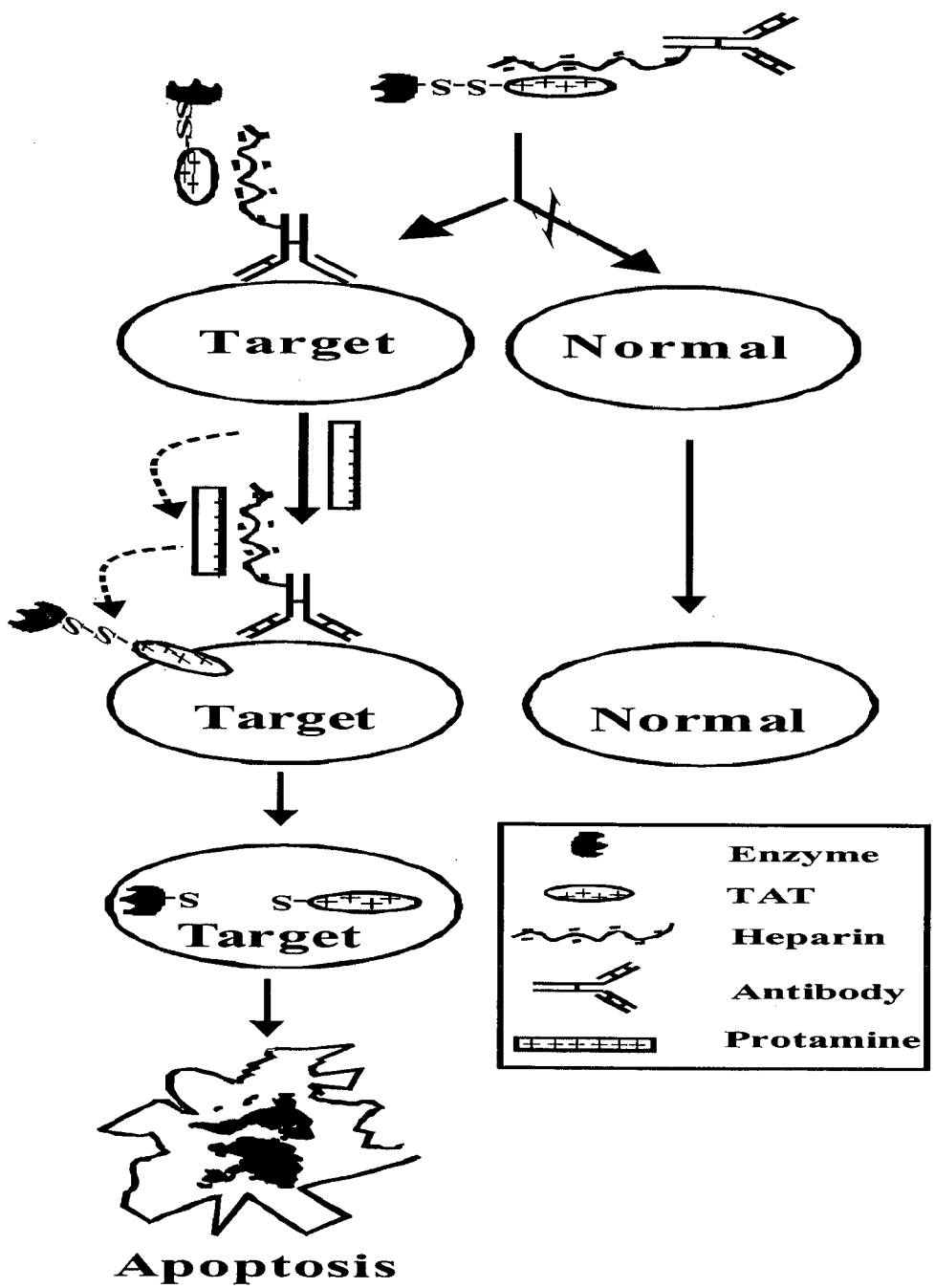
FIG. 1 shows one contemplated embodiment of a two component drug delivery composition, wherein the targeting component comprises a molecular recognition element (e.g., an antibody, or portion thereof) and an anionic element (e.g., heparin molecule), and the drug delivery component comprises a protein transduction domain (PTD) (e.g., TAT) and a conjugated drug molecule (e.g., an enzyme).

To facilitate an understanding of the present invention, a number of terms and phrases are defined below:

As used herein, the term "molecular recognition element" refers to molecules capable of specifically (i.e., non-randomly) binding to, hybridizing to, or otherwise interacting with a desired target molecule. Examples of molecular recognition elements include, but are not limited to, nucleic acid molecules (e.g., RNA and DNA, including ligand-binding RNA molecules), polypeptides (e.g., antigen binding proteins, receptor ligands, signal peptides, hydrophobic membrane spanning domains), antibodies (and portions thereof), organic molecules (e.g., biotin, carbohydrates, glycoproteins), and inorganic molecules (e.g., vitamins). A given drug delivery composition may have affixed thereto one or a variety of molecular recognition elements.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin [BSA], or keyhole limpet hemocyanin [KLH]). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides production of antibody molecules by continuous cell lines in culture may be used. (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

Techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

As used herein the term "antibody" refers to a glycoprotein evoked in an animal by an immunogen (antigen). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., $V_H$ and $V_L$ respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope.

As used herein the term "biological target" refers to any organism, cell, microorganism, bacteria, virus, fungus, plant, prion, protozoa, or pathogen or portion of an organism, cell, microorganism, bacteria, virus, fungus, plant, prion, protozoa or pathogen.

As used herein, the terms "peptide" or "polypeptide" refer to a chain of amino acids (i.e., two or more amino acids) linked through peptide bonds between the α-carboxyl carbon of one amino acid residue and the α-nitrogen of the next. A "peptide" or "polypeptide" may comprise an entire protein or a portion of protein. "Peptides" and "polypeptides" may be produced by a variety of methods including, but not limited to chemical synthesis, translation from a messenger RNA, expression in a host cell, expression in a cell free translation system, and digestion of another polypeptide.

As used herein the term "protein" is used in its broadest sense to refer to all molecules or molecular assemblies containing two or more amino acids. Such molecules include, but are not limited to, proteins, peptides, enzymes, antibodies, receptors, lipoproteins, and glycoproteins.

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules.

As used herein, the terms "nucleic acid" or "nucleic acid molecules" refer to any nucleic acid containing molecule including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Nucleic acid molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "material" and "materials" refer to, in their broadest sense, any composition of matter.

As used herein, the term "pathogen" refers to disease causing organisms, microorganisms, or agents including, but not limited to, viruses, bacteria, parasites (including, but not limited to, organisms within the phyla *Protozoa, Platyhelminthes, Aschelminthes, Acanthocephala*, and *Arthropoda*), fungi, and prions.

The terms "bacteria" and "bacterium" refer to all prokaryotic organisms, including those within all of the phyla in the Kingdom *Procaryotae*. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "virus" refers to infectious agents, which with certain exceptions, are not observable by light microscopy, lack independent metabolism, and are able to replicate only within a host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, the term "macromolecule" refers to any large molecule such as proteins, polysaccharides, nucleic acids, and multiple subunit proteins. Examples of macromolecules include, but are not limited to verotoxin I, verotoxin II, Shiga-toxin, botulinum toxin, snake venoms, insect venoms, alpha-bungarotoxin, and tetrodotoxin).

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "ligands" refers to any ion, molecule, molecular group, or other substance that binds to another entity to form a larger complex. Examples of ligands include, but are not limited to, peptides, carbohydrates, nucleic acids (e.g., DNA and RNA), antibodies, or any molecules that bind to receptors.

As used herein, the terms "head group" and "head group functionality" refer to the molecular groups present at the ends of molecules (e.g., the primary amine group at the end of peptides).

As used herein, the term "linker" or "spacer molecule" refers to material that links one entity to another. In one sense, a molecule or molecular group can be a linker that is covalently attached two or more other molecules (e.g., linking a ligand to a self-assembling monomer).

As used herein, the term "homobifunctional," refers to a linker molecule with two functional groups that both react with the same chemical group (e.g., primary amines, esters or aledehydes).

As used herein, the term "hetrobifunctional," refers to a linker molecule with two functional groups that react with different chemical groups (e.g., primary amines, esters or aledehydes).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$-$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of at least one electron, contributed by each of the atoms.

As used herein, the term "host cell" refers to any eukaryotic cell (e.g., mammalian cells, avian cells, amphibian cells, plant cells, fish cells, and insect cells), whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "genome" refers to the genetic material (e.g., chromosomes) of an organism or a host cell.

As used herein, the term "vector" refers to any genetic element, such as a plasmid, phage, transposon, cosmid, chromosome, retrovirus, virion, etc, which is capable of replication when associated with the proper control elements and which can transfer gene sequences between cells. Thus, the term includes cloning and expression vehicles, as well as viral vectors.

The term "nucleotide sequence of interest" refers to any nucleotide sequence (e.g., RNA or DNA), the manipulation of which may be deemed desirable for any reason (e.g., treat disease, confer improved qualities, etc), by one of ordinary skill in the art. Such nucleotide sequences include, but are not limited to, coding sequences, or portions thereof, of structural genes (e.g., reporter genes, selection marker genes, oncogenes, drug resistance genes, growth factors, etc), and non-coding regulatory sequences that do not encode an mRNA or protein product (e.g., promoter sequence, polyadenylation sequence, termination sequence, enhancer sequence, etc).

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "exogenous gene" refers to a gene that is not naturally present in a host organism or cell, or is artificially introduced into a host organism or cell.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "protein of interest" refers to a protein encoded by a nucleic acid of interest.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain translated from the mRNA. The DNA or RNA sequence thus codes for the amino acid sequence.

As used herein, the term "reporter gene" refers to a gene encoding a protein that may be assayed. Examples of reporter genes include, but are not limited to, luciferase (See, e.g., deWet et al., Mol. Cell. Biol., 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science, 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review See e.g., Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor la gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA, 79:6777 [1982]) and the human cytomegalovirus (Boshart et al., Cell, 41:521 [1985]). In preferred embodiments, inducible retroviral promoters (e.g., the BLV promoter is utilized.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc). In contrast, a "regulatable" promoter is one that is capable of directing a level of transcription of an operably linked nucleic acid sequence in the presence of a stimulus (e.g., heat shock, chemicals, etc), which is different from the level of transcription of the operably linked nucleic acid sequence in the absence of the stimulus.

Regulatory elements may be tissue specific or cell specific. The term "tissue specific" as it applies to a regulatory element refers to a regulatory element that is capable of directing selective expression of a nucleotide sequence of interest to a specific type of tissue (e.g., mammillary gland) in the relative absence of expression of the same nucleotide sequence(s) of interest in a different type of tissue (e.g., liver).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue (e.g., cells infected with retrovirus, and more particularly, cells infected with BLV or HTLV). The term "cell type specific" when applied to a regulatory element also means a regulatory element capable of promoting selective expression of a nucleotide sequence of interest in a region within a single tissue.

The cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

A "subject" is an animal such as vertebrate, preferably a mammal, more preferably a human. Mammals, however, are understood to include, but are not limited to, murines, simians, humans, bovines, cervids, equines, porcines, canines, felines etc).

An "effective amount" is an amount sufficient to effect beneficial or desired results. An effective amount can be administered in one or more administrations. "Coadministration" refers to administration of more than one agent or therapy to a subject. Coadministration may be concurrent or, alternatively, the chemical compounds described herein may be administered in advance of or following the administration of the other agent(s). One skilled in the art can readily determine the appropriate dosage for coadministration. When coadministered with another therapeutic agent, both the agents may be used at lower dosages. Thus, coadministration is especially desirable where the claimed compounds are used to lower the requisite dosage of known toxic agents.

As used herein, the term "toxic agent" refers to a material or mixture of materials which are themselves toxic to a biological system (e.g., pathogen, virus, bacteria, cell, or multicellular organism) or which upon a stimulus (e.g., light, α or β particles) produce an agent (e.g., singlet oxygen or free radical) which is toxic to a biological system. As used herein, the term "toxic" refers to any detrimental or harmful effects on a cell or tissue.

As used herein, the term "drug" refers to a pharmacologically active substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein the term "prodrug" refers to a pharmacologically inactive derivative of a parent drug molecule that requires biotransformation (e.g., either spontaneous or enzymatic) within the organism to release the active drug. Preferred prodrugs are variations or derivatives of the compounds that have groups cleavable under metabolic conditions. For example, prodrugs become pharmaceutically active in vivo when they undergo solvolysis under physiological conditions or undergo enzymatic degradation or other biochemical transformation (e.g., phosphorylation, hydrogenation, dehydrogenation, glycosylation etc). Prodrugs often offer advantages of solubility, tissue compatibility, or delayed release in the mammalian organism. (See e.g., Bundgard, Design of Prodrugs, pp. 7-9, 21-24, Elsevier, Amsterdam [1985]; and Silverman, The Organic Chemistry of Drug Design and Drug Action, pp. 352-401, Academic Press, San Diego, Calif. [1992]). Common prodrugs include acid derivatives such as, esters prepared by reaction of parent acids with a suitable alcohol, amides prepared by reaction of the parent acid compound with an amine, or basic groups reacted to form an acylated base derivative. Moreover, the prodrug derivatives of this invention may be combined with other commonly known pharmacological molecules and reaction schemes to enhance bioavailability.

A "pharmaceutical composition" is intended to include the combination of an active agent with a carrier, inert or active, making the composition suitable for diagnostic or therapeutic use in vivo, in vitro or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, Gennaro A R ed. 20th edition, 2000: Williams & Wilkins P A, USA.

"Pharmaceutically acceptable salt" as used herein, relates to any pharmaceutically acceptable salt (acid or base) of a compound of the present invention which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

As used herein, the term "purified" or "to purify" refers to the removal of undesired components from a sample. As used herein, the term "substantially purified" refers to molecules that are removed from their natural environment, isolated or separated, and are at least 60% free, preferably 75% free, and most preferably 90% or greater free from other components with which they are naturally associated.

As used herein, the term "sample" is used in its broadest sense. In one sense, it is meant to include a specimen or culture obtained from any source, including biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals, and industrial samples. These examples are not to be construed as limiting the sample types applicable to the present invention.

GENERAL DESCRIPTION OF THE INVENTION

Various efficiency issues affect the administration of all drugs—and cancer drugs even more particularly. One issue of particular importance in anticancer drug delivery is ensuring that the anticancer agents (often highly cytotoxic) are only delivered to targeted cells (e.g., cancer cells). For example, many anticancer agents and their corresponding delivery systems lack sufficient specificity to exclusively target cancer cells. Since most anticancer agents potently interfere with cellular replication, the inadvertent delivery of these agents to noncancerous cells will likely cause serious however unintended toxicity issues in the nontargeted cells.

Thus, unintended and often indiscriminate killing of nontarget cells (e.g., actively proliferating but noncancerous) has detracted from the use of many very promising anticancer agents. Nonspecific toxicity issues are a major hurdle to the regulatory approval and ultimate administration of many agents to subjects. Thus, nonspecific drug delivery systems and the resulting unintended toxicity on nontarget cells caused by these systems result in enormous delays and costs in drug development.

Recently, efforts have been made to use various targeting moieties to hopefully overcome nonspecific drug delivery issues. (See e.g., K. N. Syrigos and A. A. Epenetos Anticancer Res., 19:606-614 [1999]; Y. J. Park et al., J. Controlled Release, 78:67-79 [2002]; R.V.J. Chari, Adv. Drug Deliv. Rev., 31:89-104 [1998]; and D. Putnam and J. Kopecek, Adv. Polymer Sci., 122:55-123 [1995]). Notably, lack of cancer cell selectivity can be somewhat circumvented by conjugating agents to targeting moieties such as antibodies or ligand peptides (e.g., RDG for endothelium cells). However, conjugating agents to targeting moieties alone does not negate the potential toxic side effects on nontargeted cells, since the agents are still bioactivity on their way to target cells. To some extent, these concerns have been lessened by advances in creation of targeting moiety-prodrug conjugates that are inactive while traveling to specific targeted tissues. Prodrug are typically converted into bioactive molecules at the target site by some biotransformation (e.g., enzymatic cleavage). Despite advances in this field, the efficiency of many existing targeting moiety-prodrug conjugates is reduced by ineffective delivery (e.g., translocation) of the drug/prodrug to the targeted cells (described more fully infra).

Accordingly, in some preferred embodiments the present invention provides combinations of "targeting" and "prodrug" features in integrated drug delivery compositions, such that a therapeutic pro-agent (e.g., an anticancer prodrug) remains inactive until reaching its target where it is subsequently converted into an active therapeutic molecule. In one of these embodiments, the present invention uses the ADEPT system (See e.g., K. N. Syrigos and A. A. Epenetos, Anticancer Res., 19:606-614 [1999]; and K. D. Bagshawe Brit. J. Cancer, 56:531-532 [1987]) that permits a specific enzymatic conversion of prodrugs to active parent drugs at a target site. The ADEPT system has achieved reasonable success in delivering small chemotherapeutic agents to tumors without drug-induced toxic effects. In yet another embodiment, the present invention uses the ATTEMPTS system (See e.g., Y. J. Park Y J et al., J. Controlled Release, 72:145-156 [2001]; and Y. J. Park et al., J. Controlled Release, 78:67-79 [2002]) that converts proteases (e.g., t-PA) into prodrugs by blocking their catalytic site(s) with an appended macromolecule. The bioactive of the protease is restored at the target site by releasing the macromolecule blockage with the addition of a triggering agent.

However, neither the ADEPT nor ATTEMPTS approaches can mediate or facilitate the translocation of therapeutic agents into target cells alone. The shortcomings of the ADEPT and ATTEMPTS approaches restrict their application, to the delivery of small cytotoxic drugs (e.g., doxorubicin), and circulating enzymes (e.g., asparaginase), respectively. (See, Doxorubicin Hydrochloride. In: AHFS Drug Information, American Hospital Formulary Service, Bethesda, Md., pp. 950-960 [2001]). Thus, preferred embodiments contemplate incorporating these systems with other contemplated components of the present invention (e.g., PTDs).

A second issue in the effective administration of anticancer agents is the rapid clearance of some types of therapeutic agents from the subject's bloodstream. Water-soluble low molecular weight agents (e.g., anticancer agents) are particular susceptible to rapid clearance from the subject's blood stream prior to exerting their therapeutic affects. Similarly, effective administration of peptide and nucleic acid agents (e.g., anticancer agents) is also difficult because these agents are subject to proteolytic degradation and/or immunogenicity concerns.

In natural systems, the rate of clearance and other pharmacokinetic behaviors of small molecules (e.g., drugs) in a subject are regulated by a series of transport proteins. (See e.g., H. T. Nguyen, Clin. Chem. Lab. Anim., (2nd Ed.) pp. 309-335 [1999]; and G. J. Russell-Jones and D. H. Alpers, Pharm. Biotechnol., 12:493-520 [1999]). Thus, the pharmacokinetics of contemplated therapeutic agents should be taken into account in any effective drug regimen. The rate of clearance of an agent in a subject is typically manageable. For instance, attaching (e.g., binding) the agent to a macromolecular carrier normally prolongs its circulation and retention times. Accordingly, some embodiments of the present invention provide biomolecules (e.g., drugs) conjugated with polyethylene glycol (PEG), or similar biopolymers, to prevent degradation of the biomolecule and to improve their retention in the subject's bloodstream. (See e.g., R. B. Greenwald et al., Critical Rev. Therapeutic Drug Carrier Syst., 17:101-161 [2000]). Moreover, the present invention further contemplates that PEG's ability to discourage protein-protein interactions reduces the immunogenicity of many conjugated biomolecule compositions. However, prior to the present invention, pharmacokinetic manipulations of agents alone have been insufficient to improve the cell targeting and internalization (e.g., uptake) of many large and/or hydrophilic agents.

Additionally, a third issue is that many current therapeutic agents (e.g., hydrophilic and macromolecular drugs) are unable (or have great difficulty) to cross target cellular membranes (e.g., cancer cells). Overcoming a potential therapeutic agent's (e.g., peptide and macromolecule anticancer agents) inability to enter target cells is probably the most difficult task in effective drug administration.

Currently, efficient delivery of therapeutic compounds can only be achieved when the molecules are small (typically less than 1,000 Daltons) and hydrophobic. However, low molecular weight cytotoxic drugs often localize more efficiently in normal tissues rather than in tumors (K. Bosslet et al., Cancer Res., 58:1195-1201 [1998]) due to the high interstitial pressure and unfavorable blood flow properties within rapidly growing tumors (R. K. Jain, Int. J. Radiat. Biol., 60:85-100 [1991]; and R. K. Jain and L. T. Baxter, Cancer Res., 48:7022-7032 [1998]). Peptide and nucleic acid anticancer agents are especially limited in their ability to cross the cellular membranes of cancerous target cells. Moreover, even agents that are capable of translocating across cancer cell membranes often accumulate in the outer layers of the cancer tissues and fail to effectively penetrate to the center of solid tumors. However, many agents that successfully enter cancer cells accumulate in outer layers of the tumor and do not effectively penetrate to the center of the tumor leaving cancerous cells at the core of the tumor intact and able to reseed the subject's tissues with new cancerous lesions.

Receptor-mediated endocytosis and phagocytosis are two processes that have been used in to incrementally increasing the uptake of therapeutic agents by targeted cells (e.g., cancer cells). (See e.g., I. Mellman, Annu. Rev. Cell Dev. Biol., 12:575-625 [1996]). Despite being widely used, these processes nevertheless are beset by serious limitations such as low uptake efficiency (U. Niesner et al., Bioconjugate Chem., 13:729-736 [2002]), and the requirement that the agent escape from cellular endosomes-not trivial problems. (S. Fawell et al., Proc. Natl. Acad. Sci, USA, 91:664-668 [1994]).

A wide variety of compositions and methods have been tested for delivering protein and other macromolecules into living cells, including microinjection (See e.g., M. Foldvari and M. Mezei, J. Pharm. Sci., 80:1020-1028, [1991]), scrape loading (See e.g., P. L. McNeil et al., J. Cell Biol., 98:1556-1564 [1984]), electroporation (See e.g., R. Chakrabarti et al., J. Biol. Chem., 26:15494-15500 [1989]), liposomes (See e.g., M. Foldvari et al., J. Pharm. Sci., 80:1020-1028 [1991]), bacterial toxins (See e.g., T. I. Prior et al., Biochemistry, 31:3555-3559 [1992]; and H. Stenmark et al., J. Cell Biol., 113:1025-1032 [1991]), and receptor-mediated endocytosis (See e.g., H. Ishihara et al., Pharm. Res., 7:542-546 [1990]; S. K. Basu, Biochem. Pharmacol., 40:1941-1946 [1990]; G. Y. Wu and C. H. Wu, Biochemistry, 27:887-892 [1988]; and C. P. Leamon and P. S. Low, J. Biol. Chem., 267 (35):24966-24971 [1992]).

Despite the numerous efforts to develop effective drug delivery methods for translocating therapeutic agents (e.g., peptides and macromolecules) across cellular membranes, the existing methods suffer from various limitations such as inefficiency, impracticality, causing appreciable cell death, and resulting in intracellular vesicle uptake without effective cytoplasmic delivery.

The most preferred and widely used method for translocating agents across cellular membranes is receptor-mediated endocytosis. Receptor-mediated endocytosis relies upon the binding of antibodies (or ligands) to antigenic determinants (or receptors) on the surface of targeted cells to deliver conjugated agents. Internalization of the agents occurs via endocytosis. (See e.g., I. Mellman, Annul. Rev. Cell Dev. Biol., 12:575-625 [1996]). Despite some success, methods of receptor-mediated endocytosis for delivery of antitumor agents suffer form several limitations. First, not all antibodies can be endocytosed, thus selection of an appropriate antibody for both targeting and facilitating translocation of the therapeutic agent into target cells or tissues is often difficult. Second, antibodies normally penetrate tumors quite slowly and display good tumor:blood ratios for only limited periods after intravenous administration. (A. M. Wu and P. Y. Yazaki, Q. J. Nuclear Med., 44:268-283 [2000]). Biodistribution studies have shown that crossing the endothelial layer of the tumor blood vessel is such a slow process that it severely limits the absolute tumor uptake of antibody-drug conjugates. (U. Niesner et al., Bioconjugate Chem., 13:729-736 [2002]). Third, the presence of an "antigen barrier" (C. P. Adams et al., Cancer Res., 58:485-490 [1998]; and M. Juweid et al., Cancer Res., 52:5144-5153 [1992]) may sequester the antibodies in pervascular regions, preventing the homogeneous distribution of the drug conjugates within the tumor mass. Fourth, receptor-mediated endocytosis requires the invagination and vasculation of the membrane lipid bilayer to form free cytoplasmic vesicles. (R. Chakrabarti et al., J. Biol. Chem., 26: 15494-15500 [1989]). Importantly, since macromolecular drugs (e.g., and especially proteins) that have entered the endocytotic pathway remain enclosed within lipid based endocytotic vesicles, the drugs do not access the cell's cytoplasm. Thus, the escape from endocytotic vesicles is the rate-limiting step in effective intracellular delivery via receptor-mediated endocytosis.

Only a few existing receptor-mediated endocytosis approaches appear capable of overcoming these limitations. One potentially successful approach is called "TAP" (Tumor-Activated Prodrug) therapy (R. V. J. Chari, Adv. Drug Deliv. Rev., 31:89-104 [1998]). In the TAP approach, small cytotoxic drugs are conjugated to tumor-specific antibodies via either a hydrolysable linkage (e.g., hydrozone or a peptide linker) that are cleavable by lysosomal peptidases. (See e.g., B. C. Laguzza et al., J. Med. Chem., 32:548-555 [1989]; A. Trouet, Proc. Natl. Acad. Sci. USA, 79:626-629 [1982]). In some instances the conjugation of the drugs to macromolecular antibodies renders the drugs inactive while traveling to target cells. Once the conjugate binds to target cell's surface, the conjugated drug is internalized via endocytosis and subsequently released from the carrier by hydrolysis or enzymatic degradation of the linker, restoring its original therapeutic potency. However, clinical trials of these antibody-drug conjugates were disappointing as cancer patients failed to show significant responses following treatment. (See e.g., D. Schneck et al., Clin. Pharmacol. Ther., 47:36-41 [1990]; and D. Schneck et al., Antibody Immunoconjugates and Radiopharm., 2:93-100 [1989]). The art attributed these failures to an inability to achieve high concentrations of therapeutic agent in target cells (e.g., tumor cells) likely due to ineffective of endocytosis-mediated cell entry and low concentration of agent conjugated per antibody (e.g., a maximum conjugate load of up to 8 drug molecules per antibody was obtained). (See, M. Singh et al., Cancer Immonol. Immnother., 32:331-334 [1991]). However, additional studies using therapeutic agents 100- to 1000- times more potent than those previously used (e.g., methyldithio-maytasinoid) achieved some improvement as measurable tumor regression was observed in the tested animals. (C. Liu et al., Proc. Natl. Acad. Sci. USA, 93:8618-8623 [1996]).

Another approach to translocating drugs across target cell membranes, involves conjugating the drug molecules to nanocarriers such as water-soluble polymers. Generally, this approach utilizes the "EPR" (Enhanced Permeation and Retention) effect for passive targeting and accumulation of polymer carriers in solid tumor tissues. (See e.g., H. Maeda et al., J. Controlled Release, 65:271-284 [2000]). During angiogenesis, the nascent capillaries supplying nutrients to the tumor tissues posses large gaps between their vascular endothelial cells relative to healthy tissue types. This renders the tumor's nascent blood vessels permeable to macromolecules (>30 KDa), whereas capillaries in normal vascular tissue typically do not allow molecules to traverse. The macromolecules tend to collect in the interstitial space of tumors because the tumors lack a developed lymphatic drainage system. As these drug carriers accumulate, they can enter tumor cells via pinocytosis; a process that is also accelerated in rapidly growing tumor cells. This phenomenon is known as the EPR effect, and has been documented for a variety of polymers (H. Maeda et al., supra; and L. W.

Seymour, Crit. Rev. Therapeu. Drug Carrier Systems, 9:135-187 [1992]) or other types of carriers such as liposomes (J. N. Moreira et al., Biochim Biophys Acta., 515:167-176 [2001]) as a passive means for targeting therapeutic agents to cancer cells. To further facilitate agent uptake, various types of targeting moieties have been attached to the nanocarriers. (See e.g., J. Kopecek et al., Eur. J. Pharm. Biopharm., 50:61-81 [2000]). Conjugation of PEG to the nanocarriers (e.g., stealth liposomes) may prolong agent circulation times for enhanced accumulation of these agents in target cells. (See e.g., J. N. Moreira et al., supra).

Both the aforementioned antibody- and polymer-based drug delivery systems, albeit showing promise in overcoming some existing drug delivery system limitations, are less than optimal and have serious deficiencies. For example, the scale and architecture of polymer structures is not suitable for delivering macromolecular-sized drugs. As for the antibody-drug conjugate systems, the macromolecular (e.g., enzymes) sized drugs should dissociate from the antibody counterpart once the conjugate enters the cell cytoplasm, or otherwise the activity of the drug could be inhibited by steric hindrance from the antibody. Indeed, homogeneous enzyme immunoassay methods are based on this principle. (See e.g., G. F. Rowley et al., J. Biol. Chem., 250:3759-3766 [1975]).

Moreover, conjugating an antibody with a macromolecular therapeutic agent (e.g., a protein) is difficult without providing multiple antibody-agent linkages. Notably, all of the multiple antibody-macromolecule linkages in these conjugates are unlikely to break by hydrolysis or enzymatic degradation, thus the complete dissociation of the macromolecular agent from its antibody counterpart is highly unlikely.

The most outstanding deficiency of antibody receptor-mediated endocytosis and the nanocarriers approaches, however, lies precisely in their use of the receptor-medicated endocytosis (for immunotoxins) or phagocytosis (for particulates) as the means of translocating therapeutic agents across target cell membranes. As mentioned above, these methods of cellular translocation are limited by low cellular uptake efficiency and difficulties in the agents escaping from the endosomes, respectively.

Preferred embodiments of the present invention provide compositions having very specific targeting ability (e.g., via antibodies) and very efficient cellular translocation of attached species (e.g., via protein transduction domains), yet very low occurrence of side effects (e.g., via reversible inhibition of the protein transduction domain until the conjugates reaches its target).

The present invention provides methods and compositions for targeting drugs and other therapeutic agents (e.g., dopaime) to cells and tissues of interest (e.g., diseased cells). The present invention also provides improved methods and compositions for translocating drugs and other therapeutic agents across cellular membranes. Preferred methods and compositions of the present invention provide highly specific targeting and translocation of drugs and therapeutic agents associated (e.g., conjugated) with the present compositions. In some embodiments, the compositions of the present invention provide specific delivery vehicles optimized to chaperone the movement and entry of therapeutic agents conjugated thereto across the membranes of target cells or tissues (e.g., BBB). In one sense, the compositions of the present invention can be thought of as being delivery vehicles that very specifically and effectively transport their associated cargo (e.g., conjugated therapeutic agents) to targeted delivery sites.

In some of embodiments, the compositions of the present invention comprise one or more functionally distinct components. For example, while the compositions of the present invention are not limited to any particular chemical structures or moieties, preferred embodiments comprise a nanoparticle, preferably magnetic, a cationic molecule such as a protein transduction domain, and one or more associated therapeutic agents.

It is understood that the components of the present compositions may optionally further comprise chemical subcomponents, elements, moieties, and the like. For example, in some embodiments, the compositions additionally comprise polyvalent drug carrier elements (e.g., polytraxane), tracking elements (e.g., fluorescent molecules, radioactive molecules, magnetic particles, etc), selection or purification elements (e.g., ligands, antibodies, and the like), antimicrobial agents (e.g., antibiotics, toxins, defensins, antiviral agents etc), chemical protecting groups, signal sequence elements (e.g., nuclear localization signal 'NLS"), molecular recognition elements, and anionic molecules and the like.

In other preferred embodiments, the compositions comprise a molecular recognition element (e.g., an antibody, peptide, protein ligand, polysaccharide, etc) that specifically interacts (e.g., binds) with a moiety (e.g., a biological target) on a cell or tissue of interest.

Similarly, in other preferred embodiments, the drug delivery compositions comprises an agent that readily crosses cellular membranes (e.g., a protein transduction domain "PTD"). In some of these embodiments, the PTD comprises a portion of the human immunodeficiency virus (HIV) transduction domain protein called TAT. In other embodiments, the PTD is electrically charged (e.g., cationic) molecule that interacts with a molecule of opposite charge (e.g., an anionic molecule such as heparin).

In certain compositions comprising at least a portion of a heparin protein (a strongly anionic protein), and a PTD (e.g., TAT, a strongly cationic protein), the opposite electrostatic charges associated with the heparin and the PTD inhibits the potent but indiscriminate cellular translocating abilities of the PTD until the user removes the inhibition. Preferably, in those embodiments that comprise strong electrically dissimilar subcomponents, the electrostatic interactions between subcomponents is overcome by the subsequent administration of an additional compound with greater affinity for one first charged subcomponents. The present invention is not limited however, to providing drug delivery compositions comprising electrically charged subcomponents. Indeed, in some embodiments, the charge on the cationic molecule in relation to the anionic molecule is irrelevant, only the sum affinity of the subsequently administered compound for the anionic element is relevant. Indeed, the principle requirement of the subsequently administered compound is that it posses greater binding affinity for the anionic element than the does the cationic element.

The selection of possible components/subcomponent/elements for a particular application is influenced by a number of factors such as, the intended target cells or tissues, biochemical considerations, the pharmacological profile of therapeutic agent(s) (e.g., drugs) being carried and delivered (e.g., efficacy, side affects, rate of clearance, bioaccumulation, biodistribution, potential interactions and the like), the subject's health, the method of administration (e.g., intravenous, oral, transdermal, etc), and various other factors known to those skilled in the biochemical, medical, and pharmaceutical arts.

In some embodiments, any linkage between the PTD and the therapeutic agent is a hydrolysable (e.g., an ester bond) or enzyme-degradable (e.g., disulfide) bond/linkage. In other embodiments directed to delivering enzymes (and other macromolecules) as therapeutic agents, stable non-/covalent bonds between the PTD and the therapeutic agents are preferred. In some particularly preferred embodiments, the components and/or subcomponents of the present compositions are held together via electrostatic interactions between oppositely charged molecules.

In some embodiments, following administration of drug delivery compositions comprising a PTD and an anionic molecule, an agent (e.g., a disrupting agent) is subsequently administered under conditions such that it disrupts the interaction between the PTD and the anionic molecule. In some of these embodiments, the additional agent comprises a strong heparin antidote (e.g., protamine sulfate). Protamine sulfate is used since this molecule binds to heparin more strongly than TAT does. In preferred embodiments, the administration of an agent that disrupts the electrostatic interaction between components/subcomponents (e.g., the electrostatic binding in PTD-heparin conjugate) triggers the release of composition components. In other embodiments, the disrupting agent is endogenous to the target cell or tissue (e.g., a membrane lipase that cleaves a lipid linker molecule).

In preferred embodiments, the present drug delivery compositions very specifically delivery therapeutic agents that initiate biological affects (e.g., apoptosis) in target cells while sparing nontarget cells from potentially harmful drug interactions and drug-induced effects.

In some other embodiments of the present invention, the drug delivery compositions further comprises an agent or molecule that increases the bioavailability and/or effectiveness (e.g., uptake, cellular retention, potency, etc) of the therapeutic agents being carried.

The present drug delivery systems, compromising PTDs (e.g., TAT, polyarginine peptides, LMWP, etc) effectively translocate therapeutic agents and drugs having many different physical and chemical attributes (e.g., small, large, hydrophilic, hydrophobic, etc) across target cell membranes. In particular, the present invention provides effective compositions and methods for delivering large protein drugs and therapeutic molecules to target cells.

Moreover, membrane transduction mediated by PTDs such as TAT and TAT-like peptides have been shown to occur in a receptor- and transporter-independent fashion that appears to target lipid bilayers directly. (See e.g., A. D. Frankel and C. O. Pabo, Cell, 55:1189-1193 [1988]; S. R. Schwartz et al., Science, 285:1569-1572 [1999]; and T. Suzuki et al., J. Biol. Chem., 277:2437-2443 [2002]).

One advantage of the compositions of the present invention is their ability to specifically target and deliver (e.g., translocate) a wide range of therapeutic molecules (e.g., drugs) to target cells and tissues. Prior to the present invention, biotechnology and pharmaceutical researches were -forced to abandon many compounds showing promising in vitro biological effects, but having restricted in vivo bioavailability. Accordingly, certain embodiments of the present invention provide compositions and methods tailored to effectively deliver agents previously thought to be impractical or unsuited for therapeutic administration due to their unacceptably low water solubility, poor cellular uptake, and/or potent toxic side effects. For example, in one embodiment, the present invention provides compositions that effectively deliver RNase to target cells. Thus, the impact and value of the present drug delivery compositions to the medical and pharmaceutical communities is significant, far-reaching, and widespread. Another advantage of the compositions of the present invention is their ability to overcome multiple drug resistance (MDR) problems encountered by most existing anticancer drugs. The membrane-transducing abilities of PTDs (e.g., TAT, TAT-like peptides, LMWPs, etc) are able to offset the efflux drug-pumping activity of a P-glycoprotein that play an important role in developing MDR.

In additional preferred embodiments, the various elements of the present compositions are associated (e.g., held together) via one or more chemical bonds (e.g., ionic, covalent, electrostatic, hydrogen, disulfide, peptide etc).

DETAILED DESCRIPTION OF THE INVENTION

The present invention provides improved methods and compositions for targeting drugs and other therapeutic agents (e.g., anticancer agents) to cells and tissues of interest (e.g., diseased cells such as tumor cells). The present invention also provides improved methods and compositions for translocating drugs and other therapeutic agents across cellular membranes. Preferred methods and compositions of the present invention provide highly specific targeting and translocation of drugs and therapeutic agents associated (e.g., conjugated) with the present compositions. In some embodiments, the compositions of the present invention provide specific delivery vehicles optimized to chaperone the movement and entry of therapeutic agents conjugated thereto across the membranes of target cells or tissues. In one sense, the compositions of the present invention can be thought of as being delivery vehicles that very specifically and effectively transport their associated cargo (e.g., conjugated therapeutic agents) to delivery sites.

In some of embodiments, the compositions of the present invention comprise one or more, and preferably two distinct (e.g., functionally distinct) major components. For example, while the compositions of the present invention are not limited to any particular chemical structures or moieties, preferred embodiments comprise at least one major targeting component and at least one major drug delivery component. It is understood that the major components of the present compositions further comprise chemical subcomponents, elements, moieties, and the like. For example, in some embodiments, the drug delivery component and/or the targeting component additionally comprise polyvalent drug carrier elements (e.g., polytraxane), tracking elements (e.g., fluorescent molecules, radioactive molecules, magnetic particles, etc), selection or purification elements (e.g., ligands, antibodies, and the like), antimicrobial agents (e.g., antibiotics, toxins, defensins, antiviral agents etc), chemical protecting groups, signal sequence elements (e.g., nuclear localization signal 'NLS") etc.

In other preferred embodiments, the targeting component comprises a molecular recognition element (e.g., an antibody, peptide, protein ligand, polysaccharide, etc) that specifically interacts (e.g., binds) with a corresponding moiety (e.g., a biological target) on a cell or tissue of interest and optionally a strong electrically charged (e.g., cationic or anionic) molecule (e.g., heparin). In some of these embodiments, the electrically charged molecule is strongly anionic.

Similarly, in other preferred embodiments, the drug delivery component comprises an agent that readily crosses cellular membranes (e.g., a protein transduction domain "PTD") and optionally one or more therapeutic agents of interest conjugated thereto. In some of these embodiments, the PTD comprises a portion of the human immunodeficiency virus (HIV) transduction domain protein called TAT.

In certain compositions comprising a molecular recognition element, at least a portion of a heparin protein (a strongly anionic protein), and a drug delivery component that comprises at least a portion of a TAT (a strongly cationic protein) peptide, the opposite electrostatic charges associated with the heparin and the TAT proteins inhibits the potent but indiscriminate cellular translocating abilities of TAT until the user removes the inhibition. Preferably, in those embodiments that cpomprise strong electrically dissimilar subcomponents, the electrostatic interactions between the subcomponents is overcome by the subsequent administration of an additional compound with greater affinity for one first charged subcomponents. The present invention is not limited however, to providing targeting or drug delivery components comprising electrically charged subcomponents.

The selection of possible components/subcomponent/elements for a particular application is influenced by a number of factors such as, the intended target cells or tissues, biochemical considerations, the pharmacological profile of therapeutic agent(s) (e.g., drugs) being carried and delivered (e.g., efficacy, side affects, rate of clearance, bioaccumulation, biodistribution, potential interactions and the like), the subject's health, the method of administration (e.g., intravenous, oral, transdermal, etc), and various other factors known to those skilled in the biochemical, medical, and pharmaceutical arts.

In particularly preferred embodiments, the drug delivery compositions of the present invention comprise a complex made of two components: a targeting component and a drug delivery component. Preferably, the targeting compartment comprises a specific molecular recognition element such as an antibody (Ab), a peptide, or a protein ligand coupled with a heparin (Hep) molecule. The drug delivery compartment preferably comprises a therapeutic agent (e.g., an anticancer drug) linked (e.g., covalently) linked (e.g., conjugated) to a PTD peptide such as TAT, the poly(arginine) peptides (T. Suzuki et al., J. Biol. Chem. 277:2437-2443 [2002]), or an arginine-rich LMWP (L.C. Chang et al., AAPS Pharm. Sci., 3(2) Article 17 [2001]). Other components are also contemplated.

In some embodiments, the linkage between the PTD and the therapeutic agent is a hydrolysable (e.g., an ester bond) or enzyme-degradable (e.g., disulfide) bond/linkage, and/or covalent/non-covalent. In other embodiments directed to delivering enzymes (and other macromolecules) as therapeutic agents, stable covalent bonds between the PTD and the therapeutic agents being carried are preferred. In some particularly preferred embodiments, the components and/or subcomponents of the present compositions are held together via electrostatic interactions between oppositely charged molecules (e.g., a positively charged TAT molecule on the drug component and the negatively charged heparin molecule on the targeting component). The present invention contemplates that the electrostatic interaction between heparin and TAT in various compositions provides an element that is unique the present invention that provides important advantages over existing TAT conjugates: 1) the electrostatic (non-covalent) interaction of heparin and TAT prohibit the TAT-linked complex from indiscriminately translocating across nontarget cell membranes; 2) the charge neutralization protects TAT from proteolytic degradation by circulating enzymes (e.g., trypsin and trypsin like enzymes); and 3) the capabilities of the molecular recognition element (e.g., antibody) are maintained since the potent cell-internalization function of TAT is (reversibly) blocked.

In some embodiments, following administration of drug delivery compositions comprising TAT and heparin components (subcomponents), an agent is subsequently administered under conditions such that it disrupts the interaction between TAT and heparin. In some of these embodiments, the additional agent comprises a strong heparin antidote (e.g., protamine sulfate). Protamine sulfate is used since this molecule binds to heparin more strongly than TAT does. In preferred embodiments, the administration of an agent that disrupts ("disrupting agent") the electrostatic interaction between components/subcomponents (e.g., the electrostatic binding in TAT-heparin conjugate) acts to trigger the release of composition components (e.g., protamine sulfate acts triggers the dissociation of TAT/Drug component from its Ab/Hep component). It is further contemplated, that once the components/subcomponents are detached (e.g., dissociation of TAT/Drug component from its Ab/Hep component), the strong cationic property of the PTD (e.g., TAT) mediates the adsorption of the PTD based drug delivery component across the target cell's membrane. Restoration of TAT's membrane translocating activity following cessation of heparin inhibition enables the drug delivery component to enter the cytosol of the targeted cell. Once inside the cell's parenchyma, the drug molecules are released (e.g., in the case of small molecule drugs) or they remain conjugated to the PTD (e.g., in the case of enzyme and macromolecular drugs). Alternatively, in still other embodiments, the disrupting agent comes from the cell or the local environment (e.g., a lipid linker cleaved by a lipase in the cell membrane).

The present invention further contemplates that use of triggering agent reduces that amount of the drug delivery composition swept away from target cells by the subject's blood flow. In preferred embodiments, the present drug delivery compositions very specifically delivery therapeutic agents and drugs that initiate biological affects (e.g., apoptosis) in target cells while sparing nontarget cells from potentially harmful drug interactions and drug-induced effects. FIG. 1 shows one contemplated embodiment of the present invention.

In some embodiments of the present invention, the PTD of the drug delivery component comprises a low molecule weight protein (LMWP). The present invention contemplates that drug delivery systems having LMWP components/subcomponents remain in the cytosol following cellular entry thus increase drug retention and bioavailability. The present invention further contemplates that LMWP based drug delivery systems efficiently translocate across multiple cellular membranes thus shuttling their conjugated therapeutic cargo deeper into the center of targeted tissues (e.g., tumor core) than is possible with existing drug delivery systems. For example, a major obstacle to antitumor immunotoxin therapy is that upon entering the tumor mass the antibodies become absorbed in the perivascular regions of the initial tumor cells encountered. This limitation on antitumor immunotoxin prevents the antibodies from reaching more central tumor regions. (R. K. Jain and L. T. Baxter, Cancer Res., 48:7022-7032 [1998]; and M. Juweid et al., Cancer Res. 52:5144-5153 [1992]).

In other preferred embodiments, the drug delivery component further comprises a subcomponent (e.g., polymers [such as rotaxanes or polyrotaxane] and other biomolecules) that aid the transport and/or release of the therapeutic agents being carried. In some of these embodiments, the subcomponent increases the number of therapeutic molecules carried that can be carried by a single drug delivery conjugate.

For example, in some of these embodiments, the drug delivery component comprises a polyrotaxane subcomponent. In particular, some embodiments of the present invention provide PTD-polyrotaxane (PR) conjugates that provide significant advantages over existing antibody- or polymer-based drug delivery systems. Indeed, preferred TAT-polyrotaxane conjugates provide the advantages of polymer-based systems in delivering small drugs (e.g., high drug loading and EPR effects, See e.g., H. Maeda et al., J. Controlled Release, 65:271-284 [2000]), while retaining the active targeting and highly efficient drug translocation of PTD based drug delivery systems. These embodiments contrast favorably with the passive cell targeting and slow drug uptake seen in existing particulate-based drug delivery systems.

In certain embodiments of the present invention, the hydrophilic nature of the PTD and polyrotaxane molecules causes hydrophobic drugs to be more soluble and bioavailable, further the universal cell translocating abilities of PTDs makes even normally membrane-impermeable hydrophilic drugs available for therapeutic administration. Additionally, the polymeric architecture of the PTD-polyrotaxane based drug delivery compositions provides great flexibility for further design of drug delivery compositions, including, but not limited to, systems that incorporation PEG to retard drug clearance and immunological responses.

In some other embodiments of the present invention, the drug delivery component further comprises an element/subcomponent that increases the bioavailability or effectiveness (e.g., uptake, cellular retention, potency, etc) of the therapeutic agents after ether the target cell.

The present drug delivery systems, compromising PTDs (e.g., TAT, polyarginine peptides, LMWP, etc) effectively translocate therapeutic agents and drugs having many different physical and chemical attributes (e.g., small, large, hydrophilic, hydrophobic, etc) across target cell membranes. In particular, the present invention provides effective compositions and methods for delivering large protein drugs and therapeutic molecules to target cells.

Moreover, membrane transduction mediated by PTDs such as TAT and TAT-like peptides have been shown to occur in a receptor- and transporter-independent fashion that appears to target lipid bilayers directly. (See e.g., A. D. Frankel and C. O. Pabo, Cell, 55:1189-1193 [1988]; S. R. Schwartz et al., Science, 285:1569-1572 [1999]; and T. Suzuki et al., J. Biol. Chem., 277:2437-2443 [2002]).

One advantage of the compositions of the present invention is their ability to specifically target and deliver (e.g., translocate) a wide range of therapeutic molecules (e.g., drugs) to target cells and tissues. Prior to the present invention, biotechnology and pharmaceutical researches were forced to abandon many compounds showing promising in vitro biological effects, but having restricted in vivo bioavailability. Accordingly, certain embodiments of the present invention provide compositions and methods tailored to effectively deliver agents previously thought to be impractical or unsuited for therapeutic administration due to their unacceptably low water solubility, poor cellular uptake, and/or potent toxic side effects. For example, in one embodiment, the present invention provides compositions that effectively deliver RNase to target cells. Thus, the impact and value of the present drug delivery compositions to the medical and pharmaceutical communities is significant, far-reaching, and widespread.

Another advantage of the compositions of the present invention is their ability to overcome multiple drug resistance (MDR) problems encountered by most existing anti-cancer drugs. The membrane-transducing abilities of PTDs (e.g., TAT, TAT-like peptides, LMWPs, etc) are able to offset the efflux drug-pumping activity of a P-glycoprotein that play an important role in developing MDR.

In additional preferred embodiments, the various components and/or subcomponents of the present compositions are associated (e.g., held together) via one or more chemical bonds (e.g., ionic, covalent, electrostatic, hydrogen, disulfide, peptide etc). In some embodiments, the various components (e.g., targeting component and drug delivery component) further comprise one or more similar or dissimilar chemical compounds, elements, and moieties.

Of all types of brain diseases, neurodegenerative disorders (e.g., Parkinson's disease, Alzheimer's disease, AIDS-related dementia, genetic neurodegenerative disorders: sphingolipidoses (including, Niemann-Pick disease, Gaucher disease, Krabbe disease (globoid cell leukodystrophy), metachromatic leukodystrophy (MLD), GM1 gangliosidosis, and GM2 gangliosidosis), neuronal ceroid lipofuscinoses (including, iHaltia-Santavuori, Jansky-Bielschowsky, and Spielmeyer-Vogt types), adrenoleukodystrophy (classic, neonatal, and adrenomyeloneuropathy), sialidosis (including, types I and II), Huntington disease (HD), spinocerebellar ataxia 1 (SCA 1), Machado-Joseph disease (MJD/SCA 3), Kennedy disease/spinal and bulbar muscular atrophy (SBMA), and dentatorubraopallidoluysian atrophy (DRPLA), and the like, are probably the most difficult pathologies for pharmacological intervention, because conventional receptor-mediated endocytosis is ineffective at delivering drugs to non-dividing cells such as neurons. (M. Lewin et al., Nature Biotechnol., 18:410-414 [2000]).

Parkinson disease (PD) is one of the most widespread neurodegenerative disorders of elderly, and it affects more than one million Americans. Parkinson's disease is characterized by progressive loss of dopaminergic neurons from structures of the basal ganglia resulting in abnormalities in the control of movement. Without treatment, those afflicted with PD progress over 5-10 years to a rigid akinetic state in which they are incapable of caring themselves.

Excitotoxicity and oxidative stress are two mechanisms that appear to be involved in the neuronal death seen in PD patients with the latter being a more likely candidate as a cause of PD. (See e.g., D. G. Standaert and A. B. Young: Treatment of central nervous system degenerative disorders. In: Goodman & Gilman's The Pharmacological Basis of Therapeutics [J. G. Harden and L. E. Limbird eds.], 9th ed., pp. 503-519, McGraw-Hill, New York [1995]; Neurodegenerative disorders. In: Pharmacology [H. P. Rang et al., eds.], pp. 519-531, Churchill Livingston, New York [1995] and Dopamine Hydrochloride. In: AHFS Drug Information 2002,pp. 2383-2386, American Society of Health-System Pharmacists, Bethesda, Md., [2002]).

The term of excitotoxicity has long been used to describe the neuronal injury that results from the presence of excessive glutamate in the brain. (J. W. Olney, Science, 164:719-721 [1969]). Although glutamate is used as a neurotransmitter by many different neuronal systems, it is believed to mediate most excitatory synaptic transmissions in the mammalian brain. The destructive effects of glutamate on brain neurons are mediated by its receptors such as the N-methyl-D-aspartate (NMDA) type and/or the non-NMDA type ionotropic receptors. Binding and activation of the NMDA receptor-channels by glutamate allows an excess influx of $Ca^{+2}$, which is thought to cause cell death in one or more ways of several possible ways including activation of intracellular proteases and lipases, and generation of free radicals.

In some embodiments, the present compositions target and deliver NMDA-receptor antagonists, calcium channel blocking agents, and agents that inhibit calcium-activated proteases to target cells (e.g., neurons) as possible therapies to alleviate excitotoxicity.

Although neurons depend on oxidative metabolism for energy and survival, a consequence of this process is the production of reactive compounds such as hydrogen peroxide ($H_2O_2$) and hydroxyl free radicals (OH). (G. Cohen and P. Werner: Free radicals, oxidative stress and neurodegeneration. In: Neurodegenerative Diseases [D. B. Calne ed.], pp. 139-161, W. B. Saunders, Philadelphia [1994]). Unchecked, these reactive OH species can cause DNA damage, oxidation of membrane lipids, and neuronal death. (J. S. Brains and C. A. Shaw, Brain Res. Rev., 25:335-358 [1997]). Oxidative stress is the result of excessive production of reactive species and impairment of mitochondrial functions. The role for oxidative stress and mitochondrial dysfunction in PD has been supported by several clinical and preclinical studies. (See e.g., A. H. V. Schapira et al., J. Neurochem., 54:823-827 [1990]; and P. J. Blanchet et al., Exp. Neurol., 153:214-222 [1998]). Indeed, for PD patients treated with levodopa, dopamine formed in the brain can be converted by monoamide oxidase (MAO) to release 3,4-dihydroxypenenylacetic acid (DOPAC) and $H_2O_2$, causing enhanced OH generation. Therapeutic interventions based on the oxidative stress concept are theoretically possible but remain unproven, including the use of catalase or peroxidase to prevent the formation of OH as well as free radical scavengers or antioxidants such as superoxide dismutase, ascorbic acid, and vitamin E.

Among the most commonly used pharmacological treatments for PD, the single most effective agent is levodopa (L-3,4-dihydroxy-phenylalanine), the metabolic precursor of dopamine. The therapeutic effects of levodopa result from its transport in the brain and subsequent conversion into dopamine. Importantly, dopamine itself cannot be given orally or via parenteral routes, because it is unable to cross the BBB. When administered orally, levodopa is rapidly absorbed by the small intestine by an active transport system for aromatic amino acids. Levodopa also crosses the BBB and enters by an active transport process mediated by carriers of aromatic amino acids. Inside the brain, levodopa is converted to dopamine by decarboxylation via the action of the aromatic L-amino acid decarboxylase (AAD), which is highly expressed in dopaminergic neurons. The dopamine thus produced is then responsible for all the therapeutic effectiveness of levodopa.

However, about 95% of orally administered levodopa is decarboxylated to form dopamine by peripheral AAD in the intestinal mucosal. (See, Dopamine Hydrochloride. In: AHFS Drug Information 2002, pp. 2383-2386, American Society of Health-System Pharmacists, Bethesda, MD [2002]). Therefore, in clinical practice levodopa is often administered in combination with carbidopa, a peripherally acting AAD inhibitor. The concentration of levodopa increases with the coadministration of carbidopa and levodopa. Despite the benefits of coadministering levodopa and carbidopa, most orally administered levodopa is absorbed by the pancreas, liver, gastrointestinal track, salivary glands, and kidney prior to being transported to the CNS. In fact, it is estimated that less than 1% of orally administered levodopa penetrates the CNS due to the ineffectiveness of its transport system and its rapid metabolism, and even a smaller fraction thereof enters the brain.

Unfortunately, the anti-Parkinson effect of levodopa is demonstrated to depend solely on the formation of dopamine "within" the brain; because the anti-PD effect of levodopa is prevented by AAD (the levodopa-converting enzyme) inhibitors that are capable of entering the brain but not by those, such as carbidopa, that cannot.

The gross inefficiency of oral levodopa therapy necessitates the use of very large doses of levodopa when treating PD. Over administration of levodopa however, predictably leads to systemic toxicity issues via the action of peripheral AAD, causing undesirable adverse reactions such as nausea, anorexia, orthostatic hypotension, cardiac arrhythmias and psychological effects.

Another limitation on administering levodopa is the occurrence of the "on/off response" to drug treatment seen in late stage PD, where the patient's brain losses its ability to convert levodopa to dopamine. (M. M. Mouradian and T. N. Chase: Improve dopaminergic therapy of Parkinson's disease. In: Movement Disorders [C. D. Marsden and S. Fahn eds.], pp. 181-199, Butterworth, Oxford [1994]). In late PD, patients often fluctuate rapidly in the effectiveness of their drug treatments, from being "off" where hypokinesia and rigidity may suddenly worsen for a few hours with no beneficial effects from medications to being "on" again but with the development of dyskinesias and excessive abnormal in-voluntary movements. While the present invention is not limited to any particular mechanism, the present invention contemplates that the "on/off response" results from the loss of endogenous amino acid decarboxylase (AAD) due to the advanced degeneration of dopaminergic neurons in the late stages of PD. Amino acid decarboxylase is responsible for converting levodopa to dopamine. As a result, there is a fluctuation of dopamine concentrations in the brain following levodopa treatment, due to an ineffective and inconsistent levodopa conversion in the brain by the remnant AAD. This hypothesis is favored by clinical observations that as PD progresses, the effectiveness of levodopa treatments gradually decline and become less consistent.

Other PD therapies involve the administration of peroxidase to the brain to act as a free radical and peroxidase scavenger thus protecting neuronal tissues from further degradation.

In preferred embodiments, the present invention provides magnetic nanoparticles associated with PTDs and therapeutic agents that are targeted to a variety of cell and tissue types, and especially targeted to neuronal cells, however, other organs and tissues (e.g., lungs, kidneys, stomach, throat and esophagus, mammillary glands, testes, ovaries, uterus, colon, bone marrow, etc) may be targeted.

In particularly preferred embodiments, the compositions are able to cross (e.g., translocate) the blood brain barrier (BBB) and the cell membranes of neuronal cells. In some of these embodiments, the compositions are targetable by manipulation of magnetic fields around the subject. Preferably, the magnetic fields are created and controlled by magnetic resonance imagery (MRI) and like techniques and associated devices. However, in other embodiments, the compositions optionally comprise one or more molecular recognition elements (e.g., a portion of an antibody) that bind and/or aid the binding of the composition to biological targets (e.g., glioma cells).

In particularly preferred embodiments, the present compositions target and delivery hydrophilic and/or macromolecular therapeutic agents to biological targets. Prior to the present invention, the effective delivery of hydrophilic (e.g., dopamine) and macromolecular (peroxidase) pharmacological agents has been problematic, especially to neuronal cells and tissues. As discussed previously, medications used thus far in managing neurodegenerative diseases have been limited primarily to symptomatic treatments, such as drugs to replace missing neurotransmitters.

Recently, several neural growth factors (NGF) including the brain- or glial cell line-derived neurotropic factor (BDNF and GDNF, respectively) have provided profound effects on patient survival, high-affinity dopamine uptake, and neuritic outgrowth of fetal dopaminergic neurons in vitro. (See e.g., G. J. Siegel and N. B. Chauhan, Brain Res., 33:199-227 [2000]; D.S. Albeck et al., Neuro Report, 8:2293-2298 [1997]; and J. D. Cooper et al., Proc. Natl. Acad. Sci. USA, 98:10439-10444 [2001]). Since these NGF are large proteins that cannot cross the BBB, present therapies require NGFs to be administered by intracerebroventricular infusion. Although results from animal studies have revealed great promise for NGF therapies, these intracerebroventricular drug infusion methods are prohibitively intrusive and too complicated for real-time clinical applications.

Preferred compositions of the present invention provide delivery vehicles for translocating various NGFs directly into CNS tissues and especially directly into the brain. Accordingly, preferred embodiments of the present invention provides clinical feasible methods of delivering NGF directly into the brain. These embodiments, offer positive treatment of neurodegenerative diseases that actually promote neuronal survival, stimulate axonal growth, establish synaptic contacts.

Dowdy and coworkers demonstrated when conjugated to TAT, $\beta$-galactosidase ($\beta$-Gal) (116-Kda) is able to cross the BBB. (S. R. Schwarze et al., Science, 285:1569-1572 [1999]). By performing X-Gal staining on mid-hemisphere sagittal brain sections from mice four hrs after i.p. injection of TAT-$\beta$-Gal, Dowdy found that all regions of the brain displayed strong $\beta$-Gal activity. Low-magnification coronal brain sections also revealed $\beta$-Gal activity in cell bodies throughout the brain of the treated mice 8 hrs after injection. In the preferred embodiments, the present invention uses the confirmed cell translocating capabilities of PTDs (e.g., TAT, TAT-like peptides, LMWPs, etc) to translocate a wide variety of therapeutic agents (e.g., drugs, prodrugs, and the like) across biological membranes including the BBB and the cell membranes of neuronal cells. In particularly preferred embodiments, the present compositions translocate a variety of associated (e.g., attached) species including, but not limited to, hydrophilic, hydrophobic, small and large drugs and multivalent carriers drug carriers (e.g., polyrotaxane).

In an attempt to track the distribution and differentiation of progenitor and stem cells by high resolution in vivo imagining, Weissleder et al. demonstrated that they could transport the entire TAT-MION conjugate into cells. (L. Josephson et al., Bioconjugate Chem., 10:186-191 [1999]; and W. C. Enochs et al., J. Magn. Reson. Imaging, 9:228-232 [1999]).

In preferred embodiments, dopamine is linked to the TAT-MION conjugate via an isourea linkage using the well-established CNBr activation method (D. S. Kim et al., Drug Dev. Ind. Pharm., 27:97-101 [2001]). The present invention contemplates that isourea linkages are prone to hydrolysis, and the kinetics of their breakdown can be regulated by the natural hydrolysis process. (See e.g., D. S. Kim et al., supra; V. C. Yang and C. L. Teng, An immobilized protamine system for removing heparin in extracorporeal blood circulation. In: Biomimetic Polymers (C. Gebelein, ed.), pp. 175-190 [1990]; and J. Porath and R. Axen, Immobilization of enzymes to agar, agarose, and sephadex supports. In: Methods in Enzymology (K. Mosback, ed.) Vol. 44, pp. 19-45, Academic Press, NY [1976]).

In additional embodiments, the drug delivery compositions are repeatedly administered to a subject with little or no toxicity. For example, the present invention contemplates that administration of PTD (e.g., TAT)-MION conjugates themselves does not lead to significant toxicity.

In this regard, in preferred embodiments, the drug delivery compositions comprises biodegradable and/or biocompatible superparamagnetic nanoparticles, and in particular, biodegradable and/or biocompatible superparamagnetic iron oxide nanoparticles (MION). A number of studies demonstrate the non-toxicity of administering superparamagnetic nanoparticles and MIONs as clinical MRI agents wherein these compounds are known to be biodegradable and biocompatible. (See e.g., M. Lewin et al., Nature Biotechnol., 18:410-414 [2000]; M. Harisinghani et al., M, AJR, 172: 1347-1351 [1999]; T. Shen et al., Magn. Reson. Med., 29:599-604 [1993]; and R. Weissleder et al., AJR, 152:167-173 [1989]). Pharmacokinetic and toxicological studies indicate that MIONs are dissolved to iron, which is then incorporated into hemoglobin of erythrocytes and cleared primarily from liver (t1/2:3 days) and spleen (t1/2: 4 days). (See, R. Weissleder et al., supra). The bioavailability of MIONs are similar to that of common intravenous iron preparations, and have no significant acute or sub-acute toxic effects detectable by histological or serologic studies in rats or dogs.

Rat stroke models (See e.g., A. D. Doerfler et al., J. Magn. Resori. Imaging, 11:418-424 [2000]) demonstrate that bolus injections of MIONs at clinically relevant doses for brain imagining do not affect infarction volume, mortality, and the neurological and clinical outcome of acute cerebral ischemia. In vivo tracking and recovery of progenitor cell studies show that incorporation of TAT-MION conjugates into cells does not affect viability, differentiation, or proliferation. (See, M. Lewin et al., Nature Biotechnology, 18:410-414 [2000]). Additionally, it has been documented that TAT is neither toxic nor mutagenic (S. R. Schwarze et al. Science, 285:1569-1572 [1999]), and the TAT-mediated cellular uptake does not induce perturbation or damage of the cell membrane (T. Suzuki et al., J. Biol. Chem., 25:2437-2443 [2002]). Thus, the embodiments contemplated by the present invention are suitable for clinical administration and do not lead to toxic effects.

Based on the clinical levodopa dose of 300 mg per day (3 tablets daily; each tablet contains 100 mg levodopa and 25 mg carbidopa) and estimation that <1% of levodopa is converted to dopamine in the brain, the maximum requirement of dopamine in the brain for effective PD treatment is about three mg/day. (See, Dopamine Hydrochloride. In: AHFS Drug Information 2002,pp. 2383-2386, American Society of Health-System Pharmacists, Bethesda, Md. [2002]). In some embodiments, the present invention contemplates that the TAT-MION conjugates typically employed in clinical imaging contain about 6.7 TAT peptides and about 30 dextran molecules per MION particle, and an equivalence of 17.1 µmole iron (Fe) per 56 nmole of TAT. Thus, in some embodiments, if 30 dopamine molecules are conjugated to each dextran molecule (i.e., <20% of -OH groups on dextran will be used to link with dopamine), 1 µmole of TAT-MION would carry 2045 µmole of Fe and 178 mg (900 µmole) of dopamine (MW: 197 Da). Based on the data that the clinical dose of MION for imaging was about 2.2 mg Fe per kg of body weight (M. Harisinghani et al., AJR, 172:1347-1351 [1999]), a 70 kg patient would receive 153 mg (2,753 µmole) of iron in some embodiments. Therefore, a clinical dose of MION for imaging would provide 239 mg of dopamine; 80-fold higher than the required daily dopamine dose (3 mg) in the brain. Thus, in some embodiments, the present invention contemplates that a bi-weekly injection of the TAT-MION that contains a sufficient amount (about 42 mg) of dopamine for a 14-day sustained release, assuming that at least 30% of the administered TAT-MION are retained by the brain, requiring less than 50% of the MION dose used for clinical MR imaging.

Sub-acute and chronic toxic effects of iron overload have been documented in hemochromatosis if total body iron exceeds 15 g. Cirrhosis and hepatocellular carcinoma can develop if liver iron concentration exceeds 4000 mg/g wet weight (normal, 200 mg/g wet weight). Studies show that a single injection of MION would transiently increase liver iron from 200 to 212 mg/g wet tissue an increment that would require at least 300 injections of this dose to introduce hepatotoxicity. Based on the above estimation that 50% of the clinical imagining dose of dopamine-loaded MION are administered once every seven days as well as consideration of the pharmacokientics and excretion data reported for MION, the present invention contemplates that administration of the present dopamine-loaded MION is safe and nontoxic. Accordingly, in preferred embodiments the present dopamine and peroxidase-loaded, TAT-linked MION conjugates are clinically administered.

Figure 21A:
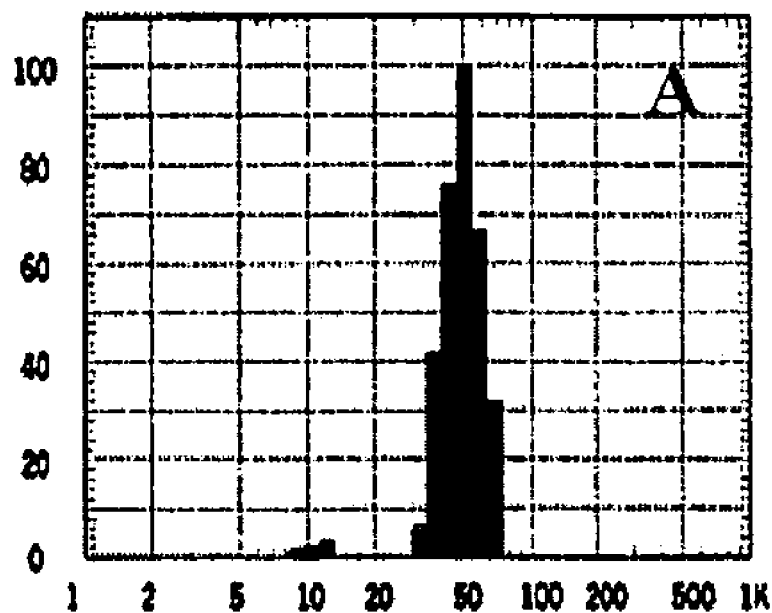
FIG. 21A shows the particle size distribution of synthesized TAT-MION conjugates with an average particle size of 49.2 nm.
Figure 21B:
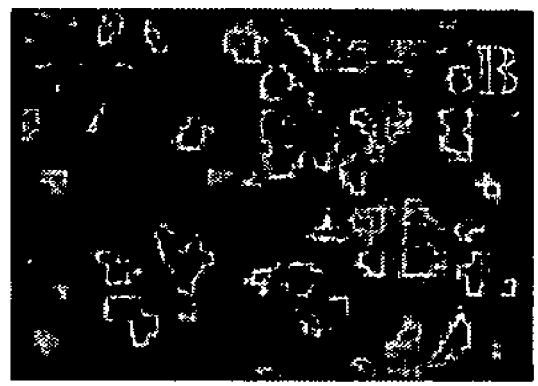
FIG. 21B shows fluorescence microscopy of HeLa cells incubated with TAT-MION for 30 min.
Figure 24:
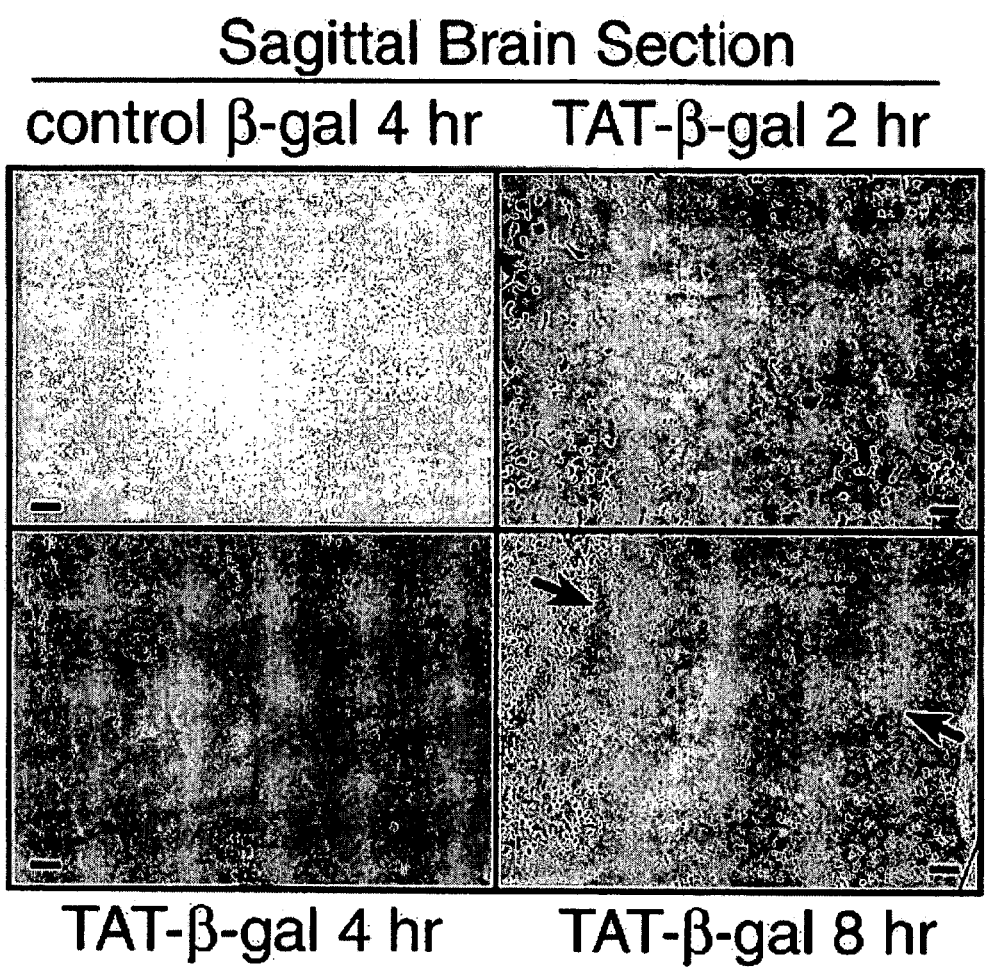
FIG. 24 shows the transduction of TAT-b-Gal across the blood-brain barrier. β-Gal activity (X-Gal staining) in hemispheric sagittal brain sections from mice injected intraperitoneally with TAT-b-Gal or control b-Gal; sections were made after the indicated times. (See, S. R. Schwarze, Science, 285:1569-1572 [1999]).

Preferred embodiments of the present invention demonstrate that: 1) TAT-linked MION conjugates can be successfully synthesized according to a number of procedures (See e.g., U.S. Pat. No. 5,262,176, incorporated by reference herein in its entirety); and 2) contemplated TAT-MION conjugates successfully internalize cells. As shown in FIG. 21A, the mean size TAT-MION conjugates, in one embodiment, was about 50 nm. Cellular uptake of the fluorescein isothiocyanate (FITC) labeled TAT-MION was observed 30 min after incubation with the cells, as reflected by the presence of a strong intensity of the FITC labels inside the cells (FIG. 21B).

In some preferred embodiments, the present invention provides drug delivery compositions for the direct targeting and delivery of therapeutic agents (e.g., dopamine) into a subject's CNS, and more particularly into the subject's brain. The drug delivery compositions of the present invention easily traverse the BBB and directly deliver therapeutic pharmalogical agents to the subject's brain. In preferred embodiments, the drug delivery compositions of the present invention offer numerous advantages over existing drug delivery systems. For example, in some embodiments, the proposed compositions for the direct delivery of dopamine to a subject's brain allow for a reduction of the drug dose by at least 100-fold, thus alleviating and possibly aborting the toxic side effects. Similarly, in other embodiments, the direct delivery of dopamine into a subject's brain prevents the "on/off effect" seen in late stage PD with existing levodopa treatments because the enzymatic conversion of levodopa to dopamine is avoided.

In still further embodiments, compositions that provide sustained dopamine release over long periods provide a constant and long-lasting dopamine concentration in the brain, thus greatly extending the overall span of effective drug therapy.

In other embodiments, the present compositions target and deliver peroxidase, a potent $H_2O_2$ scavenger, into a subject's brain and/or other CNS tissues. As mentioned previously, administration of levodopa treatments have raised concerns that increased free radical generation is concomitant. The present invention contemplates that the direct delivery of peroxidase into the brain expedites an enzymatic depletion of free radicals (e.g., $H_2O_2$) that may result from the conversion of levodopa into dopamine thus reducing the risk of enhanced oxidative stress caused by levodopa therapy or from other reactions that generate free radicals.

Indeed, some preferred embodiments of the present invention contemplate that the direct delivery of peroxidase (and other anti-free radical agents) provides new neuroprotective therapy to slow the progression of the diseases mediated by free radicals. Importantly, at present, no such therapies, or drug delivery systems are available.

In one embodiment, the present invention provides compositions that target and delivery a combination of therapeutic agents to diseased CNS tissues (e.g., degenerating neuronal cells associated with PD). For example, in certain embodiments the ability to deliver several different types of drugs into the brain creates the possibility of designing a synergic drug therapy regime involving several anti-PD drugs (e.g., selegiline, bromocriptine, etc). The present invention is not limited to providing compositions for the targeted delivery of the aforementioned therapeutic agents, nor is the present invention intended to be limited to delivering therapeutic agents to CNS tissues (e.g., the brain). For example, certain embodiments of the present invention are contemplated for the targeting and delivering numerous other therapeutic agents (e.g., drugs and/or prodrugs) to a wide variety of target tissues and cells (e.g., cancer cells).

In preferred embodiments, the drug delivery compositions of the present invention comprise magnetic nanoparticles coated with biocompatible polymers. In some of these embodiments, the compositions further comprise one or more cationic molecules (e.g., protein transduction domains) attached (e.g., bound) to the surface of the nanoparticle and/or the polymer surrounding the nanoparticle. In additional preferred embodiments, the compositions additionally comprise one or more therapeutic agents likewise attached to the surface of the nanoparticle and/or the polymer surrounding the nanoparticle. In other embodiments, species (e.g., drugs, prodrugs, molecular recognition elements, PTDs, radioisotopes, peptides, nucleic acids, etc) are associated with the polymer structure such that they are released by the degradation (e.g., gradual erosion) of the polymer materials. In this regard, the polymer materials typically function as either matrix devices (e.g., the drug is dispersed or dissolved in the polymer) or as reservoirs (e.g., the drug is encapsulated in the polymer) using known technologies. In matrix-like compositions of the present polymers, the therapeutic agents are generally released in a time-dependent manner, decreasing as time progresses. In the reservoir-like compositions of the present polymers, the therapeutic agents are typically released at a constant rate by diffusion through the polymer material.

In other embodiments, the therapeutic agents are attached to the surface of the polymer and available to target cells based on the pharmokinetic properties of the agent in the particular cell or tissue.

In still other embodiments, a pulsative release profile is provided, wherein there is a period where release of the therapeutic agent is effectively zero, followed by a pulse of agent release at a certain time. There are several methods for achieving a pulsative release profiles using different types of delivery systems that are compatible with the scope present invention with modifications routine to those skilled in the art. (See e.g., N. J. Medlicott and I. G. Tucker, Adv. Drug Delivery Reviews, 38:139-149 [1999]).

In some embodiments, the aforementioned cationic molecule is a protein transduction domain (PTD), including, but not limited to, TAT, TAT-like peptides, low molecule weight protamine derivative, and the like. Furthermore, in some of these embodiments, this molecule is selected for its ability to translocate (e.g., mediate) the entry of attached species (e.g., therapeutic molecules and other agents) across biological membranes, and in particular cell membranes. Thus, any molecule with strong cellular translocating capabilities is within the scope of the present invention and contemplated herein regardless of electrical charge (e.g., cationic, anionic, uncharged, and neutral molecules are all within the scope of the present invention).

In preferred embodiments, the compositions of the present invention allow therapeutic agents (e.g., drugs, prodrugs, and the like) or diagnostic agents (e.g., cell specific markers) to cross the BBB to achieve one or more of the following benefits: 1) reducing the dose of a therapeutic drug or diagnostic agent which, when given peripherally, maintains the biological or diagnostic potency in the nervous system; 2) allowing drugs that normally do not cross the BBB to penetrate into the nervous system, and 3) reducing the peripheral side effects by increasing the relative amount of the drug reaching the brain. Other benefits will be apparent to those skilled in the art.

Several investigators have successfully utilized MIONs and magnetic fields to target normal brain and brain tumors. (S. K. Pulfer et al., J. Neuro-Oncol., 41:99-105 [1999]; R. Weissleder et al., AJR, 152:167-173 [1989]; and S. K. Pulfer and J. M. Gallo, J. Drug Targeting, 3:215-227 [1998]). In targeting brain tumors, MION were able to aggregate in the interstitial space of the tumor due to morphological changes in the BBB that result in enhanced permeability. (S. K. Pulfer and J. M. Gallo, supra). Although intracerebral accumulation of MION in tumors occurs with or without application of magnetic fields, Pulfer et al. demonstrated that such accumulation was enhanced by more than 2-fold with the aid of a magnetic field. Further, accumulation of cationic MION, similar to those of the proposed TAT-MION, was increased by 2-4 fold over that of uncharged MION; due to an enhanced binding of the cationic MION to the negative cell surface.

Since MIONs cannot cross the BBB, when targeting non-tumorigenic brain tissues, the force of the subject's blood flow rapidly disperses the MIONs that initially lodge in the brain capillaries once the magnetic field is removed. (S. K. Pulfer and J. M. Gallo, supra). Consequently, there is large variability in the targeting specificity of the MIONs in normal brain tissues. In general, approximately 10% of the MIONs were localized in the capillaries of the normal brain if animals were sacrificed immediately after removing the magnetic field. (M. Lewin et al., Nature Biotechnol., 18:410-414 [2000]). Pairing these findings with the fact that TAT-MION conjugates are highly adsorptive to negative cell surfaces (because TAT is highly positively charged) and also capable of entering the brain quickly, the present invention contemplates that application of a magnetic filed enhances brain MION targeting and MION retention.

I. Elements of the Targeting Component

A. Molecular Recognition Elements

In preferred embodiments, the targeting component of the present drug delivery compositions comprises a molecular recognition element. The molecular recognition element is attached, fixed, or conjugated to other elements of the targeting component so that it can bind to a particular biological target (e.g., diseased cells, including tumor cells, tissues, and pathogens, such as bacteria, fungi, mycoplasma, prions, viruses, etc). It is contemplated that the drug delivery compositions of the present invention are targeted via the molecular recognition element to a variety of biological targets, including, but not limited to, tumor cells, bacteria, viruses, cell surface proteins, cell surface receptors, cell surface polysaccharides, extracellular matrix proteins, intracellular proteins and intracellular nucleic acids. The present invention is not limited to any particular molecular recognition element(s). Indeed a variety of molecular recognition elements are contemplated. Examples of molecular recognition elements that find use in the present invention include, but are not limited to, nucleic acids (e.g., RNA and DNA), polypeptides (e.g., receptor ligands, signal peptides, avidin, Protein A, antigen binding proteins, etc), polysaccharides, biotin, hydrophobic groups, hydrophilic groups, drugs, and any organic molecules that bind to receptors. It is contemplated that the drug delivery compositions of the present invention display (e.g., be conjugated to) one, two, or a variety of molecular recognition elements. In some embodiments of the present invention, a plurality (i. e., $\geq 2$) of molecular recognition elements are associated with targeting component of the drug delivery compositions. In some of these embodiments, the plurality of molecular recognition elements can be either similar (e.g., monoclonal antibodies) or dissimilar (e.g., distinct idiotypes and/or isotypes of antibodies, or an antibody and a nucleic acid, etc).

Utilization of more than one molecular recognition element in a particular drug delivery composition allows multiple biological targets to be targeted or to increase affinity for a particular target. Multiple molecular recognition elements also allow the drug delivery compositions to be "stacked," wherein a first drug delivery composition is targeted to a biological target, and a second drug delivery composition is targeted to the molecular recognition element on the first drug delivery composition.

In preferred embodiments of the present invention, molecular recognition elements are associated (e.g., covalently or noncovalently bound) to the other subcomponents/elements of the targeting component with either short (e.g., direct coupling), medium (e.g., using small-molecule bifunctional linkers such as SPDP [Pierce Biotechnology, Inc., Rockford, Ill.]), or long (e.g., PEG bifunctional linkers [Nektar Therapeutics, Inc., San Carlos, Calif.]) linkages.

1. Antibodies as Molecular Recognition Elements

In some embodiments of the present invention, the molecular recognition 25 elements are preferably antigen binding proteins or antibodies. Antibodies can be generated to allow for the targeting of antigens or immunogens (e.g., tumor, tissue, or pathogen specific antigens) on various biological targets (e.g., pathogens, tumor cells, normal tissue). Such antibodies include, but are not limited to polyclonal, monoclonal, chimeric, single chain, Fab fragments, and Fab expression libraries. 30 Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "$F_V$" area which contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

Various procedures known in the art are used for the production of polyclonal antibodies. For the production of antibody, various host animals can be immunized by injection with the peptide corresponding to the desired epitope including but not limited to rabbits, mice, rats, sheep, goats, etc In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

Monoclonal antibodies against target antigens (e.g., a cell surface protein, such as receptors) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than-the mouse system. Splenocytes from the transgenic mice are immunized with the antigen of interest which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggernan et al. Eur. J. Immunol., 21:1323-1326 [1991]).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and the PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies. (See e.g., Larrick et al., Biotechniques, 11:152-156 [1991]). A similar strategy can also been used to amplify human heavy and light chain variable regions from human antibodies (See e.g., Larrick et al., Methods: Companion to Methods in Enzymology, 2:106-110 [1991]).

In one embodiment, RNA is isolated from B lymphocytes, for example, peripheral blood cells, bone marrow, or spleen preparations, using standard protocols (e.g., US 4,683,292 [incorporated herein by reference in its entirety]; Orlandi, et al.,Proc. Nat. Acad. Sci. USA, 86:3833-3837 [1989]; Sastry et al., Proc. Nat. Acad. Sci. USA, 86:5728-5732 [1989]; and Huse et al., Science, 246:1275 [1989]). First strand cDNA is synthesized using primers specific for the constant region of the heavy chain(s) and each of the K and λ light chains, as well as primers for the signal sequence. Using variable region PCR primers, the variable regions of both heavy and light chains are amplified, each alone or in combination, and ligated into appropriate vectors for further manipulation ingenerating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries, examples of methods and reagents particularly amenable for use in generating a variegated antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809 [each of which is herein incorporated by refernce in its entirety]; Fuchs et al., Biol. Technology, 9:1370-1372 [1991]; Hay et al., Hum. Antibod. Hybridomas, 3:81-85 [1992]; Huse et al., Science, 46:1275-1281 [1989]; Hawkins et al., J. Mol. Biol., 226: 889-896 [1992]; Clackson et al., Nature, 352:624-628 [1991]; Gram et al., Proc. Nat. Acad. Sci. USA, 89:3576-3580 [1992]; Garrad et al., Bio/Technolog, 2:1373-1377 [1991]; Hoogenboom et al., Nuc. Acid Res., 19:4133-4137 [1991]; and Barbas et al., Proc. Nat. Acad. Sci. USA, 88:7978 [1991]. In certain embodiments, the V region domains of heavy and light chains can be expressed on the same polypeptide, joined by a flexible linker to form a single-chain Fv fragment, and the scFV gene subsequently cloned into the desired expression vector or phage genome.

As generally described in McCafferty et al., Nature, 348:552-554 (1990), complete $V_H$ and $V_L$ domains of an antibody, joined by a flexible linker (e.g., $(Gly_4\text{-}Ser)_3$) can be used to produce a single chain antibody which can render the display package separable based on antigen affinity. Isolated scFV antibodies immunoreactive with the antigen can subsequently be formulated into a pharmaceutical preparation for use in the subject method.

According to the invention, techniques described for the production of single chain antibodies (U.S. Pat. No. 4,946, 778; herein incorporated by reference) can be adapted to produce specific single chain antibodies. An additional embodiment of the invention utilizes the techniques described for the construction of Fab expression libraries (Huse et al., Science, 246:1275-1281 [1989]) to allow rapid and easy identification of monoclonal Fab fragments with the desired specificity.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g., from the phage genome) and subcloned into other expression vectors by standard recombinant DNA techniques.

Specific antibody molecules with high affinities for a surface protein can be made according to methods known to those in the art, e.g., methods involving screening of libraries U.S. Pat. No. 5,233,409 and U.S. Pat. No. 5,403,484 (both incorporated herein by reference in their entireties). Further, the methods of these libraries can be used in screens to obtain binding determinants that are mimetics of the structural determinants of antibodies.

Generally, in the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc), complement fixation assays, immunofluorescence assays, protein A assays, and immunoelectrophoresis assays, etc).

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence in formation, by a modeling procedure using previously determined three-dimensional structures from other antibodies obtained from NMR studies or crytallographic data.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are know in the art.

Other techniques include affinity chromatography with an appropriate "receptor," e.g., a target antigen, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library. (See e.g., W. C. Still et al., WO 94/08051, incorporated herein by reference in its entirety). In general, this method features the use of inert but readily detectable tags that are attached to the solid support or to the compounds. When an active compound is detected, the identity of the compound is determined by identification of the unique accompanying tag. This tagging method permits the synthesis of large libraries of compounds which can be identified at very low levels among to total set of all compounds in the library.

The term modified antibody is also intended to include antibodies, such as monoclonal antibodies, chimeric antibodies, and humanized antibodies which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314:446-449 [1985]; and Shaw et al., J. Natl. Cancer Inst., 80:1553-1559 [1988]).

The chimeric antibody can be further humanized by replacing sequences of the Fv variable region which are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are known and for example, may be obtained from 7E3, an anti-GPII$_b$III$_a$ antibody producing hybridoma. The recombinant DNA encoding the chimeric antibody, or fragment thereof, is then cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody are humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In preferred embodiments, the fusion proteins include a monoclonal antibody subunit (e.g., a human, murine, or bovine), or a fragment thereof, (e.g., an antigen binding fragment thereof). The monoclonal antibody subunit or antigen binding fragment thereof can be a single chain polypeptide, a dimer of a heavy chain and a light chain, a tetramer of two heavy and two light chains, or a pentamer (e.g., IgM). IgM is a pentamer of five monomer units held together by disulfide bonds linking their carboxyl-terminal (Cμ4/Cμ4) domains and CμB/CμB domains. The pentameric structure of IgM provides 10 antigen-binding sites, thus serum IgM has a higher valency than other types of antibody isotypes. With its high valency, pentameric IgM is more efficient than other antibody isotypes at binding multidimensional antigens (e.g., viral particles and red blood cells. However, due to its large pentameric structure, IgM does not diffuse well and is usually found in low concentrations in intercellular tissue fluids. The J chain of IgM allows the molecule to bind to receptors on secretary cells, which transport the molecule across epithelial linings to the external secretions that bathe the mucosal surfaces. In some embodiments, of the present invention take advantage of the low diffusion rate of pentameric IgM to help concentrate the fusion proteins of present invention at a site of interest.

In some preferred embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of the various isotypes, including, IgG (e.g., IgG1, IgG2, IgG3, IgG4), IgM, IgA1, IgA2, IgA$_{sec}$, IgD, of IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')$_2$, Fv or a single chain Fv fragment).

In preferred embodiments, the immunoglobulin subunit of the fusion proteins is a recombinant antibody (e.g., a chimeric or a humanized antibody), a subunit or an antigen binding fragment thereof (e.g., has a variable region, or at least a complementarity determining region (CDR)).

In preferred embodiments, the immunoglobulin subunit of the fusion protein is monovalent (e.g., includes one pair of heavy and light chains, or antigen binding portions thereof). In other embodiments, the immunoglobulin subunit of the fusion protein is a divalent (e.g., includes two pairs of heavy and light chains, or antigen binding portions thereof). In preferred embodiments, the transgenic fusion proteins include an immunoglobulin heavy chain or a fragment thereof (e.g., an antigen binding fragment thereof).

In some preferred embodiments, the antibodies recognize tumor specific epitopes (e.g., TAG-72 (Kjeldsen et al., Cancer Res., 48:2214-2220 [1988]; U.S. Pat. Nos. 5,892,020; 5,892,019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA)(U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res., 178:271-292 [1988]), MSA breast carcinoma glycoprotein termed (Tjandra et al., Br. J. Surg., 75:811-817 [1988]); MFGM breast carcinoma antigen (Ishida et al., Tumor Biol., 10: 12-22 [1989]); DU-PAN-2 pancreatic carcinoma antigen (Lan et al., Cancer Res., 45:305-310 [1985]); CA125 ovarian carcinoma antigen (Hanisch et al., Carbohydr. Res., 178:29-47 [1988]); YH206 lung carcinoma antigen (Hinoda et al., Cancer J., 42:653-658 [1988]). Each of the foregoing references are specifically incorporated herein by reference.

For breast cancer, the cell surface may be targeted with folic acid, EGF, FGF, and antibodies (or antibody fragments) to the tumor-associated antigens MUC 1, cMet receptor and CD56 (NCAM).

A very flexible method to identify and select appropriate peptide targeting groups is the phage display technique (See e.g., Cortese et al., Curr. Opin. Biotechol., 6:73 [1995]), which can be conveniently carried out using commercially available kits. The phage display procedure produces a large and diverse combinatorial library of peptides attached to the surface of phage, which are screened against immobilized surface receptors for tight binding. After the tight-binding, viral constructs are isolated and sequenced to identify the peptide sequences. The cycle is repeated using the best peptides as starting points for the next peptide library. Eventually, suitably high-affinity peptides are identified and then screened for biocompatibility and target specificity. In this way, it is possible to produce peptides that can be conjugated to dendrimers, producing multivalent conjugates with high specificity and affinity for the target cell receptors (e.g., tumor cell receptors) or other desired targets.

Related to the targeting approaches described above is the "pretargeting" approach (See e.g., Goodwin and Meares, Cancer (suppl.), 80:2675 [1997]). An example of this strategy involves initial treatment of the patient with conjugates of tumor-specific monoclonal antibodies and streptavidin. Remaining soluble conjugate is removed from the bloodstream with an appropriate biotinylated clearing agent. When the tumor-localized conjugate is all that remains, a gossypol-linked, biotinylated agent is introduced, which in turn localizes at the tumor sites by the strong and specific biotin-streptavidin interaction.

In some embodiments of the present invention, the targeting agents (moieties) are preferably nucleic acids (e.g., RNA or DNA). In some embodiments, the nucleic acid targeting moieties are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene, 137(1):33-9 [1993]); human nerve growth factor (Binkley et al., Nuc. Acids Res., 23(16):3198-205 [1995]); and vascular endothelial growth factor (Jellinek et al., Biochem., 83(34): 10450-6 [1994]). Nucleic acids that bind ligands are preferably identified by the SELEX procedure (See e.g., U.S. Pat. Nos. 5,475,096; 5,270,163; and 5,475, 096; and in PCT publications WO 97/38134, WO 98/33941, and WO 99/07724, all of which are herein incorporated by reference), although many methods are known in the art.

In other preferred embodiments, the antibodies recognize specific pathogens (e.g., *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, polio virus, and the like).

2. Peptides that Specifically Target Tumor Cells

In some preferred embodiments of the present drug delivery compositions, the molecular recognition elements comprise peptides that bind specifically to tumor blood vessels. (See e.g., Arap et al., Science, 279:377-80 [1998]). These peptides include, but are not limited to, peptides containing the RGD (Arg-Gly-Asp) motif (e.g., CDCRGDCFC; SEQ ID NO:1) (FIG. 2), the NGR (Asn-Gly-Arg) motif (e.g., CNGRCVSGCAGRC; SEQ ID NO:2) (FIG. 2), or the GSL (Gly-Ser-Leu; SEQ ID NO:3) (FIG. 2) motif. These peptides and conjugates containing these peptides selectively bind to various tumors, including, but not limited to, breast carcinomas, Karposi's sarcoma, and melanoma. It is not intended that the present invention be limited to particular mechanism of action. Indeed, an understanding of the mechanism is not necessary to make and use the present invention. However, it is believed that these peptides are ligands for integrins and growth factor receptors that are absent or barely detectable in established blood vessels. In some preferred embodiments, the peptide is preferably produced using chemical synthesis methods. For example, peptides can be synthesized by solid phase techniques, cleaved from the resin, and purified by preparative high performance liquid chromatography. (See e.g., Creighton (1983) Proteins Structures And Molecular Principles, W. H. Freeman and Co, New York N.Y.). In other embodiments of the present invention, the composition of the synthetic peptides is confirmed by amino acid analysis or sequencing.

In some preferred embodiments, the drug delivery composition molecular recognition elements comprise peptides that specifically bind to glioma cells. (See e.g., Debinski et al., Nature Biotech., 16:449-53 [1998]; Debinski et al., J. Biol. Chem., 270(28):16775-80 [1995]; and Debinski et al., J. Biol. Chem., 271(37):22428-33 [1996]). In some embodiments, the present invention contemplates using drug delivery compositions comprising IL13, or one of its variants, so that the drug delivery compositions bind to IL13 binding sites in glioma cells.

Human high-grade gliomas are uniquely enriched in IL13 binding sites. Many of the established brain tumor cell lines, primarily malignant gliomas, over-express hIL13 binding sites. Human malignant glioma cell lines express high number, up to 30,000, binding sites for hIL13 per cell. Of interest, glioblastoma multiforme (GBM) explant cells showed an extraordinary high number of hIL13 binding sites, up to 500,000 per cell. The binding of hIL13 is not neutralized by hIL4 on an array of established human glioma cell lines that includes U-251 MG, U-373 MG, DBTRG MG, Hs-683, U-87 MG, SNB-19, and A-172 cells. hIL13 can be engineered to increase its specific targeting of high-grade gliomas. The pattern for IL13- and IL4R sharing on normal cells requires IL13 to bind hIL4R This is confirmed by the fact that hIL13 binding is always fully competed by hIL4. The recently proposed model for this hIL13R suggests that the shared hIL13/4R is heterodimeric. This scenario would imply that hIL 13 may contain at least two receptor-binding sites, each recognizing a respective subunit of the receptor. The engineered hIL 13 variants (e.g., hIL 13.E13K or hIL13.E13Y) are deprived of cell signaling abilities (Debinski et al., [1998], supra). This is desirable because interaction with physiological systems contributes prominently to the dose-limiting toxicity of some biological therapeutics (e.g., cytokines). Significantly, the molecule of hIL13 appears not to be sensitive to a variety of genetically engineered modifications and these variants can be produced in large quantities. It is thus possible to divert the molecule of hIL13 from its physiological receptor and make it a non-signaling compound, while its affinity toward the HGG-associated receptor remains intact or is increased. Such forms of IL13 can serve as rationally designed vectors for variety of imaging and therapeutic approaches of HGG.

Given the grim prognosis following the identification of an intracranial malignancy, any strategy for the pre-, intra- or post-operative identification and removal of cancer cells is a significant improvement. Recent discovery of the expression of IL-13 receptors on the surface of all of the malignancies of glial origin provides a novel strategy for the accumulation and retention of drug delivery compositions within CNS cancers. The high-grade glioma-associated receptor for IL13 used in the present invention is much more specific than the receptor for either transferrin or EGF, since its normal tissue presence is negligible or null. In addition, the over-expression of the IL13R in gliomas is much more frequent and homogenous than that for EGF.

In some embodiments, nucleic acids encoding IL13 fragments, fusion proteins or functional equivalents or variants (e.g., hIL13.EI3K or hIL13.E13Y) thereof are cloned into an appropriate expression vector, expressed and purified (e.g., preferably as described in Debinski et al., Nature Biotech., 16:449-53 [1998]; Debinski et al., J. Biol. Chem., 270(28): 16775-80 [1995]; and Debinski et al., J. Biol. Chem., 271(37):22428-33 [1996]). In other embodiments of the present invention, vectors include, but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. Large numbers of suitable vectors are known to those of skill in the art, and are commercially available. Such vectors include, but are not limited to, the following vectors: 1) Bacterial—pQE70: pQE60; pQE-9 (Qiagen, Inc., Valencia, Calif.); pBS; pD10; phagescript; psiX174; pbluescript SK; PBSKS; pNH8A; pNH16a; pNH18A; pNH46A (Stratagene, Inc., La Jolla, Calif.); ptrc99a; pKK223-3; pKK233-3; pDR540; pRIT5 (Pharmacia, Peapack, N.J.); and 2) Eukaryotic-pWLNEO; pSV2CAT; pOG44; PXT1; pSG (Stratagene); pSVK3; pBPV; PMSG; and $pSV_L$ (Pharmacia). Any other plasmid or vector can be used as long as they are replicable and viable in the host. In some preferred embodiments of the present invention, mammalian expression vectors comprise an origin of replication, a suitable promoter and enhancer, and any necessary ribosome binding sites, polyadenylation site, splice donor and acceptor sites, transcriptional termination sequences, and 5' flanking non-transcribed sequences. In other embodiments, DNA sequences derived from the SV40 splice, and polyadenylation sites are used to provide the required nontranscribed genetic elements.

In other embodiments, the IL13 peptide or variant thereof is expressed in a host cell. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherrichia coli, Salmonella typhimurium, Bacillus subtilis*, and various species within the genera *Pseudomonas, Streptomyces,* and *Staphylococcus*, as well as, *Saccharomycees cerivisiae, Schizosaccharomycees pombe, Drosophila* S2 cells, *Spodoptera* Sf9 cells, Chinese Hamster Ovary (CHO) cells, COS-7 lines of monkey kidney fibroblasts, (Gluzman, Cell, 23:175 [1981]), C127, 3T3, HeLa and BHK cell lines.

In some embodiments of the present invention, IL13 or variants thereof are recovered or purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein refolding steps are used, as necessary, in completing configuration of the mature protein. In still other embodiments of the present invention, high performance liquid chromatography (HPLC) is employed for final purification steps.

Some embodiments of the present invention provide polynucleotides having the coding sequence fused in frame to a marker sequence that allows for purification of the polypeptide of the present invention. A non-limiting example of a marker sequence is a hexahistidine tag that is supplied by a vector, preferably a pQE-9 vector, that provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson, et al., Cell, 37:767 [1984]).

3. Signal Peptides as Molecular Recognition Elements

In some embodiments of the present invention, the molecular recognition element is preferably a signal peptide. These peptides are chemically synthesized or cloned, expressed and purified as described above. Signal peptides are used to target the drug delivery composition (or a portion thereof) to a discreet region within a cell. In some embodiments, a signal peptide is provided as an element of the drug delivery component of the present drug delivery compositions; alternatively, the signal peptide may be an element of the targeting component. In still other embodiments, a signal peptide is provided in additional to a primary molecular recognition element that is responsible for targeting the drug delivery component to a target cell or tissue (e.g., a cancer cell).

In some embodiments, specific amino acid sequences in proteins are responsible for targeting the carried drug (e.g., polypeptide) into cellular organelles and compartments. In some embodiments, the signal peptides direct protein import into mitochondria. In further embodiments, the molecular recognition element is preferably: NH- Met-Leu-Ser-Leu-Arg-Gln-Ser-Ile-Arg-Phe-Phe-Lys-Pro-Ala-Thr-Arg-Thr-Leu-COOH (SEQ ID NO:4) (See, FIG. 2). It is not intended that the present invention be limited to particular mechanism of action. Indeed, an understanding of the mechanism is not necessary to make and use the present invention. However, it is contemplated that this peptide forms an amphipathic helix that associates with mitochondrial membranes sites of protein import. This allows the peptide-drug delivery composition complex to attach to mitochondrial membranes. It is unlikely that the complex is internalized, since there are few pores of nm size on intact mitochondria.

In still other embodiments, the following nuclear localization signal is utilized:

NH-Pro-Pro-Lys-Lys-Lys-Arg-Lys-Val-COOH (SEQ ID NO:5) (See, FIG. 2). In another embodiment, SNAP-25, is utilized to deliver the drug delivery compositions to the presynaptic region of neuronal cells. It is not intended that the present invention be limited to particular mechanism of action. Indeed, an understanding of the mechanism is not necessary to make and use the present invention. However, it is contemplated that SNAP-25 is one of the prototypic v-SNARE proteins. SNAP-25 localizes specifically to the presynaptic terminals of neuronal cells and PC-12 cells in culture. It is not known which portion of the peptide is responsible for sorting to the presynaptic terminal. However, during cellular processing of the peptide, SNAP-25 becomes palmitoylated at a central Cys-quartet. These palmitylated groups help anchor the protein in the presynaptic membrane. SNAP-25 associates with syntaxin, and ultimately, with the entire vesicular fusion machinery in a calcium-activated presynaptic terminal.

4. Use of Nucleic Acids as Molecular Recognition Elements

In some embodiments of the present invention, the molecular recognition elements are preferably nucleic acids (e.g., RNA or DNA). In some embodiments, the nucleic acid molecular recognition elements are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene, 137(1):33-9 [1993]); human nerve growth factor (Binkley et al., Nuc. Acids Res., 23(16):3198-205 [1995]); and vascular endothelial growth factor (Jellinek et al., Biochem., 83(34): 10450-6 [1994]). Nucleic acids that bind ligands are preferably identified by the SELEX procedure (See e.g., U.S. Pat. Nos. 5,475,096; 5,270,163; and 5,475,096; and in WO 97/38134; WO 98/33941; and WO 99/07724 (all of which are herein incorporated by reference), although many methods are known in the art and in some embodiments are suitable or preferred.

5. Other Molecular Recognition Elements

The molecular recognition elements of the drug delivery compositions of the present invention may recognize a variety of epitopes on biological targets (e.g., pathogens, tumor cells, normal tissues). In some embodiments, molecular recognition elements are incorporated to recognize, target, or detect a variety of pathogenic organisms including, but not limited to, sialic acid to target HIV (Wies et al., Nature, 333:426 [1988]), influenza (White et al., Cell, 56:725 [1989]), Chlamydia (Infect. Immunol, 57:2378 [1989]), *Neisseria meningitidis, Streptococcus suis, Salmonella*, mumps, newcastle, and various viruses, including reovirus, Sendai virus, and myxovirus; and 9-OAC sialic acid to target coronavirus, encephalomyelitis virus, and rotavirus; non-sialic acid glycoproteins to detect cytomegalovirus (Virology, 176:337 [1990]) and measles virus (Virology, 172:386 [1989]); CD4 (Khatzman et al., Nature, 312: 763 [1985]), vasoactive intestinal peptide (Sacerdote et al., J. of Neuroscience Research, 18:102 [1987]), and peptide T (Ruffet al., FEBS Letters, 211:17 [1987]) to target HIV; epidermal growth factor to target vaccinia (Epstein et al., Nature, 318: 663 [1985]); acetylcholine receptor to target rabies (Lentz et al., Science 215: 182 [1982]); Cd3 complement receptor to target Epstein-Barr virus (Carel et al., J. Biol. Chem., 265:12293 [1990]); β-adrenergic receptor to target reovirus (Co et al., Proc. Natl. Acad. Sci. USA, 82:1494 [1985]); ICAM-1 (Marlin et al., Nature, 344:70 [1990]), N-CAM, and myelin-associated glycoprotein MAb (Shephey et al., Proc. Natl. Acad. Sci. USA, 85:7743 [1988]) to target rhinovirus; polio virus receptor to target polio virus (Mendelsohn et al., Cell, 56:855 [1989]); fibroblast growth factor receptor to target herpes virus (Kaner et al., Science, 248:1410 [1990]); oligomannose to target *Escherichia coli*; ganglioside $G_{M1}$ to target *Neisseria meningitidis*; and antibodies to detect a broad variety of pathogens (e.g., *Neisseria gonorrhoeae, V. vulnificus, V. parahaemolyticus, V. cholerae*, and *V. alginolyticus*, etc).

In still other preferred embodiments, the targeting component of the present compositions comprises a molecular recognition element that specifically binds a particular biological target (e.g., a tumor cell). In some embodiments, the targeting component of drug delivery composition comprises a molecular recognition element (i.e., antibody) that specifically binds to neoplastic cells through interaction of the element with particular moiety on the target's surface. However, any moiety known to be located on the surface of biological targets (e.g., tumor cells) finds use with the present invention. For example, an antibody directed against such a moiety targets the compositions of the present invention to cell surfaces containing that moiety (e.g., antigen). Alternatively, the molecular recognition element may be a ligand directed to a receptor present on the biological target surface or vice versa. Similarly, vitamins also may be used to target the therapeutics of the present invention to a particular biological target.

In some embodiments of the present invention, the molecular recognition element may also function as an agent to identify a particular tumor characterized by expressing a receptor that the element (ligand) binds with, for example, tumor specific antigens including, but are not limited to, carcinoembryonic antigen, prostate specific antigen, tyrosinase, ras, a sialyly lewis antigen, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary all find use with certain embodiments of the present invention. Alternatively, the molecular recognition element may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, CO029, TI-1, L6 and SAS. Of course, these are merely exemplary tumor suppressors and it is envisioned that the present invention may be used in conjunction with any other agent that is or becomes known to those of skill in the art as a tumor suppressor.

In preferred embodiments of the present invention, the drug delivery compositions are targeted to factors expressed by oncogenes. These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Receptors and their related ligands that find use in the context of certain embodiments of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the targeting aspect of the present invention include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, α-endorphin, α melanocyte stimulating hormone (α-MSH), cholecystokinin, endothelin I, galanin, gastric inhibitory peptide (GIP), glucagon, insulin, amylin, lipotropins, GLP-1 (7-37) neurophysins, and somatostatin.

In addition, the present invention contemplates that vitamins (both fat soluble and non-fat soluble vitamins) may be used as molecular recognition elements to target biological targets (e.g., cells) that have receptors for, or otherwise take up these vitamins. Particularly preferred for this aspect of the invention are the fat soluble vitamins, such as vitamin D and its analogues, vitamin E, Vitamin A, and the like or water soluble vitamins such as Vitamin C, and the like.

B. Anionic Elements

In preferred embodiments, the drug delivery compositions further comprise an anionic molecule (e.g., an anionic protein) as a subcomponent (e.g., element) of the targeting component. While an understanding of the mechanism is unnecessary to make and use the present invention, it is contemplated that electrostatic interactions between an anionic element (e.g., heparin) in the targeting component and a first cationic element (e.g., a PTD) in the drug delivery component masks the cell translocating capabilities of the first cationic element until the administration of a second more strongly cationic element which displaces the binding of the first cationic element. However, in some embodiments, the charge of the second cationic element in relation to the first cationic element is irrelevant, only the sum affinity of the subsequently administered compound for the anionic element is relevant. Indeed, the principle requirement of the subsequently administered compound is that it posses greater binding affinity for the anionic element than the does the first cationic element.

II. Elements of the Drug Delivery Component

Preferred embodiments of the present invention comprise two or more components optimized for delivering therapeutic agents (e.g., anticancer drugs) to cells and tissues of interest. In particularly preferred embodiments, one of the two components is a drug delivery component that in turn is comprised of subcomponents, elements, and other moieties. The subcomponents, elements, and other moieties of the drug delivery component are described in greater detail below.

A. Protein Transduction Domains

A number of technologies have been developed for introducing molecules (e.g., nucleic acids, peptides, drugs, etc) into target cells. For example, various technologies exist for gene transfer including viral vectors (e.g., retroviruses, lentiviruses, adenoviruses, and adeno-associated viruses), nonviral vectors (e.g., liposomes), receptor specific peptides, and microballistics and other high-energy transfer systems. Receptor specific peptides are typically designed to bind to molecules on target tumor cells and have been used for the targeted delivery of peptides and nucleic acids in vivo. However, various commentators report that the efficiency of internalization after peptide binding is not always high and in certain cases, the target cell's endocytic pathway prohibits the release of the agent in the appropriate cellular compartment. Many of the exiting peptide complexes deliver the agent to the cell's lysosome where the agent is destroyed by proteolytic degradation. Consequently, although receptor-ligand mediated peptide drug delivery systems may be appropriate for certain applications, they have many shortcomings as systems for delivering peptides and/or nucleic acids, and other agents to a variety of cell types.

In particularly preferred embodiments, the drug delivery compositions comprise a protein transduction domain (PTD). Protein transduction domains are reported as being very efficient at translocating molecules conjugated thereto into cells.

In some embodiments, the PTD comprise from about 10 to 100% amino acids residues. In other preferred embodiments, the PTD comprise from about 50 to 100% amino acids residues. In still other particularly preferred embodiments, the PTD comprise from about 75 to 100% amino acids residues. The PTDs contemplated for use in the present compositions include, but are not limited to, naturally occurring amino acids, and non-naturally (typically) occurring amino acids include (e.g., D-amino acids, 2-aminoadipic acid, 3-aminoadipic acid, beta-alanine, beta-aminooropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic aicd, desmosine, 2,2'-diaminopropionic acid, 2,3-diaminopropionic acid, E-ethylglycine, N-ethylasparagine, hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine, and the like.

In preferred embodiments, the PTD comprises one or more positively charged amino acids lysine, arginine, and/or histidine. However, in some embodiments, the PTDs optionally comprise uncharged (e.g., asparagines, glutamine, serine, threonine, and tyrosine), and negatively charged (e.g., aspartic acid, glutamic acid) amino acids.

1. TAT

In 1988, the groups of Green and Loewenstein, and Frankel and Pabo independently reported the discovery that a full-length (86 amino acid) TAT protein isolated from the Human Immunodeficiency Virus (HIV) could cross cell membranes and transactivate a viral genome. (M. Green and P. M. Loewenstein, Cell, 55:1179-1188 [1988]; and A. D. Frankel and C. O. Pabo, Cell 55:1189-1193 [1988]). However, use of TAT protein for intracellular delivery of biological compounds has only recently attracted attention. Fawell et al. demonstrated that heterogeneous proteins chemically crosslinked to a 36-amino-acid domain of the TAT protein (TAT-(37-72)) were able to transduce into cells. (S. Fawell et al., Proc. Natl. Acad. Sci, USA, 91:664-668 [1994]). Mann and Frankel showed that the minimal TAT transduction domain is based on a highly cationic 11 amino acid section of the TAT-peptide (YGRKKRRQRRR; SEQ ID NO:6) (FIG. 2). (See, D. A. Mann and A. D. Frankel, EMBO J., 10:1733-1739 [1991]).

This 11 amino acid sequence has been combined genetically and by chemical hybridization to a variety of species including, hydrophilic fluorescent probes (E. Vives et al., J.

Biol. Chem., 272:16010-16017 [1997]), metal chelates (A. Astriab-Fisher et al., Biochem. Pharmacol., 60:83-90 [2000]), oligonucleotides (V. Polyakov et aL, Bioconjugate Chem. 11:762-771 [2000]), various proteins up to 150 kDa in molecular weight (S. Fawell et al., Proc. Natl. Acad. Sci. USA, 91:664-668 [1994]; S. R. Schwarze and S. F. Dowdy, Trends Pharmacol., 21:45-48 [2000]; and M. Becker-Hapak et al., Methods in Enzy., 24:247-256 [2001]), liposomes (V. P. Torchilin et al., Proc. Natl. Acad. Sci. USA, 798:8786-91 [2001]), and even magnetic iron oxide nanoparticles (MION) as large as ~100 nm in size (L. Josephson et al., Bioconjugate. Chem., 10:186-191 [1999]), and was shown to translocate all such attached species into virtually all types of cells.

The mechanism by which TAT translocates molecules across cell membranes remains unclear, however, an understanding of the mechanism is unnecessary to make and use the present invention. The present invention contemplates that TAT is able to translocate across cell membranes in a receptor- and transporter-independent fashion. In a recent in vivo study, Schwartz showed that 4 hrs after intraperitoneal injection of a 120-kDa P-galactosidase (β-Gal) fused to TAT, β-Gal activity was found in all tissues in mice including the liver, heart, kidney, and even the brain. (S. R. Schwartz et al., Science, 285:1569-1572 [1999]). TAT's lack of cell type selectivity for protein transduction further indicates the presence of a receptor-independent cell entry mechanism. Suzuki et al. provide further evidence that TAT internalization occurs via a receptor-independent mechanism by treating cells with various endocytosis inhibitors such as, the microtubule-disrupting reagent colchicines, and trans-Golgi transport inhibitor brefedin A, and the like. (T. Suzuki et al., J. Biol. Chem., 277:2437-2443 [2002]).

While not being limited to any particular mechanism, the present invention contemplates that TAT transduction utilizes adsorption of the cationic TAT protein by negatively charged cell surfaces, probably via binding to the anionic heparin sulfate, since cellular uptake of TAT is significantly inhibited by heparin or dextran sulfate as well as by heparan sulfate or chondroitin sulfates A, B, and C. The present invention shows that treating the cells with anti-heparan sulfate antibody or heparinase III clearly reduced the degree of translocation mediated by TAT or TAT-like peptides. Investigations show that cellular uptake of gelonin- and RNase-TAT conjugates is negated by the presence of heparin, but can subsequently be restored by the addition of the heparin-neutralizing agent protamine. Internalization of TAT or TAT-like peptides does not produce any critical cell membrane perturbations. Additionally, TAT and TAT-like peptides do not appear to be cytotoxic or mutagenic. (S. R. Schwartz et al., Science, 285:1569-1572 [1999]).

In preferred embodiments, the efficiency of the present drug delivery systems using TAT mediated translocation of biomolecules through cell membranes can hardly be matched by any existing cell entry method including the most capable receptor-mediated endocytosis approaches. Biological responses can be readily detected even when the concentration of TAT protein in cell medium is as low as 1 nM with approximately $10^7$ TAT molecules able to enter a single cell.

However, prior to the present invention the art was unable to harness and control the unmatched translocating abilities of TAT and TAT-like peptides for use in drug delivery systems. For example, to improve the tumor penetrating ability of scFv(19), an antibody fragment specific for targeting the ED-B domain of fibronectin in the extracellular matrix surrounding tumor neovasculature, Niesner attempted the conjugation of scFv(19) with TAT. (U. Niesner et al., Bioconjugate Chem., 13:729-736 [2002]). Niesner's results showed that the transmembrane activity of TAT on the scFv(19)-TAT conjugate was so overwhelming that it completely masked the targeting function of scFv(19) antibody fragment. Consequently, a whole body distribution of the conjugates resembling the pharmacokinetic profile of TAT administered alone was observed. Tumor targeting of the conjugates was substantially reduced, simply because most of the conjugates had already entered the cells due to TAT before scFv(19) could exert any targeting function. In additional experiments, the cell translocating efficiency of TAT-antibody conjugates (e.g., anti-estrogen receptor antibody) was observed by confocol microscopy. The present invention determined that it took about 30 minutes to transduce 90% of FITC-labeled TAT-antibody conjugates into MCF-7 breast cancer cells at 37° C., whereas it required more than 2 hrs to reach the same degree of transduction with FITC-labeled antibodies alone.

TAT's demonstrated ability to cross all types of cell membranes makes it a powerful molecule in systems designed to address the aforementioned uptake problems in drug delivery. However, prior to the present invention, the severe lack of selectivity of TAT-mediated cell entry presented an insurmountable hurdle to utilizing TAT as a tool for effective intracellular drug delivery. Indeed, based on observations that TAT completely overpowers the selective targeting and internalization capabilities of antibodies in existing TAT-antibody drug delivery systems, the applicability of TAT-based transduction technologies for intracellular delivery of biopharmaceuticals in vivo had been seriously discredited. (See e.g., U. Niesner et al., Bioconjugate Chem., 13:729-736 [2002]).

Additionally, prior to the present invention the applicability of TAT-based transduction technologies were further discredited because TAT is an arginine-rich protein and is thus an excellent substrate for enzymatic degradation by trypsin and trypsin-like proteases in the subject's circulatory system. (See e.g., T. I. Prior et al., Biochemistry, 31:3555-3559 [1992]; and D. Derossi etal., J. Biol. Chem., 269: 10444-10450 [1994]). The compositions of the present invention effectively address these and other reported problems in TAT (and PTD) based drug delivery systems.

2. Additional Protein Transduction Domains

Additional PTDs contemplated for use in some embodiments include, but are not limited to, the Drosophila homeotic transcription factor Antp or (Ant PTD) (encoded by the antennapedia gene) (A. Joliot A et al., Proc. Natl. Acad. Sci. USA, 88:1864-1868 [1991]), and VP22 a 38kDA tegument protein from herpes simplex virus type-I (HSV-1) (G. Elliott and P. O'Hare, Cell 88:223-233 [1997]). Accordingly, in some embodiments, the present invention comprises a drug delivery system comprising a PTD component or subcomponent other that Antp and VP22 and related peptides. Examples, of some other specifically contemplated PTDs include the third a -helix (e.g., residues 43-58) of the *Drosophila Antennapedia* homeobox gene (RQIKIWFQNR-RMKWKK; SEQ ID NO: 7) (FIG. 3) (See, D. Derossi et al., J. Biol. Chem. 269:10444-10450 [1994]; D. Derossi etal., J. Biol. Chem., 271:18188-18193 [1996]; and D. Derossi et al., Trends Cell Bio., 8:84-87 [1998]), the artificially designed protein translocation domains KRIHPRLTRSIR (SEQ ID NO:8) (FIG. 3), PPRLRKRRQLNM (SEQ ID NO:9) (FIG. 3), and RRORRTSKLMKR (SEQ ID NO:10) (FIG. 3) (See, Z. Mi et al., Molecular Therapy, 2:339-347 [2000]), residues 267-300 of VP22 (M. Green and P.M. Loewenstein, Cell, 55:1179-1188 [1988]), synthetic poly(arginine) peptides with more than about six residues (D. J. Mitchell et al., J. Peptide Res., 56:318-325 [2000]) being either linear (T. Suzuki et al., J. Biol. Chem., 277:2437-2443 [2002]) or branch-chained (S. Futaki et al., Biochemistry, 41:7925-7930 [2002]), and arginine-rich non-toxic low molecular weight protamine (LMWP) peptides derived from protamine (L. C. Chang et al., AAPS Pharm. Sci., 3(2) Article 17 [2001]; L. C. Chang et al., AAPS Pharm. Sci., 3(2) Article 18 [2001]; and L. M. Lee et al., AAPS Pharm. Sci., 3(2) Article 19 [2001]) among others.

B. Exemplary Therapeutic Agents and Drugs

A wide range of therapeutic agents and drugs find use with the drug delivery components of the present invention. In the broadest sense, any therapeutic agent, drug, or prodrug that can be associated (e.g., attached to or coadministered) with the components of the present invention are suitable for delivery by the compositions and methods of the present invention.

Preferred compositions of the present invention provide specific targeting and delivery of effective amounts of at least one anticancer agent (e.g., a conventional anticancer agent, such as, a chemotherapeutic drugs, radioactive elements and compositions etc) or other therapeutic agent.

Anticancer agents suitable for use with the present invention include, but are not limited to, agents that induce apoptosis, agents that induce nucleic acid damage, agents that inhibit nucleic acid synthesis, agents that affect microtubule formation, and agents that affect protein synthesis or stability, and the like.

Classes of anticancer agents suitable for targeting and delivery by the compositions and methods of the present invention include, but are not limited to: 1) alkaloids, including, microtubule inhibitors (e.g., Vincristine, Vinblastine, and Vindesine, etc), microtubule stabilizers (e.g., Paclitaxel [Taxol], and Docetaxel, etc), and chromatin function inhibitors, including, topoisomerase inhibitors, such as, epipodophyllotoxins (e.g., Etoposide [VP-16], and Teniposide [VM-26], etc), and agents that target topoisomerase I (e.g., Camptothecin and Isirinotecan [CPT-1 1], etc); 2) covalent DNA-binding agents [alkylating agents], including, nitrogen mustards (e.g., Mechlorethamine, Chlorambucil, Cyclophosphamide, Ifosphamide, and Busulfan [Myleran], etc), nitrosoureas (e.g., Carmustine, Lomustine, and Semustine, etc), and other alkylating agents (e.g., Dacarbazine, Hydroxymethylmelamine, Thiotepa, and Mitocycin, etc); 3) noncovalent DNA-binding agents [antitumor antibiotics], including, nucleic acid inhibitors (e.g., Dactinomycin [Actinomycin D], etc), anthracyclines (e.g., Daunorubicin [Daunomycin, and Cerubidine], Doxorubicin [Adriamycin], and Idarubicin [Idamycin], etc), anthracenediones (e.g., anthracycline analogues, such as, [Mitoxantrone], etc), bleomycins (Blenoxane), etc, and plicamycin (Mithramycin), etc; 4) antimetabolites, including, antifolates (e.g., Methotrexate, Folex, and Mexate, etc), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc), pyrimidine antagonists (e.g., fluoropyrimidines [e.g., 5-fluorouracil (Adrucil), 5-fluorodeoxyuridine (FdUrd) (Floxuridine)] etc), and cytosine arabinosides (e.g., Cytosar [ara-C] and Fludarabine, etc); 5) enzymes, including, L-asparaginase, and hydroxyurea, etc; 6) hormones, including, glucocorticoids, such as, antiestrogens (e.g., Tamoxifen, etc), nonsteroidal antiandrogens (e.g., Flutamide, etc), and aromatase inhibitors (e.g., anastrozole [Arimidex], etc); 7) platinum compounds (e.g., Cisplatin and Carboplatin, etc); 8) monoclonal antibodies conjugated with anticancer drugs, toxins, and/or radionuclides, etc; 9) biological response modifiers (e.g., interferons [e.g., IFN-y, etc] and interleukins [e.g., IL-2, etc], etc); 10) adoptive immunotherapy; 11) hematopoietic growth factors; 12) agents that induce tumor cell differentiation (e.g., all-trans-retinoic acid, etc); 13) gene therapy techniques; 14) antisense therapy techniques; 15) tumor vaccines; 16) therapies directed against tumor metastases (e.g., Batimistat, etc); 17) angiogenesis inhibitors, and the like.

In some particularly preferred embodiments, the present invention provides administration of an effective amount of at least one therapeutic agent or drug that induces apoptosis in a subject.

In some other preferred embodiments, the subject has a disease characterized by overexpression of proteins associated with aberrant cellular division or growth such as cancer. In some of these embodiments, the subject has overexpression of Bcl-2 family protein(s) (e.g., Bcl-2 and/or Bcl-$X_L$). In some other embodiments, the subject has a disease characterized by aberrant angiogenic development. In still other embodiments, the subject has a disease characterized by aberrant autoimmunity. As used herein, "aberrant" refers to biochemical and/or physiological occurrences in a subject that are indicative of a disease state (e.g., inflammation, autoimmunity, uncontrolled cell growth and proliferation, etc). The present invention is not limited however to providing drug delivery compositions suitable for treating only the aforementioned disease states or aberrant conditions. Indeed, in other embodiments, the present drug delivery compositions and methods target and deliver therapeutic agents, drugs, and prodrugs suitable for treating infections, metabolic regulatory conditions (e.g., diabetes, hypertension, hyperthyroidism, and the like), and other diseases and conditions.

In one preferred embodiment, the present invention provides compositions that administer an effective amount of taxanes (e.g., Docetaxel) to a subject having a disease characterized by the overexpression of proteins indicative of abnormal cellular division or growth (e.g., anti-apoptotic proteins such as Bcl-2 and/or Bcl/$X_L$).

The taxanes (e.g., Docetaxel) are an effective class of anticancer chemotherapeutic agents. (See e.g., K. D. Miller and G. W. Sledge, Jr. Cancer Investigation, 17:121-136 [1999]). While the present invention is not intended to be limited to any particular mechanisms, taxane-mediated cell death is thought to proceed through intercellular microtubule stabilization and the subsequent induction of the apoptotic pathway. (See e.g., S. Haldar et al., Cancer Research, 57:229-233 [1997]).

In some other embodiments, the present invention provides compositions that effectively target and deliver two or more therapeutic agents, drugs, or prodrugs to target cells and tissues. For example, in one embodiment, the present invention provides compositions that specifically target and deliver a combination of the anticancer drugs cisplatin and taxol to cancerous cells and tissues.

Cisplatin and Taxol have a well-defined action of inducing apoptosis in tumor cells. (See e.g., Lanni et al., Proc. Natl. Acad. Sci. USA, 94:9679 [1997]; Tortora et al., Cancer Research, 57:5107 [1997]; and Zaffaroni et al., Brit. J. Cancer, 77:1378 [1998]). However, treatment with these and other chemotherapeutic agents is difficult to accomplish without incurring significant toxicity. Many anticancer agents currently in use are generally poorly water soluble, quite toxic, and even when given at low doses potentially affect normal cells as well as diseased cells (e.g., target cells). For example, Paclitaxel (Taxol) has shown excellent antitumor activity in a wide variety of tumor models such as the B16 melanoma, L1210 leukemias, MX-1 mammary tumors, and CS-1 colon tumor xenografts. However, Paclitaxel is poorly water soluble. The poor aqueous solubility of Paclitaxel presents a major problem for human administration. Thus, current clinical Paclitaxel formulations use a cremaphor to solubilize the drug. The human clinical dose range for Paclitaxel administration is about 200-500 mg. This dose is dissolved in a 1:1 solution of ethanol:cremaphor and diluted to one liter of fluid given intravenously. The cremaphor currently used is polyethoxylated castor oil. It is given by infusion by dissolving in the cremaphor mixture and diluting with large volumes of an aqueous vehicle. Notably, direct administration (e.g., subcutaneous) of Paclitaxel results in local toxicity and low levels of drug activity. Certain embodiments of the present invention provide compositions that effectively and very specifically target and deliver therapeutically promising, but potentially deleterious agents like Paclitaxel, only to targeted cells and tissues (e.g., cancer cells).

Certain additional embodiments of the present invention provide the opportunity to monitor the therapeutic outcome post delivery of the anticancer agents (e.g., Cisplatin and/or Paclitaxel) to a subject. The present invention contemplates that measuring the ability of these drugs to induce apoptosis in vitro is reported to be a marker for in vivo efficacy. (See, Gibb, Gynecologic Oncology, 65:13 [1997]). Therefore, in addition to the targeted delivery of either or both of these drugs to provide effective anti-tumor therapy and reduce toxicity, the effectiveness of the therapy can be gauged to monitor induction of apoptosis. Importantly, both therapeutics are active against a wide range of tumor types including, but not limited to, breast cancer and colon cancer. (Akutsu et al., Eur. J. Cancer, 31A:2341 [1995]).

Any pharmaceutical that is routinely used in a cancer therapy context finds use in the present invention. Conventional anticancer agents that are suitable for administration with the disclosed drug delivery compositions include, but are not limited to, adriamycin, 5-fluorouracil, etoposide, camptothecin, actinomycin-D, mitomycin C, or more preferably, cisplatin. These agents may be prepared and used as a combined therapeutic composition, kit, or in combination with immunotherapeutic agents, as described herein.

In some embodiments of the present invention, the drug delivery compositions of the present invention further comprise one or more agents that directly cross-link nucleic acids (e.g., DNA) to facilitate DNA damage leading to a synergistic, antineoplastic affects. In this regard, agents such as Cisplatin, and other DNA alkylating agents may be used. Cisplatin has been widely used to treat cancer, with efficacious doses used in clinical applications of about 20 mg/M$^2$ for 5 days every three weeks for a total of three courses. The compositions of the present invention may be delivered via any suitable method, including, but not limited to, orally, intravenously, subcutaneously, intratumorally, intraperitoneally, or topically (e.g., to mucosal surfaces).

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are administered through bolus injections intravenously at doses ranging from about 25-75 Mg/M$^2$ at 21 day intervals for adriamycin, to about 35-50 Mg/M$^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. For example, agents such as 5-fluorouracil (5-FU) are preferentially used by neoplastic tissue, making this agent particularly useful for targeting to neoplastic cells. The doses delivered may range from about 3 to 15 mg/kg/day, although other doses are possible with considerable variation according to various factors including stage of disease, amenability of the cells to the therapy, amount of resistance to the agents and the like.

In preferred embodiments, the anticancer agents used in the present invention are those that are amenable to association with the drug delivery component of the present compositions, or are otherwise coadministrable with the disclosed drug delivery compositions, in a subject, tissue, or cell without loss of fidelity of anticancer effect. More generally, preferred therapeutic agents and drugs for use in the compositions of the present invention are those that retain their biological efficiency when associated, or coadministered, with the compositions of the present invention.

For a more detailed description of therapeutic agents, such as anticancer agents (e.g., platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anticancer agents), those skilled in the art are referred to any number of instructive manuals including, but not limited to, the Physician's Desk reference and to Goodman and Gilman's "Pharmaceutical Basis of Therapeutics" 10th ed., Eds. Hardman et al., 2001.

In some embodiments, the drugs are attached (e.g., conjugated) to drug delivery component of the composition with photocleavable linkers. For example, several heterobifunctional, photocleavable linkers that find use with the present invention are described by Ottl et al. (Ottl et al., Bioconjugate Chem., 9:143 [1998]). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active form through exposure of the target area to near-ultraviolet light.

In an exemplary embodiment, the alcohol group of taxol is reacted with the activated ester of the organic-soluble linker. This product in turn is reacted with the partially-thiolated surface of an appropriate dendrimer (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (Pasani et al., Inorg. Chim. Acta; 80:99 [1983]; and Abel et al., Eur. J.

Cancer, 9:4 [1973]) can be used. When the conjugate is localized within tumor cells, it is exposed to laser light of the appropriate near-UV wavelength, causing the active drug to be released into the cell.

Similarly, in other embodiments of the present invention, the amino groups of Cisplatin (or an analog thereof) is linked with a very hydrophobic photocleavable protecting group, such as the 2-nitrobenzyloxycarbonyl group (Pillai, V.N.R. Synthesis: 1-26 [1980]). When exposed to near-UV light (about 365 nm), the hydrophobic group is cleaved, leaving the intact drug. Since the drug itself is hydrophilic, it diffuses into the tumor cell, where it initiates apoptosis.

An alternative to photocleavable linkers are enzyme cleavable linkers. A number of enzyme cleavable linkers have been demonstrated as effective anti-tumor conjugates and can be prepared by attaching cancer therapeutics, such as doxorubicin, to water-soluble polymers with appropriate short peptide linkers. (See e.g., Vasey et al., Clin. Cancer Res., 5:83 [1999]). The linkers are stable outside of the cell, but are cleaved by thiolproteases once within the cell. In a preferred embodiment, the conjugate PK1 is used. In some embodiments, enzyme-degradable linkers, such as Gly-Phe-Leu-Gly are used.

The present invention is not limited by the nature of the therapeutic technique. For example, other conjugates that find use with the present invention include, but are not limited to, using conjugated boron dusters for BNCT (Capala et al., Bioconjugate Chem., 7:7 [1996]), the use of radioisotopes, and conjugation of toxins such as ricin.

Antimicrobial therapeutic agents may also be used as therapeutic agents in the present invention. Any agent that can kill, inhibit, or otherwise attenuate the function of a pathogenic (e.g., microbial) organisms may be used, as well as any agent contemplated to have such activities. Antimicrobial agents include, but are not limited to, natural and synthetic antibiotics, antibodies, inhibitory proteins, anti-sense nucleic acids, membrane disruptive agents and the like, used alone or in combination. Indeed, any type of antibiotic may be used including, but not limited to, anti-bacterial agents, anti-viral agents, anti-fungal agents, and the like.

A well-studied antigen found on the surface of many cancers (including breast HER2 tumors) is glycoprotein p185, which is exclusively expressed in malignant cells (Press et al., Oncogene 5:953 [1990]). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegrarn et al., Proc. Am. Soc. Clin. Oncol., 14:106 [1995]).

C. Rotaxanes and Polyrotaxanes

In some embodiments of the present invention, the drug delivery component of the present invention comprises a multivalent molecule that binds, transports, and subsequently releases one or more molecules of therapeutic agent(s) at targeted sites. For example, in some embodiments directed to delivering doxorubicin to targeted cells and tissues, the drug delivery component comprises a polyrotaxane molecule. However, a number of other embodiments not directed to targeting and delivering doxorubicin may optionally also comprise rotaxanes and/or polyrotaxanes.

Polyrotaxanes are supermolecular assemblies of biocompatible and biodegradable molecular components. (See e.g., T. Ooya T and N. Yui, Crit. Rev. Ther. Drug Carrier Syst., 16:289-330 [1999]). The "rotaxane" portion of the name comes from the Latin words for wheel and axel thus the term "polyrotaxane" refers to a molecular assembly of many cyclic molecules (e.g., cyclodextrin) threaded onto a linear polymer (e.g., PEG) chain. Bulky blocking groups (e.g., tyrosine) are often introduced at the ends to cap the polyrotaxane from dethreading. Typically, small drug molecules are linked to the abundant —OH groups on the cyclodextrin molecules by either hydrolysable (e.g., ester) or enzyme-cleavable (e.g., disulfide) bonds to allow for sustained release of the attached drugs.

There are two main types of polyrotaxanes, linear polyrotaxanes and comb-like or side-chain polyrotaxanes. There are numerous methods for producing linear and side-chain polyrotaxanes. Side chain polyrotaxanes may be produced by such methods as grafting in the presence of macrocyclic species, radical polymerization of preformed semi-rotaxanes, and threading grafted polymers and capping with end groups.

Polyrotaxanes are characterized by the mechanical bonding by which a plurality of component molecules interlocked such that the interlocked structure cannot fragment into component pieces without the breaking several covalent bonds. In some embodiments, polyrotaxane end caps are linked to the polyrotaxane core with cleavable linkages thus permitting the controlled dethreading of the polyrotaxane into its cyclodextrin and PEG constituents, both of which are biocompatible and can be cleared from the body assuming low molecular weight (e.g., about 3-5 kDa) PEG is used in the core of the polyrotaxane. (See e.g., T. Ooya supra; and J. Watanabe et al., J. Biomater. Sci. Edn., 10:1275-1288 [1999]).

The present invention contemplates based upon the trafficking and localization of PTDs (e.g., LMWP) to the cytosol, that certain polyrotaxane based drug delivery compositions of the present invention provide a significant advancement in tumor treatment. The present invention further contemplates that once a PR-based drug delivery composition enters a tumor, the composition releases its therapeutic agent(s) (e.g., doxorubicin) in a sustained and controlled manner as the composition traverses cell membranes (e.g., travels to,the tumor core). Unlike most existing drug delivery systems that deliver agents to the tumor's surface, the PR-based compositions of the present invention provide deliver therapeutic agents to the entire targeted tissue (e.g., tumor mass).

Additionally, PR-based drug delivery compositions of present invention are further contemplated to decrease MDR. Certain embodiments also suggest that the PR-based drug delivery compositions and methods of the present invention effectively offset the MDR response seen in other systems for the administration of small molecule drugs when conjugated to polymeric polyrotaxane.

In still further embodiments, PR-based compositions and methods of the present invention provide substantial EPR-induced accumulation and localization of small drugs at target cells and tissues (e.g., tumor sites).

Figure 4:
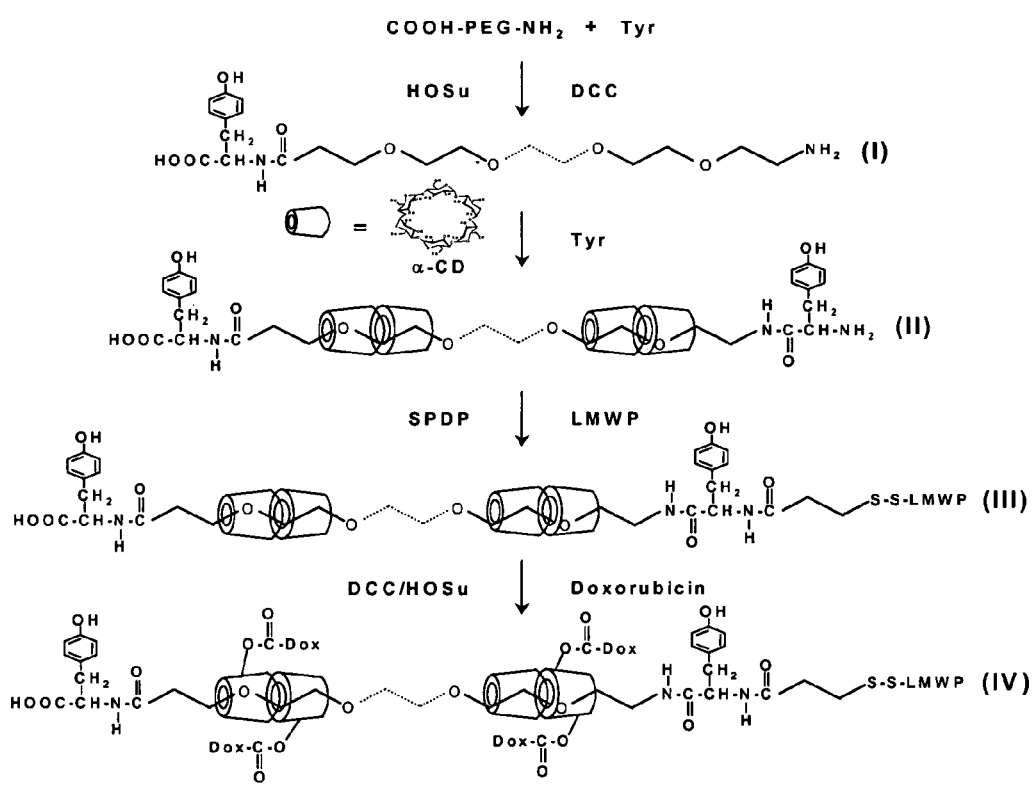
FIG. 4 provides an exemplary schematic for the synthesis of a polyrotaxane containing hydrolysable doxorubicin in one embodiment of the present invention.

FIG. 4 provides a schematic illustration of the synthesis of one contemplated polyrotaxane containing hydrolysable doxorubicin drug delivery composition. First, the carboxyl terminal of heterofunctional PEG ($H_2N$-PEG-COOH; MW: 3,400 Da) is activated by N-hydroxy-succinimide (HOSu) to induce coupling with the —$NH_2$ group of tyrosine (Tyr; the bulky blocking end). The —$NH_2$ group of $H_2N$-PEG-COOH is blocked by di-tert-butyl carbonate (Boc) prior to the activation of the —COOH group to prevent PEG from intramolecular crosslinking. This terminal Boc is later removed by the addition of trifluroacetic acid (TFA). To the prepared PEG with the terminal Tyrosine bulky end (Product (I)) α-cyclodextrin (α-CD) is added. After incubation of the reaction mixture at room temperature for 2 days, the $NH_2$ end of PEG is capped by using carboxyl-activated tyrosine to prevent dethreading of α-CD from the PEG chain (Product (II)). Thereafter; the tyrosine bulky end is thiolated using the SPDP activation method and conjugated with a LMWP peptide thiolated at the N-terminal by using the same SPDP activation as described herein via a disulfide linkage (Product (III)). To incorporate doxorubicin onto polyrotaxane, the α-CD residues are activated using succinic anhydride and pyridine, and doxorubicin is linked to the activated α-CD via hydrolysable ester linkages (Product (IV)).

II. The Blood Brain Barrier

Giving drugs that affect nervous system function or dysfunction in animals or patients can achieve the treatment of nervous system disorders. Typically, such drugs are given by peripheral application, via either the oral or the systemic route. While many drugs are able to cross the BBB, others do not pass the BBB efficiently or not at all and are only effective when given directly into the brain. The term "blood-brain barrier" or "BBB," as used herein, refers to the BBB proper as well as to the blood-spinal barrier. The blood-brain barrier acts to limit penetration of substances into the brain. The nature of the substance penetration through the BBB has not yet been determined but it is known that many of the regulators of brain function such as cytokines, transferrin, encephalins and endorphines can pass through the BBB from the blood vessels into the brain. (S. Raeissi and J. Audus, J. Pharm. Phy., 41:848-852 [1989]; B. Zlokovich et al., Peptides, 10:249-254 [1989]; and B. Zlokovich, J. Control. Rel., 13:185-201 [1990]). However, many substances which can affect the Central Nervous System (or CNS) such as adenosine, β-endorphin, synthetic analogs of endogenous peptides (R. A. Houghten et al., Proc. Natl. Acad. Sci. USA, 77:4588-4591 [1980]; E. R. Levin, etal., Biochem. Biophys. Res. Commun., 147:1226-1231 [1987]; T. Sakane et al., Int. J. Pharm., 57:77-83 [1989]), as well as some excitatory and inhibitor amino acids and trophic factors, penetrate poorly or not at all through the BBB. At present, drugs with no BBB penetration or poor BBB penetration can only be given by direct CNS infusion or by implantation of controlled-release polymers. (See e.g., U.S. Pat. No. 4,883,666, incorporated herein by reference in its entirety). Thus, many potentially potent drugs are not useful clinically due to their inability to pass the BBB. In addition, many drugs exist today which affect the brain in a desirable manner but cannot be used because they have severe side effects because they affect peripheral organs of the body and/or the peripheral nervous system. Certain embodiments of the present provide compositions and methods for targeting and delivering (e.g., translocating) therapeutic agents to cells and tissues of the CNS, including the brain.

The concept of a barrier between the blood and the brain emerged from experiments conducted by bacteriologist Paul Ehrlich in the late $19^{th}$ century. Ehrlich experiments showed that aniline dye derivates when administered intravenously in animals stained did not stain the animal's brain but did successfully stain all other parts of the animal's tissues. In contrast, additional studies by Ehrlich's contemporaries with dyes injected directly into animal's spinal fluid showed the tissues of the CNS were stained, however, the rest of the animal's tissues were unstained. In time the theory that a BBB existed was developed, tested, and adopted.

The blood brain barrier (BBB) is present in all vertebrate brains and is laid down within the first trimester of human fetal life. The cellular locus of the BBB are the endothelial cells of the brain capillaries. Thus, the compositions of the present invention are widely applicable to mediating the transport of associated therapeutic agents across the BBB of a wide number of commercially valuable vertebrate species (e.g., mammals such as cows, pigs, sheep, goats, horses, aves, such as, chickens, and turkeys, and fish, etc), domesticated animals (e.g., dogs and cats and the like), laboratory animals (e.g., roderits, such as mice, guinea pigs, rabbits, etc), as well as humans.

The endothelial cells that comprise the tubular capillaries in brain are cemented together by intercellular tight junctions. As an example of the tightness of these junctions, the electrical resistance across intraparenchymal endothelial cells in BBB approaches 8,000 $\Omega cm^2$. Moreover, the tight intercellular junctions have few pinocytotic vesicles and fenestrations and can block the passage of hydrophilic and virtually all compounds with molecular weights greater than about 500 Da.

The tight intercellular junctions eliminate the paracellular pathway of solute movement through the BBB and the virtually absence of pinocytosis across brain capillary endothelium eliminates transcellular flow of circulating solutes through the BBB. While an understanding of the mechanism is unnecessary to make and use the present invention, the present invention contemplates that solutes transverse the BBB and gain access to the brain interstitium by one of two mechanisms, lipid mediation, or catalyzed transport. Lipid-mediated transport is restricted to small molecules and is usually proportional to the lipid solubility of the molecule. Catalyzed transport across the BBB includes carrier-mediated or receptor-mediated processes.

The impermeability of the BBB is a function of the tightness of the endothelial cell junctions and the unique associations between several types of cells (e.g., astrocytes, pericytes, etc). For instance, the BBB is actually composed of the lumenal and the ablumenal membranes of brain capillary endothelial cells, which are separated by approximately 300 nm of endothelial cytoplasm. Therefore, transport systems must exist on both lumenal and ablumenal membranes of the endothelial cell if solute transcytosis from blood to brain is to occur. The BBB has a number of specialized carrier transport systems to mediate brain uptake of crucial nutrients (e.g., glucose, amino acids, choline, purine bases, or nucleosides, etc) carried by the blood stream. The nutrient carrier systems of the BBB mediate solute transport within milliseconds. In contrast, BBB receptor-mediated transport requires several minutes to complete. Receptor-mediated peptide transport through the BBB occurs through the presence of a number of different specific peptide-receptor systems.

Among all organs, the brain has historically been the least promising territory for pharmacological interventions. Delivery of drugs to the brain requires overcoming three major obstacles. First, like most organs, the brain lacks targeting specificity. Thus, any drug intended for treating a brain disease, when administered systemically or via other routes, also distributes to other untargeted organs, resulting not only in limited therapeutic effects in the brain, but also the potential for severe toxic side effects in nontargeted tissues. Second, the BBB, as mentioned above, is impermeable to most solutes.

One way to overcome the impermeability limitations of the BBB is to increase the relative amount of drug which passes the BBB. The reasoning is that if one can increase the amount of the drug crossing the BBB while reducing the peripheral dose of a given drug or diagnostic substance, the peripheral side effects of the drug are also less severe, while at the same time maintaining the desired effect in the brain.

A number of approaches have been attempted to overcome the impermeability of the BBB and to provide effective drug delivery of pharmalogicals to the brain and other CNS tissues, none of the existing approaches has achieved major success. (N. Doolittle et al., Clin. Cancer Res., 8:1702-1709 [2002]).

One approach has been to alter the function of the BBB itself. For instance, osmotic agents, when given peripherally (such as by intravenous injection), result in the opening of the BBB. Further, some drugs acting on the CNS can change the permeability of the BBB for other substances; cholinomimetic arecolines, for instance, have been reported to induce changes of drug penetration through the BBB. (A. Saija et al., J. Pharm. Pha., 42:135-138 [1990]). Other drugs which can be given to alter the permeability of the BBB are disclosed in U.S. Pat. Nos. 5,059,415 and 5,124,146 (herein incorporated by reference in their entireties). Bradykinin is one specific drug with such effects. (See, U.S. Pat. No. 5,112,596, herein incorporated by reference in its entirety). Another method comprises giving permeabilizer peptides such as A-7 or conformational analogs thereof. (WO 92/18529, herein incorporated by reference in its entirety). A relatively invasive method has been proposed by A. Tomasz and E. Tuomanen (WO 91/16064 herein incorporated by reference in its entirety) who give parenteral injections of purified cell wall or cell wall fragments of eubacteria such as Streptococcus pneumoniae to open the BBB. U.S. Pat. No. 5,260,210 (herein incorporated by reference in its entirety) discloses a method whereby the permeability of the blood-brain barrier is increased by giving an agent which reduces or interferes with cyclic AMP concentrations or which increases cyclic GMP concentrations.

The osmotic BBB disruption method is clinically feasible, yet highly undesirable since many potentially injurious compounds besides the intended drug molecules can also enter the brain during osmotic opening of the BBB. (See e.g., L. D. McAllister et al., Neurosurgery, 46:51-61 [2000]). Further, these effect are non-specific so these methods are impractical due to unpredictable and uncontrollable consequences to the nervous tissue.

Another approach is the modification of the drug molecules themselves. For instance, macromolecules, such as proteins, do not pass the BBB at all. For example, one can first isolate the macromolecule active site, i.e., the portion of the molecule which triggers the biologically desirable event, and then use only this active site. Since size is one of the factors in allowing permeability of the BBB, the reduced size is used in the hope that the smaller molecule can now pass the BBB. Other modifications to macromolecules to attempt passage of the BBB include glycating the proteins, thereby enhancing their permeability of the BBB, or forming a prodrug. U.S. Pat. No. 5,260,308 (herein incorporated by reference in its entirety) disclose glycating proteins, while U.S. Pat. No. 4,933,324 and WO 89/07938 (herein incorporated by reference in their entireties) disclose methods of formulating prodrugs. The prodrugs are formed from a fatty acid carrier and a neuroactive drug which is unable to pass across the BBB on its own. A similar system is disclosed in WO 89/07938 (herein incorporated by reference in its entirety).

Still another approach is the implantation of controlled release polymers which release the active ingredient from a matrix-system directly into the nervous tissue. However, this approach is invasive and requires surgical intervention if implanted directly into the brain or spinal cord. (U.S. Pat. No. 4,883,666, herein incorporated by reference in its entirety).

To overcome these limitations, another approach has been tried in which drug carrier systems are used such as liposomes, erythrocyte ghosts, antibody-conjugates, and monoclonal antibody conjugates. One of the major problems in targeted drug delivery is the rapid opsonization and uptake of injected carriers by the reticuloendothelial system (RES), especially by the macrophages in the liver and spleen. This obstacle may be partially overcome in the case of liposomes by incorporation of so-called "stealth" lipids, such as phosphatidylinositol, monosialoganglioside, or sulfogalactosylceramide. However, all of these systems lack the versatility to permit a wide-range application in medicine. These systems are all rather specific for particular purposes or particular drugs or diagnostic agents as indicated below. U.S. Pat. Nos. 5,182,107 and 5,154,924 (herein incorporated by reference in their entireties) disclose methods of conjugating a drug with an antibody wherein the antibody is reactive with a transferrin receptor. Transferrin receptors are located on brain capillary endothelial cells, which thus transport a drug, such as nerve growth factor, across the BBB. U.S. Pat. No. 5,004,697 (herein incorporated by reference in its entirety) improve such antibody-conjugate methods by providing cationized antibodies with a specific isoelectric point (See also, WO 89/01343, herein incorporated by reference in its entirety).

Still another approach is to create chimeric peptides to which the active agents are conjugated (U.S. Pat. No. 4,801,575, herein incorporated by reference in its entirety). Such a system is further discussed in U.S. Pat. No. 4,902,505 (herein incorporated by reference in its entirety) in which the chimeric peptide, such as histone, is capable of crossing the BBB by transcytosis.

U.S. Pat. Nos. 5,187,158 and 5,017,566 (herein incorporated by reference in their entireties) disclose brain-specific drug delivery methods wherein a centrally acting drug is given with the reduced, biooxidizable lipoidal form of a dihydropyridine reaction-pyridine salt redox carrier such as dopamine. (See also, U.S. Pat. No. 4,880,816, herein incorporated by reference in its entirety).

A rather invasive approach is taken to deliver genetic material to the brain. This is done by chemically disrupting the BBB and then using viruses to deliver genes across the BBB. (See, U.S. Pat. No. 4,866,042, herein incorporated by reference in its entirety). Here, a corrective genetic material is incorporated into a virus and the virus is then injected into the bloodstream.

Yet another carrier system approach uses liposomes, as disclosed in WO 91/04014 (herein incorporated by reference in its entirety). Briefly, liposomes are targeted to specific endogenous brain transport systems which transport specific ligands across the BBB. However, this system does not allow "non-penetrating" drugs to pass the BBB at all and is therefore very different from the present invention.

In still another approach with limited clinical utility, Brem and colleagues proposed the surgical implantation of drug-loaded polymers directly into brain tumors, as a method to bypass the BBB. (H. Brem et al., Lancet, 345:1008-1012 [1995]). Surgical implantation methods are beset by a number of limitations including, invasiveness, postoperative complications, expense, and complexity, limited availability and repeatability, etc). Third, effective delivery of drugs to the tissues of the CNS, and the brain in particular, require translocation of the drug molecules across the target cell membrane (e.g., membranes of the neuronal cells).

Normally, cellular uptake of drug-loaded nanomaterial based carriers such as polymers or liposomes is possible using receptor-mediated endocytosis approaches. These method, however, are hindered by a low uptake efficiency, especially in differentiated and non-dividing cells. (M. Lewin et al., Nature Biotechnol., 18:410-414 [2000]). Unfortunately, as described previously, neurons are one such type of non-dividing cells.

III. Nanoparticles

Generally, nanoparticles can be simple aggregations of molecules or they can be structured into two or more layers of different substances. For example, simple nanoparticles consisting of magnetite or maghemite can be used in magnetic applications (e.g., MRI contrast agents, cell separation tools, etc). (See e.g., Scientific and Clinical Applications of Magnetic Microspheres, U. Hafeli, W. Schutt, J. Teller, and M. Zborowski (eds.) Plenum Press, New York, 1997; Magn. Reson. Med., 31:268 [1994]; and Tiefenauer et al., Bioconjugate Chem., 4:347 [1993]). More complex nanoparticles can consist of a core made of one substance and a shell made of another. Many different type of small particles (nanoparticles or micron-sized particles) are commercially available from different manufacturers including, but not limited to, Bangs Laboratories (Fishers, Ind.); Promega (Madison, Wis.); Dynal Inc., (Lake Success, N.Y.); Advanced Magnetics Inc., (Surrey, U.K.); CPG Inc., (Lincoln Park, N.J.); Cortex Biochem (San Leandro, Calif.); European Institute of Science (Lund, Sweden); Ferrofluidics Corp., (Nashua, N.H.); FeRx Inc., (San Diego, Calif.); Immunicon Corp. (Huntingdon Valley, Pa.); Magnetically Delivered Therapeutics Inc., (San Diego, Calif.); Miltenyi Biotec GmbH (USA); Microcaps GmbH (Rostock, Germany); PolyMicrospheres Inc., (Indianapolis, Ind.); Scigen Ltd., (Kent, U.K.); Seradyn Inc., (Indianapolis, Ind.); and Spherotech Inc., (Libertyville, Ill.). Most of these particles are made using conventional techniques, such as grinding and milling, emulsion polymerization, block copolymerization, and microemulsion.

In preferred embodiments, the compositions of the present invention comprise superpara-magnetic nanoparticles as a vehicle for brain drug delivery. In particularly preferred embodiments, the compositions of the present invention comprise superpara-magnetic iron oxide nanoparticles, however, the present invention is not limited to compositions comprising only this type of nanoparticles. Indeed, in certain other embodiments, the present compositions optionally comprises other types of magnetic nanoparticles, including, but not limited to, cobalt (Co), cobalt ferrite, cobalt nitride, Cobalt oxide (Co—O), cobalt-palladium (Co—Pd), cobalt-platinum (Co—Pt), iron-gold (Fe—Au), iron-chromium (Fe—Cr), Iron nitride (Fe—N), iron oxide ($Fe_3O_4$), iron-palladium (Fe—Pd), iron-platinum (Fe—Pt), Fe—Zr—Nb—B, Mn nitride (Mn—N), Nd—Fe—B, Nd—Fe—B—Nb—Cu, nickel (Ni), and alloys, combinations, and derivatives thereof.

In some additional embodiments, the nanoparticles selected for use in the present compositions are not themselves magnetic (e.g., do not have a metallic center) but are associated (e.g., conjugated) to a magnetic particle (e.g., iron atom(s)). Furthermore, in some embodiments, the present invention contemplates that if even magnetic particles are use in the present compositions, their magnetic properties can be altered (e.g., enhanced) by association of one or more additional magnetic particles.

In particularly preferred embodiments, the nanoparticles used are coated with a biodegradable and/or biocompatible polymer. As used herein, the term "biodegradable," refers to a substance that is decomposed (e.g., chemically [e.g., enzymatically] broken down in component molecules) by natural biological processes (e.g., in vertebrate animals, and especially in humans). As used herein, the term "biocompatible," refers to a substance that has no unintended toxic or injurious effects on biological functions in a target organism.

A number of biodegradable and/or biocompatible polymers are suitable for use in the present invention, including, but not limited to, substantially pure carbon lattices (e.g., graphite), dextran, polysaccharides, polypeptides, polynucleotides, acrylate gels, polyanhydride, poly(lactide-co-glycolide), polytetraflouroethylene, polyhydroxyalkonates, cross-linked alginates, gelatin, collagen, cross-linked collagen, collagen derivatives, such as, succinylated collagen or methylated collagen, cross-linked hyaluronic acid, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyglycolide homoploymers, polyoxanones and polyoxalates, copolymer of poly(bis(p-carboxyphenoxy)propane)anhydride (PCPP) and sebacic acid, poly(1-glutamic acid), poly (d-glutamic acid), polyacrylic acid, poly(dl-glutamic acid), poly(1-aspartic acid), poly(d-aspartic acid), poly(dl-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin, silicone rubbers, or polyurethanes, and the like, all of which are known to be biocompatible and/or biodegradable.

Biocompatible polymers are not the only molecules contemplated for association with the nanoparticles element of the present compositions. Indeed, any molecule (e.g., ceramics, metals, etc) that is biocompatible (e.g., nonimmunogenic) in vertebrate animals and that is capable of forming bonds (e.g., covalent or noncovalent) with one or more additional molecules (e.g., PTDs and/or therapeutic agents) is specifically contemplated for use in the present compositions.

In particularly preferred embodiments, magnetic fields are used to manipulate (e.g., direct) the nanoparticles to target cells and tissues (e.g., CNS cells and tissues). However, the present compositions and methods are not intended to be limited to targeting and delivery therapeutic agents to CNS cells and tissues. Indeed, certain compositions of the present invention are directed to targeting and delivery therapeutic agents (e.g., pharmaceuticals) to other organs (e.g., kidneys, liver, spleen, colon, lungs, heart, bone marrow, etc).

A variety of protocols and techniques are known for directing magnetic nanoparticles to target sites in vivo using magnetic fields. For example, Pulfer et al. (S. K. Pulfer et al., J. Neuro-Oncol., 41:99-105 [1999]) reported a 2-21 fold increase in target selectivity for tumor over normal tissues when glioma tumors were targeted in rat brains using magnetic nanoparticles and magnetic fields.

Besides the high target site selectivity provided by magnetic nanoparticles, an additional desirable aspect of the present invention is that magnetic nanoparticles (e.g., MION) have been used clinically as a magnetic resonance contrast agents, and are proven to be biodegradable, biocompatible, and without acute or sub-acute effects after use on animals. (See e.g., M. Harisinghani et al., AJR, 172:1347-1351 [1999]; T. Shen et al., Magn. Reson. Med., 29:599-604 [1993]; and R. Weissleder et al., AJR, a152:167-173 [1989]).

Moreover, the present invention is not limited to the application of magnetic fields to direct the present drug delivery compositions to targeted cells and tissues. Indeed, in some embodiments, the present drug delivery compositions additionally comprise molecular recognition elements. The molecular recognition element is attached, fixed, or conjugated to other elements of the composition such that it can interact (e.g., bind) with particular biological targets (e.g., diseased cells, including tumor cells, tissues, and pathogens, such as bacteria, fungi, mycoplasma, prions, viruses, etc). It is contemplated that the drug delivery compositions of the present invention are targeted via the molecular recognition element to a variety of biological targets, including, but not limited to, tumor cells, bacteria, viruses, cell surface proteins, cell surface receptors, cell surface polysaccharides, extracellular matrix proteins, intracellular proteins and intracellular nucleic acids. The present invention is not limited to any particular molecular recognition element(s). Indeed a variety of molecular recognition elements are contemplated. Examples of molecular recognition elements that find use in the present invention include, but are not limited to, nucleic acids (e.g., RNA and DNA), polypeptides (e.g., receptor ligands, signal peptides, avidin, Protein A, antigen binding proteins, etc), polysaccharides, biotin, hydrophobic groups, hydrophilic groups, drugs, and any organic molecules that bind to receptors. It is contemplated that the drug delivery compositions of the present invention display (e.g., be conjugated to) one, two, or a variety of molecular recognition elements. In some embodiments of the present invention, a plurality (i.e., $\geq 2$) of molecular recognition elements are associated with the drug delivery compositions. In some of these embodiments, the plurality of molecular recognition elements can be either similar (e.g., monoclonal antibodies) or dissimilar (e.g., distinct idiotypes and/or isotypes of antibodies, or an antibody and a nucleic acid, etc).

Utilization of more than one molecular recognition element in a particular drug delivery composition allows multiple biological targets to be targeted or to increase affinity for a particular target. Multiple molecular recognition elements also allow the drug delivery compositions to be "stacked," wherein a first drug delivery composition is targeted to a biological target, and a second drug delivery composition is targeted to the molecular recognition element on the first drug delivery composition.

In preferred embodiments of the present invention, molecular recognition elements are associated (e.g., covalently or noncovalently bound) to the nanoparticle component of the present compositions with short (e.g., direct coupling), medium (e.g., using small-molecule bifunctional linkers such as SPDP [Pierce Biotechnology, Inc., Rockford, Ill.]), or long (e.g., PEG bifunctional linkers [Nektar Therapeutics, Inc., San Carlos, Calif.]) linkages.

IV. Exemplary Embodiments

A. Specific Molecular Recognition Elements

In some embodiments, the targeting component comprises an anionic molecule (e.g., heparin) conjugated to either $VEGF_{121}$ or the anti-CD20 antibody C2B8. In some of these embodiments, the heparin-VEGF/C2B8 conjugates are produced by coupling heparin via its terminal end and to the carbohydrate moiety of $VEGF_{121}$ or the Fc region of the C2B8 antibody. IgG, for example, normally contains about 3% carbohydrate in its Fc region. The present invention is not limited however, to any particular antibody iostype, for example, certain embodiments of the present invention comprise IgG (e.g., IgG1, IgG2, IgG3, IgG4), IgM, IgAl, IgA2, $IgA_{sec}$, IgD, IgE, and the like.

In preferred embodiments, the coupling of an anionic subcomponent of the targeting component to the Fc region of an antibody subcomponent (e.g., anti-CD22 C2B8) allows the drug delivery composition to leaves the Fab targeting region of the antibody intact and accessible to antigen binding. Moreover, the present invention contemplates that coupling heparin via its terminal end frees the entire heparin molecule for interaction, thereby maximizing binding with the PTD in the drug delivery component.

In some embodiments, the following brief protocol provides production of targeting components having an anionic molecule subcomponent (e.g., heparin) conjugated to either an antibody (or portion thereof) (e.g., C2B8) or a glycoprotein (e.g., $VEGF_{121}$) and the molecular recognition element.

Figure 19:
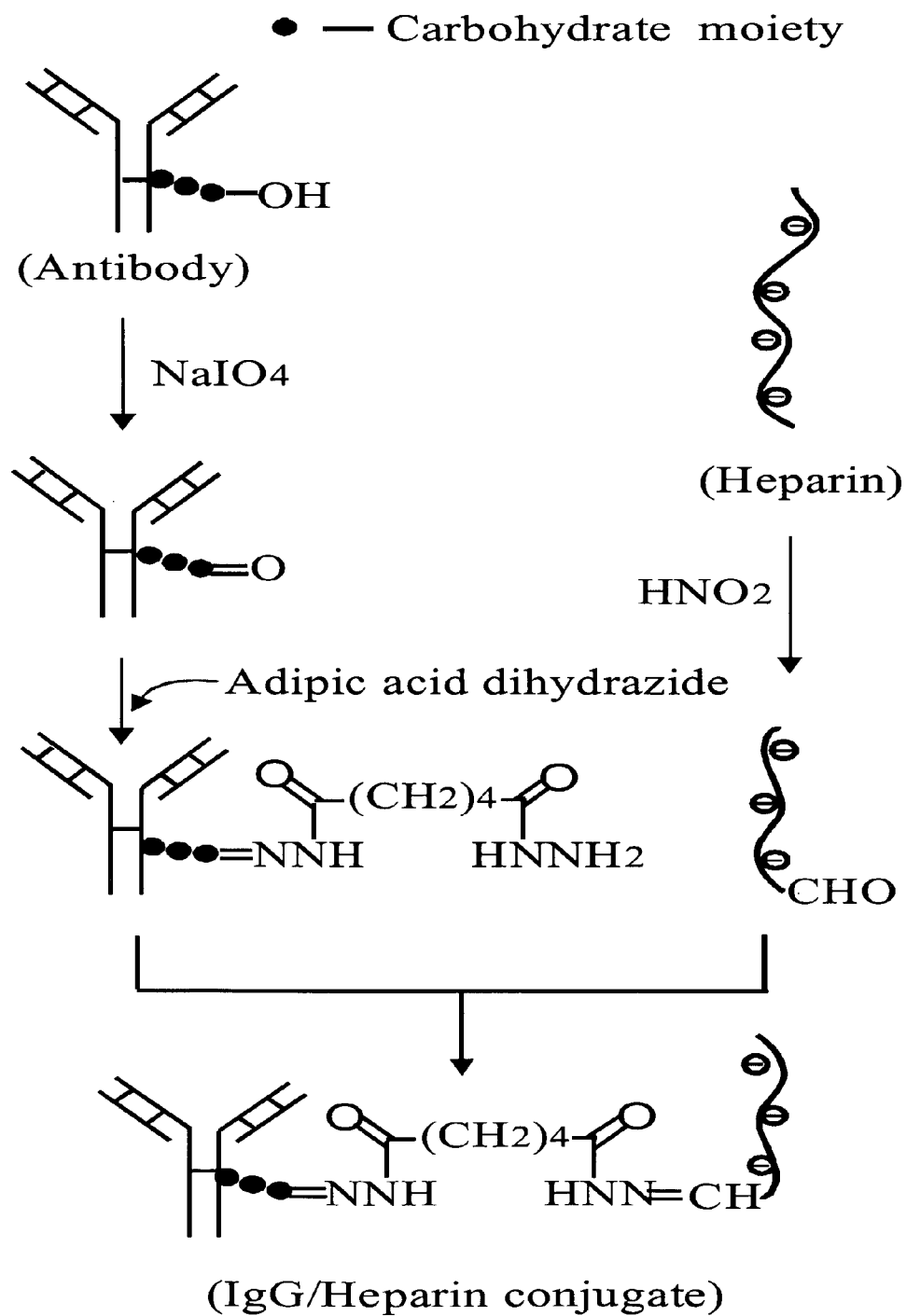
FIG. 19 provides a schematic illustration of one contemplated conjugation strategy for preparing heparin-antibody conjugates.

In some embodiments, the following protocol is used for production of heparin/antibody/glycoprotein conjugates. (See, FIG. 19). Briefly, under mild and acidic conditions (pH 4-5), sodium periodate ($NaIO_4$) oxidizes the vicinal —OH groups of the carbohydrate targeting moiety subcomponent to reactive aldehyde groups that can then be used for subsequent coupling reactions. Adipic dihydrazide is then added to further convert the newly formed aldehyde groups into highly reactive hydrazide groups. In some embodiments, the step of converting the reactive aldehyde groups to more highly reactive hydrazide groups, means that coupling of heparin to the antibody preferentially takes place under basic conditions using heparin's amino groups. Accordingly, in some of these embodiments, the heparin molecule is linked specifically at its reducing terminal via an aldehyde group to form a hydrazone linkage with the dihydrazide-treated antibody. In some embodiments, the dihydrazide activation step of the above procedure enables the anionic targeting subcomponent (e.g., heparin) to be linked to an antibody (e.g., IgG) via an end-point attachment. This attachment leaves the anionic molecule free for maximum dynamic interaction with the PTD (e.g., TAT, TAT-like peptide, LMWP etc) rendering the membrane-translocating functions of the PTD inactive. It has been well documented that immobilization of heparin via an end-point attachment preserves the maximum biological activity of heparin. (See e.g., P. Olsson and O. Larm Int. J. Artif. Organs, 14:453-456 [1991]). Consistent with these findings, the present invention shows that heparin linked to an anti-fibrin antibody using retained >90% of its binding affinity towards ATIII (anticoagulant activity) as well as towards LMWP. In addition, the targeting functions of the antibody were also almost fully (>90%) preserved.

B. Heparin-Binding Strength Studies

In preferred embodiments of the present invention, the electrostatic interactions between a highly anionic subcomponent (e.g., heparin molecule) of the targeting component and a highly cationic subcomponent (e.g., a PTD such as TAT) of the drug delivery component are canceled by the administration of a third molecule that binds the anionic subcomponent more strongly than the existing cationic subcomponent. In some of these embodiments, the third molecule comprises protamine (a known heparin antidote). The interaction of heparin, TAT, and protamine found in some embodiments of the present invention is described more fully below.

The prelude to all heparin-induced biological functions in blood is heparin's binding to antithrombin III (ATIII). ATIII possesses a stronger affinity for heparin than all other heparin-binding proteins normally found in the blood. Certain embodiments of the proposed drug delivery compositions rely on the electrostatic interactions between heparin and a PTD (e.g., TAT) to inhibit the PTD-mediated entry of drug molecules into nontargeted cells and tissues. Subsequent administration of a heparin antidote (e.g., protamine) reverses the heparin-induced inhibition once the drug delivery compositions have reached their intended targets via the molecular recognition element(s). While the present invention is not limited to any particular mechanism and an understanding of potential mechanisms is unnecessary to make and use the present invention, it is contemplated that proper function of the drug delivery compositions requires heparin bind to TAT stronger than ATIII, but weaker than protamine. The proposed mechanism allows drug TAT-drug conjugates to remain attached to, and thus inhibited from TAT-mediated cell entry by the appended heparin-antibody counterpart following intravenous administration, and yet be able to escape heparin inhibition and restore the TAT-mediated cell internalization upon administration of a heparin antidote (e.g., protamine).

In one embodiment, the protamine sensor developed by J. H. Yun (J. H. Yun et al., Anal. Chem., 224:212-220 [1995]) is used as a probe for detecting the titration end-points (J.H. Yun et al., Electroanalysis, 5:719-724 [1993]) and the binding strength of a number of heparin-binding proteins and arginine-rich peptides. (J. H. Yun et al., Pharm. Sci. Technol. Today, 2:102-110 [1999]). In some embodiments, the binding constant determined for LMWP (Keq=0.76 $M^{-1}$) is substituted for that of TAT, as it is in-between the binding constant for ATIII (Keq=0.56 $M^{-1}$) and protamine (Keq=24.6 $M^{-1}$). (See e.g., L. C. Chang et al., AAPS PharmSci., 3(2) Article 18 [2001]; and J. H. Yun et al., Electroanalysis, supra). Accordingly, in some embodiments, since the amino acid sequences of LMWP and TAT are similar, the present invention contemplates that either LMWP or TAT function appropriately as PTDs in drug delivery compositions with heparin/antiheparin administration.

C. Protein Transduction Domain Biodegradation

Preferred embodiments of the drug delivery compositions of the present invention resist biodegradation until at least the reach target cells and tissues. In previous drug delivery systems, and previous PTD based drug delivery systems in particular, the biodegradation of the systems prior to reaching their intended targets was a major flaw.

Many PTDs, including arginine-rich peptides (e.g., LMWP and TAT), are susceptible to degradation by trypsin-like proteases. Indeed, it has been suggested that in order to maintain the membrane translocating abilities of LMWP and TAT in vivo, D-amino acid-substitution is required. (U. Niesner et al., Bioconjugate Chem., 13:729-736 [2002]). Contrary to existing approaches, preferred embodiments of the present invention provide drug delivery compositions comprising PTDs (e.g., LMWP, TAT, TAT-like, etc) which are protected from trypsin and trypsin-like protease biodegradation by their electrostatic interactions with anionic (e.g., heparin) subcomponents. However, in certain other embodiments, the present invention provides drug delivery compositions having PTDs comprising D-amino acids (e.g., from about 5-100%).

In one embodiment, samples containing TAT-heparin complexes were digested by trypsin before and after the addition of protamine. All samples were then analyzed by HPLC chromatography on a heparin-column. Control samples containing typsin-digested TAT, intact TAT, and protamine eluted from the heparin-column in order of increasing ionic strength. On the other hand, samples that contained TAT-heparin complexes digested by trypsin prior to the addition of protamine displayed peaks indicating intact TAT, whereas samples that were digested after the addition of protamine showed the disappearance of the TAT peak accompanied by the appearance of a peak related to TAT degradation products. These results confirmed that TAT is protected from trypsin degradation in preferred embodiments of the present invention.

D. Specific Antibody Molecular Recognition Elements and Molecular Targeting

In preferred embodiments of the present invention, the molecular recognition element(s) of the drug delivery compositions ensure that therapeutic agents are delivered only to targeted cells and tissues. In some of these embodiments, the molecular recognition element(s) of the drug delivery compositions comprise antibodies or portions of antibodies. Accordingly, in preferred embodiments, the antibodies used in the targeting component remain functional following administration thus maintaining targeting selectivity.

Prior to the present invention, however, Niesner et al., demonstrated that the presence of PTDs (e.g., TAT) in PTD-antibody conjugates masked the targeting capabilities of the antibodies. (U. Niesner et al., Bioconjugate Chem., 13:729-736 [2002]). Contrary to the work of Niesner and others, the PTD-antibody based conjugates of the present invention are not significantly hampered by antibody masking. While not being limited to any particular mechanism, the present invention contemplates that the electrostatic interactions between cationic PTDs (e.g., LWMP, TAT, TAT-like peptides etc) in the drug delivery component and anionic subcomponents (e.g., heparin) in the targeting component protect the antibody's targeting capabilities from being masked by the PTDs.

Figure 5:
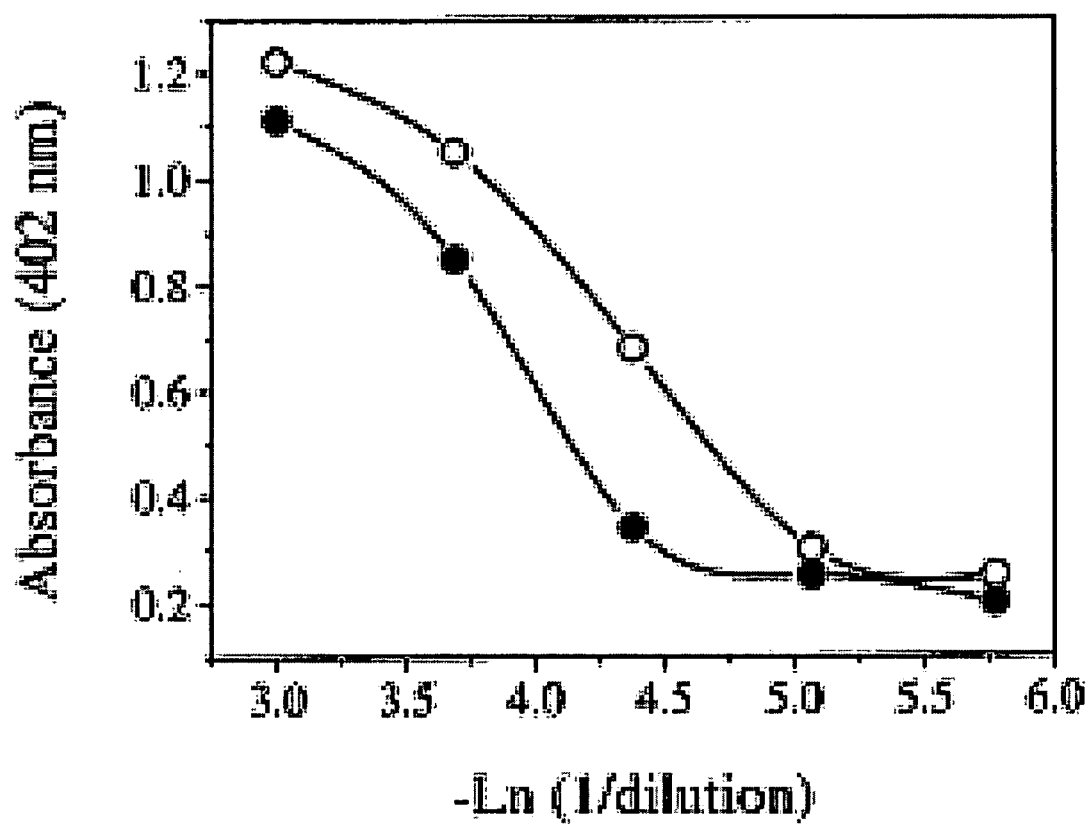
FIG. 5 shows the targeting function of anti-fibrin antibody (○), and an anti-fibrin antibody-heparin conjugate that was combined with TAT (●). Targeting activity was measured using an ELISA assay previously described by J. F. Liang. (J. F. Liang et al., AAPS PharmSci., 2(1) Article 7 [2000]).

For example, in some embodiments, an anti-fibrin antibody was conjugated to heparin to demonstrate the ability of the present compositions to retain the targeting capabilities of its antibody subcomponents. The fibrin-targeting functions of the heparin-IgG conjugates were compared in the presence and absence of TAT using an ELISA assay according to the methodology of J. F. Liang et al., AAPS PharmSci., 2(1) Article 7 (2000). As shown in FIG. 5, binding of TAT did not affect the functions of the heparin-IgG conjugates, as nearly 85% of anti-fibrin activity was observed when compared to the activity ofthe parent antibody. The loss of ~15% of anti-fibrin activity was likely due to the conjugation of heparin to the antibody, because the heparin-IgG conjugates displayed the same anti-fibrin activity with or without binding TAT. These findings suggest that the biological functions of PTDs, and especially TAT, are inhibited in the presence of heparin and as a consequence the antibody in the present compositions retain their full targeting capabilities and specificities.

E. PTD-Gel Conjugates

In some embodiments of the present invention, the drug delivery compositions are optimized for carrying, targeting, and translocating hydrophilic macromolecular drugs (e.g., gelonin [Gel]) across target cell and tissue membranes. As a class of compounds, hydrophilic macromolecular anticancer drugs have shown great therapeutic promise but have provided limited therapeutic success mainly because of their poor cellular uptake. For example, gelonin (MW of 30 kDa) is a member of type I ribosome-inactivating protein (RIP) family for cancer treatments. Despite the gelonin's potent ability to inhibit protein synthesis, native gelonin exhibits low tumor cell cytotoxicity because it is unable to cross cellular membranes. (See e.g., M. Wu, Brit. J. Cancer, 75:1347-1355 [1997]). Thus, gelonin's native lack of cell-entering ability provides an ideal system to demonstrate the effectiveness of the present compositions and methods to delivery hydrophilic macromolecular drugs to targeted cells.

1. Preparation of TAT-Gelonin Conjugates

In some embodiments, peptides containing the TAT sequence and a C-terminal cysteine residue (for coupling) were synthesized by the Protein Core Facility Center at the University of Michigan. In certain embodiments, the TAT peptide was coupled via the -OH group on the carbohydrate moiety of gelonin using PDDH (a hetero-bifunctional cross-linker). Following coupling, the product was purified using a heparin-immobilized column. The yield of the final conjugate recovered from the heparin-column was about 80-85%.

Figure 6:
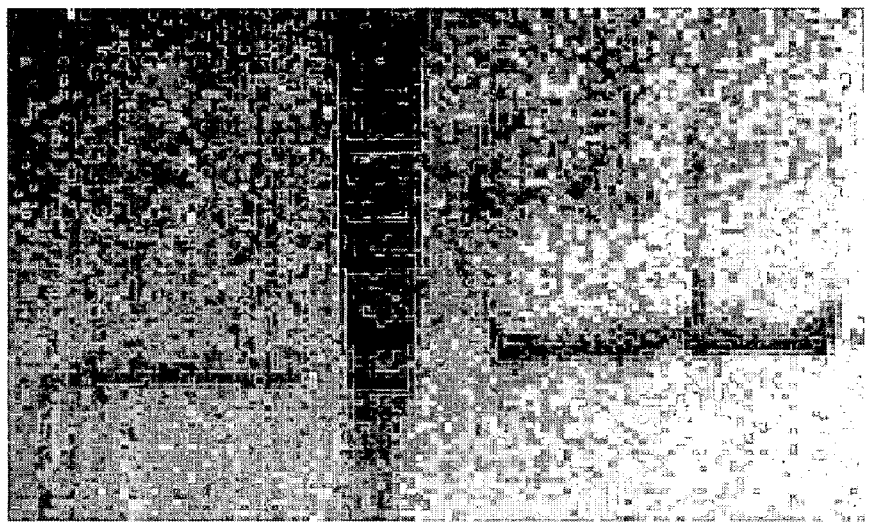
FIG. 6 shows an SDS-PAGE of: gelonin (column No. 1 from left); protein markers (column No. 2); and purified TAT-Gel conjugates (column No. 3 and column No. 4).

Chromatograms of a heparin-column of gelonin with the TAT-Gel conjugates, and gelonin with free TAT (control) were obtained. Gelonin with free TAT does not possess much heparin-binding ability and was thus eluted at a low retention time (i.e., low ionic strength), whereas gelonin with TAT-Gel conjugate displayed significantly longer retention times on the heparin-column due to its highly cationic nature. The TAT-Gel conjugate was eluted at an ionic strength in-between those of gelonin and TAT, indicating a successful coupling of TAT to gelonin. FIG. 6C shows an SDS-PAGE picture of the results. The TAT-Gel conjugates (the two gels on the right) displayed a protein band that is slightly higher than that of gelonin (the gel on the left), further suggesting conjugation of TAT to gelonin. Moreover, data from MALDI-MS analysis yielded MWs of 29,417 and 31,557 Da for gelonin and TAT-Gel, respectively, thus indicating the successful linkage of TAT and gelonin molecules in a 1:1 ratio.

2. In vitro Studies of TAT-Gelonin Conjugates

Figure 7A:
FIGS. 7A-7D show the cellular uptake of TAT and TAT-Gel conjugates into MCF-7 cells. The left two panels provide confocol microphotograph sections of DIC image and corresponding fluorescent images, whereas right panels show FACS results (ordinate, number of cells, abcissa, fluorescent intensity). Cells were treated with FITC-labeled gelonin (FIG. 7A); TAT-Gel (FIG. 7B); TAT-Gel+heparin (FIG. 7C); and TAT-Gel+heparin and then+protamine (FIG. 7D). Protein concentration was adjusted to 10 nM, and the incubation time was 1 hr at 37° C.
Figure 7B:
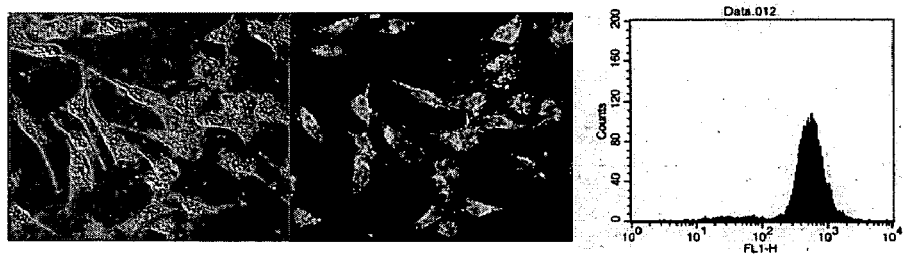
Figure 7C:
Figure 7D:

In certain embodiments, the TAT-mediated cell internalization and the cytotoxicity of TAT-Gel were examined in vitro in MCF-7 and CT-26 cell cultures. The membrane-transducing ability of the TAT-Gel conjugates was determined using fluorescence (FITC)-labeled gelonin or TAT-Gel added to the culture media of MCF-7 cells, followed by analysis by both the fluorescence activated cell sorting (FACS) and confocol microscopy. Both confocol and FACS data indicated that there was virtually no cellular uptake of free gelonin (FIG. 7A). On the other hand, almost all of the FITC labels were found inside, and specifically inside the cytosol (see confocal results), of all (~100%) cells (see the FACS data) within one hour of incubation of the cells with the TAT-Gel conjugates (FIG. 7B). Considering the fact that gelonin exerts its cytotoxic activity via binding with ribosomes and cleaving RNA, this cytosolic localization actually yields beneficial therapeutic affects. FIG. 7C shows that adding heparin to the TAT-Gel conjugates completely inhibited the cellular uptake of the conjugates. This effect was likely due to heparin binding TAT such that TAT-mediated gelonin cell adsorption and internalization was prohibited. While the present invention is not limited to any particular mechanism, this hypothesis is consistent with reports (See e.g., T. Suzuki et al., J. Biol. Chem., 277:2437-2443 [2002]; and D. A. Mann D A and A. D. Frankel, EMBO J., 10:1733-1739 [1991]) that TAT binds to the cell surface, probably via heparan sulfate, to mediated cell internalization. The addition of protamine to the heparin-inhibited TAT-Gel conjugates completely reversed the heparin-induced TAT inhibition of TAT activity. The confocol and FACS data shown in FIG. 7D show that the TAT-Gel conjugates when subsequently treated with heparin and protamine resembles the data observed in FIG. 7B when neither heparin or protamine were added to the TAT-Gel conjugates.

3. Cytotoxicity of TAT-Gelonin Conjugates

Figure 8:
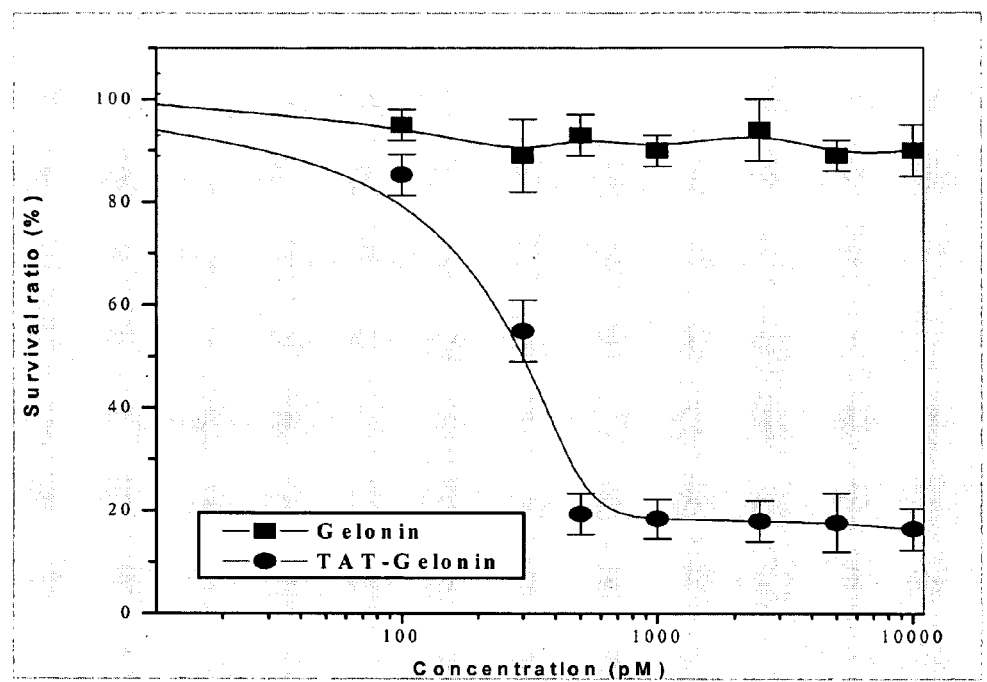
FIG. 8 shows a study of cytotoxicity of gelonin (■); and TAT-Gel conjugates (●) against CT-26 murine adenocarcinoma colon cancer cells in log-phase culture. Various doses of each test compound were added to 96-well culture plates containing approximately 5,000 cells/well. The plates were incubated for 48 hrs at 37° C. under an atmosphere of 5% $CO_2$ in humidified air. Remaining cells were assessed using MTT and compared to untreated control wells. Values shown are means±standard deviation.

In additional embodiments, the cytotoxicity of gelonin and the TAT-Gel conjugates were examined in CT-26 murine adenocarcinoma colon cancer cells in log-phase culture. Gelonin alone did not display any detectable inhibition on cell growth (FIG. 8), primarily, because it could not internalize into test cells. Coadministration of TAT and gelonin did not affect cytotoxicity, thus indicating that the gelonin was still unable to cross the cell membranes even with the existence of free TAT. In contrast, the TAT-Gel conjugates were highly cytotoxic, with $IC_{50}$ values between $10^{-8}$ to $10^{-9}M$ as measured by MTT assay. These results suggest that conjugation of gelonin with TAT enabled the gelonin to effectively translocate biologically active gelonin into the CT-26 cells. The $IC_{50}$ value of the TAT-Gel conjugates was considerably lower than for gelonin-antibody immunotoxin conjugates reported by D. L. Ewton et al. (D. L. Ewton et al., Crit. Rev. Oncol. Hematol., 39:79-86 [2001]).

The present invention contemplates that the superior cytotoxicity of TAT-Gel conjugates is due to the unparalleled cell-entering ability of TAT in comparison to other methods of translocating drugs across cell membranes (antibody based drug delivery systems). Additionally, the present further contemplates that the small molecular size of TAT, when compared to antibodies, provides less steric hindrance to conjugated drug molecules (e.g., gelonin). Indeed, studies show that conjugating an antibody to a protein toxin leads to a marked decrease in the protein toxin's activity principally due to steric hindrances.

Figure 9A:
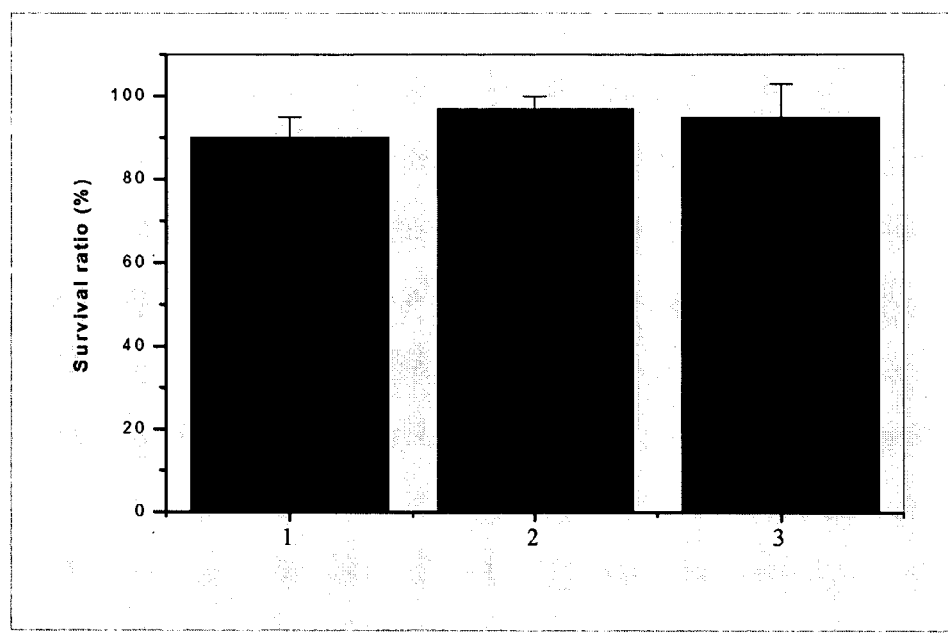
FIGS. 9A and 9B show a study of the cytotoxicity of gelonin (FIG. 9A); and TAT-Gel conjugates (FIG. 9B) against CT-26 murine adenocarcinoma colon cancer cells. Numbers on the x-axis of both figures represent: (1) gelonin (or TAT-Gel) alone; gelonin (or TAT-Gel)+heparin; and (3) gelonin (or TAT-Gel)+heparin+protamine. Cytotoxicity was measured as described in FIG. 8.
Figure 9B:
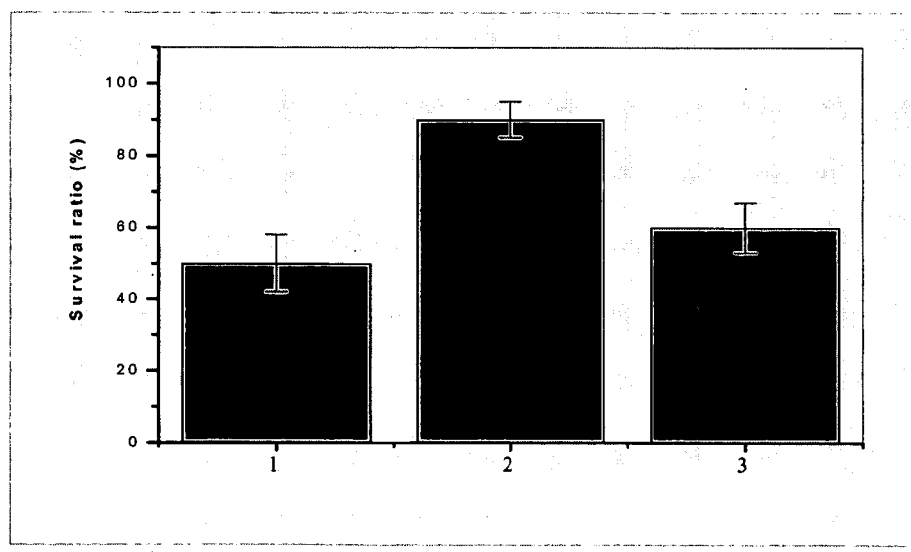

FIGS. 9A and 9B show the effects of heparin and protamine on the cytotoxicity of gelonin and TAT-Gel conjugates. Consistent with results observed above (FIG. 8), gelonin alone did not induce cell death, regardless of whether heparin or protamine was added to the culture media (FIG. 9A). Also consistent with previous results, FIG. 9B shows that TAT-Gel conjugates exhibit significant inhibitory effects on cell growth. Notably, the addition of heparin renders the TAT-Gel conjugates inactive, and the subsequent addition of protamine to the heparin-inhibited TAT-Gel conjugates almost completely reversed the cytotoxic affects of the conjugates.

In additional embodiments, the ability of the TAT-Gel conjugates to penetrate tumor tissues was tested by using rhodamine-labeled gelonin and TAT-Gel conjugates in in vivo studies as described herein.

F. PTD-RNase Conjugates

The compositions of the present invention provide PTD mediate translocation of nearly all types of therapeutic agents, drugs, and prodrugs, including many molecules previously discounted because of their poor solubility, poor cellular uptake (e.g., hydrophilic or large drugs), toxicity, poor selectivity, or other shortcomings. For example, the inability of RNase to enter cells and its lack of selectivity severely hinders the possibility of using RNase as a clinical drug. However, RNase is highly potent in damaging RNA and inducing apoptosis. Indeed, the appeal of RNA as a drug target was recognized through investigation of RNase as a potential antitumor agent. (See e.g., D. L. Ewton et al., Crit. Rev. Oncol. Hematol., 39:79-86, [2001]).

In some of embodiments, the present invention provides compositions and methods that overcome the toxicity shortfalls of RNase and thus enable RNase to be administered as a clinically effective drug. In some of these embodiments, the present invention provides therapeutic PDT-RNase conjugates that target and delivery RNase to cells and tissues interest (e.g., cancer cells).

In preferred embodiments, TAT was conjugated to RNase on a 1:1 molar basis according to the procedures described for the production of TAT-Gel conjugates. These TAT-RNase conjugates were subjected to the in vitro test described above for the TAT-Gel conjugates. The results of these tests were similar to those seen for TAT-Gel conjugates. Moreover, nearly identical in vivo results as seen in the TAT-Gel studies (See, FIGS. 7A and 7B) were observed in TAT-RNase conjugate studies.

Figure 11A:
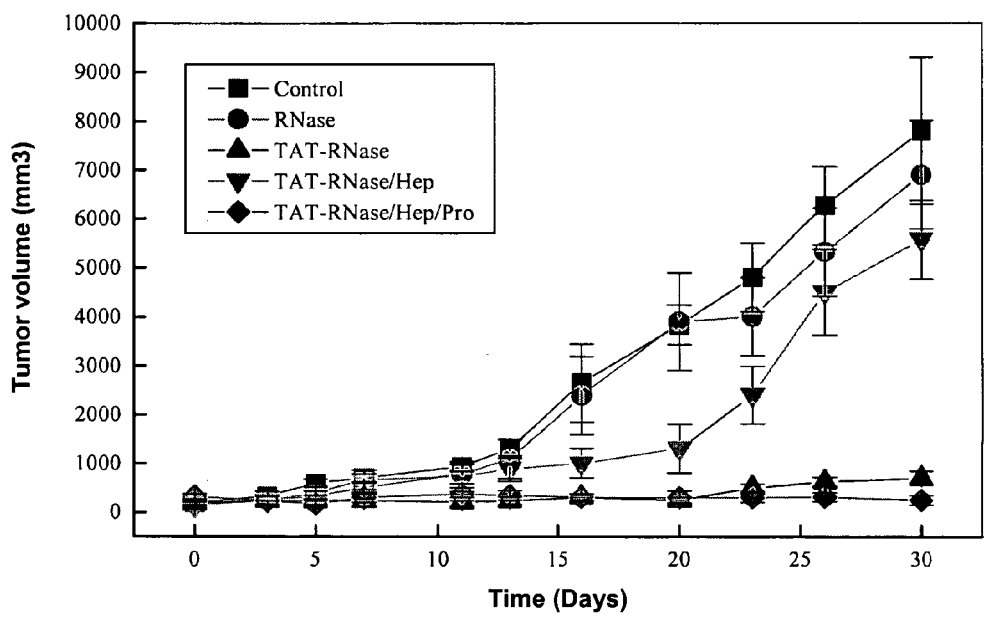
FIG. 11A shows the cytotoxic effects of: PBS (control) (■); 300 μg of RNase (●); 350 μg of TAT-RNase conjugates (equivalent to 300 Ig of RNase) (A); 350 μg TAT-RNase conjugates+80 μg heparin (▼); and 350 μg TAT-RNase conjugates+80 μg heparin+240 μg protamine (♦).
Figure 11B:
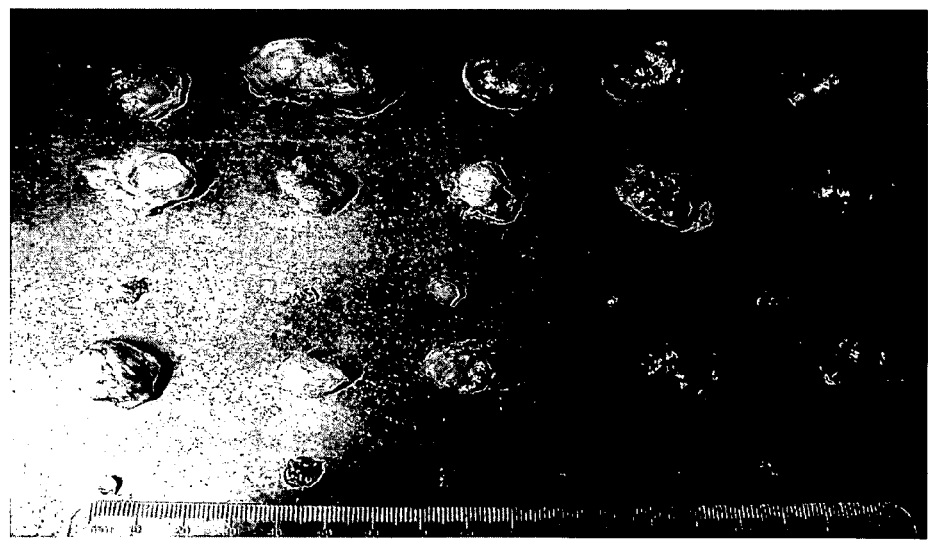
FIG. 11B shows excised tumors from treated mice. Top-to-bottom.

Notably, the administration of RNase alone does not result in detectable tumor regression. For example, in test animals an average tumor weight of 2.92±0.47 g (N=5) was observed 4 weeks after treatment (Lane 4; FIG. 11B) that was statistically indistinguishable from the value of 3.16±0.65 g (Lane 2 in FIG. 11B) of the control group without treatment. On the contrary, mice treated with TAT-RNase conjugates displayed a significant regression in tumor growth, with tumor weights being reduced to an insignificant value of 0.18±0.08 g (Lane 3; FIG. 11B). The addition of heparin to the TAT-RNase conjugate solution prior to its injection completely inhibited TAT-mediated RNase uptake, as the average tumor mass (2.77±0.63 g; N=5) from animals 4 weeks after treatment (Lane 4) was statistically indistinguishable to that (2.92±0.47 g; N=5) of mice treated with RNase alone (Lane 2). The addition of protamine to the heparin-inhibited TAT-RNase conjugates completely reversed inhibition and tumor growth was regressed to an insignificant weight of 0.09±0.05 g (Lane 5; FIG. 11B).

G. TAT-Doxorubicin Conjugates

Preferred embodiments of the present invention provide compositions and methods that combat the resistance developed by many types of tumors to various chemotherapies.

Resistance to anticancer drugs is one of the major reasons for clinical failure of cancer chemotherapies. Nearly 50% of human cancers are either completely resistant to chemotherapy or respond only transiently, after which they are no longer affected by commonly used anticancer drugs. Even more problematic is the fact that tumor cells often become resistant to a variety of structurally unrelated drugs after exposure to only one single drug. This phenomenon is referred to as multidrug resistance (MDR). (See e.g., M. M. Gottesman et al., Nature Reviews Cancer, 2:48-58 [2002]). The most well characterized mechanism leading to decreased intracellular drug levels and MDR is the overexpression of energy-dependent drug efflux pump proteins such as P-glycoprotein (Pgp) that are product of the MDR1-gene. This integral membrane protein is able to remove drugs from the cytoplasm and thus reduce intracellular drug concentrations. Pgp is also highly expressed on the luminal side of the endothelial cells and is partially responsible for the drug resistance of the blood-brain barrier (BBB).

The present invention provides PTD (e.g., TAT) based drug delivery compositions that make the Pgp peptide behave as a drug influx pump, especially as to translocating drugs across the BBB (S. R. Schwarze and S. F. Dowdy, Trends Pharmacol., 21:45-48 [2000]). Thus preferred embodiments of the present invention are able to overcome the MDR inducing effects seen in many anticancer drugs. For example, certain embodiments of the present invention provide TAT-doxorubicin conjugates that validate the ability of the PTD-based drug delivery compositions of to overcome MDR in the treatment of tumors. Doxorubicin (Dox), unlike other protein drugs described above (e.g., gelonin and RNase), is a small hydrophobic drug with a high cellular uptake. Importantly, this is a quality that makes Doxorubicin an ideal candidate to validate the ability to PTD based drug delivery systems to overcome MDR.

1. Preparation of TAT-Doxorubicin Conjugates

In some embodiments, doxorubicin was coupled to the cysteine residue of a TAT peptide synthesized using SMCC (succinimidyl 4-N-maleimidomethylcyclohexane-1-carboxylate as the crosslinking agent. The Dox-TAT conjugates were purified by HPLC using a heparin column. Results from SDS-PAGE and mass spectrometry confirmed that the Dox-TAT conjugates contained a 1:1 molar ratio of Dox:TAT.

2. In vitro Studies of TAT-Doxorubicin Conjugates

In some embodiments, monolayer doxorubicin sensitive (MCF7) and resistant (MCF7/ADR) cells were then exposed to either doxorubicin or TAT-Dox conjugates at various concentrations (up to 100 μM) for 48 hrs in the presence or absence of 10 μM verapamil. Cell viability was measured by MTT assay. As shown in Table 1, doxorubicin and TAT-Dox conjugates displayed almost identical cytotoxicity towards MCF7 cells. This indicates that conjugation of doxorubicin to TAT did not cause significant loss of doxorubicin activity. As for the MCF7/MDR cells, the TAT-Dox conjugates exhibited a remarkably higher potency than doxorubicin alone in inhibiting cell growth and the $IC_{50}$ value of free doxorubicin was almost 8-fold higher than that of Dox-TAT conjugates. Results from fluorescence microscopy are consistent with this finding and show that while only a negligible amount of doxorubicin was seen in Dox-treated MDR cells, a significant amount of labeled doxorubicin was found in TAT-Dox treated MDR cells. Verapamil, a P-glycoprotein inhibitor, was able to restore most of the cytotoxic activities of free doxorubicin. However, Verapamil failed to induce an increase in cellular accumulation of the TAT-Dox conjugates (Table 1). These finding suggests that PTDs such as TAT can protect drugs from P-glycoprotein-mediated MDR effects.

TABLE 1

Comparison of $IC_{50}$ (μM) cytotoxicity between free doxorubicin (Dox) and doxorubicin-TAT conjugates (TAT-Dox)

|  | Dox | Dox-TAT | Verapamil (10 μM) Dox | Verapamil (10 μM) Dox-TAT |
|---|---|---|---|---|
| MCF7 | 0.25 | 0.28 | ND | ND |
| MCF7/ADR | 45.2 | 5.8 | 6.7 | 5.2 |

The present invention shows that the cell-translocating activity of the PTD (e.g., TAT) based drug delivery compositions can offset the efflux-pumping activity of Pgp resulting in reduced MDR effects towards PTD-linked drugs. The PTD based drug delivery compositions of the present invention are effective at reducing occurrence of MDR.

H. LMWP Based Conjugates

Figure 12:
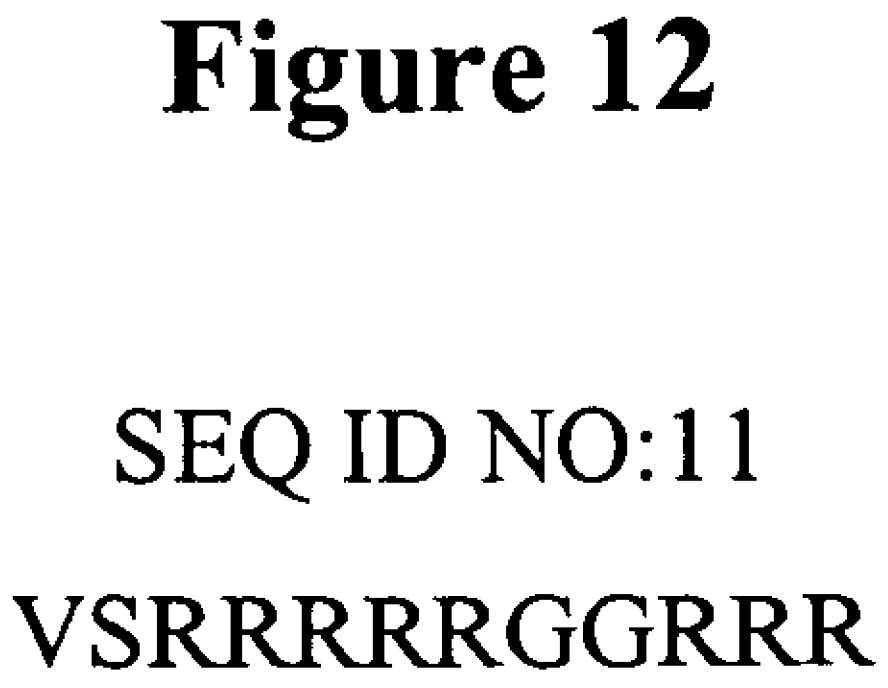

In some embodiments, the PTDs used in the drug delivery compositions of the present invention to mediate the translocating of therapeutic molecules (e.g., anticancer drugs) comprise one or more low molecule weight protamine (LMWP) peptides derived from protamine. In some embodiments, LMWPs comprise non-toxic peptides that contain a highly basic amino acid composition similar to other PTDs. More particularly, in some preferred embodiments, the LMWP peptides have an amino acid sequences from about 20 to over 99% similar to at least a portion of the TAT (YGRKKRRQRRR) (SEQ ID NO:6) protein. For example, in one embodiment the LMWP protamine derived peptide comprises the sequence VSRRRRRGGRRR (SEQ ID NO:11) (See, FIG. 12). Other LMWP protamine derived peptides and methods used to isolate and manufacture LMWP peptides are known in the art. (See e.g., L. C. Chang et al., AAPS PharmSci., 3(2) Article 17 [2001]; L. C. Chang et al., AAPS PharmSci. 3(2) Article 18 [2001]; and L.M. Lee et al., AAPS PharmSci. 3(2) Article 19 [2001]).

1. Cell-Translocation Functions of LMWP

Figure 13:
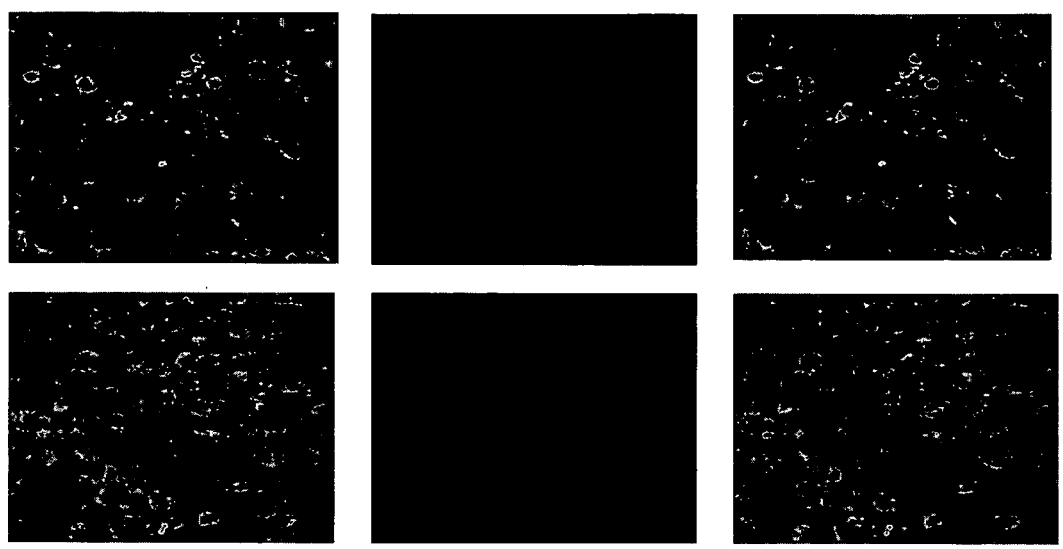
FIG. 13 shows the translocation of LMWP (upper panel) and TAT (lower panel) through a cell membrane of MCF-7 cells after 15 min incubation with FITC-labeled peptides.

In some embodiments, purified LMWP was prepared according to the method described in L.C. Chang et al., AAPS PharmSci., 3(2) Article 17 [2001]. In some additional embodiments, cell internalization characteristics of TAT and LMWP were compared by confocol microscopy using FITC-labeled peptides. Like TAT, after 15 min of incubation with MCF-7 cells at 37° C., more than 70% of the FITC-labeled LMWP entered the cytosol of the MCF-7 cells (FIG. 13). Unlike TAT, which primarily localizes in the nucleus after 30 min incubation with the MCF-7 cells, LMWP mainly localizes in the cytoplasm. The reason for the difference in cell localization remains unclear, however, while the present invention is not limited to any particular mechanism, it is contemplated that TAT, which contains the sequence of the nuclear localization signal (NLS) peptide, can penetrate into the cell's nucleus either through pores on the nuclear envelope, or via binding with certain cytoplasmic components which confer nuclear localization. (L. Chaloin et al., Biochem. Biophys. Res. Commun., 243:601-608 [1998]; and M. A. Zanta M A et al., Proc. Natl. Acad. Sci. USA, 96:91-96 [1999]). In some embodiments, the localization of TAT and TAT-like peptides can be directed to the cytoplasm or to other sites within the cell by making altering portions of its amino acid sequence. (See e.g., M. M. Gottesman et al., Nature Reviews Cancer, 2:48-58 [2002]). In some preferred embodiments, the sequence of the PTD component/subcomponent of the drug delivery composition is selected or modified (e.g., amino acid sequence altered) so that the composition and the therapeutic molecule(s) being carried are localized to the cytoplasm. The present invention contemplates that in certain embodiments the localization of the drug delivery compositions to the cytoplasm aids in the penetration of the therapeutic molecules throughout the targeted tissue (e.g., from the tumor periphery to the tumor core).

2. Kinetics of LMWP-Conjugate Cell Internalization

Figure 14:
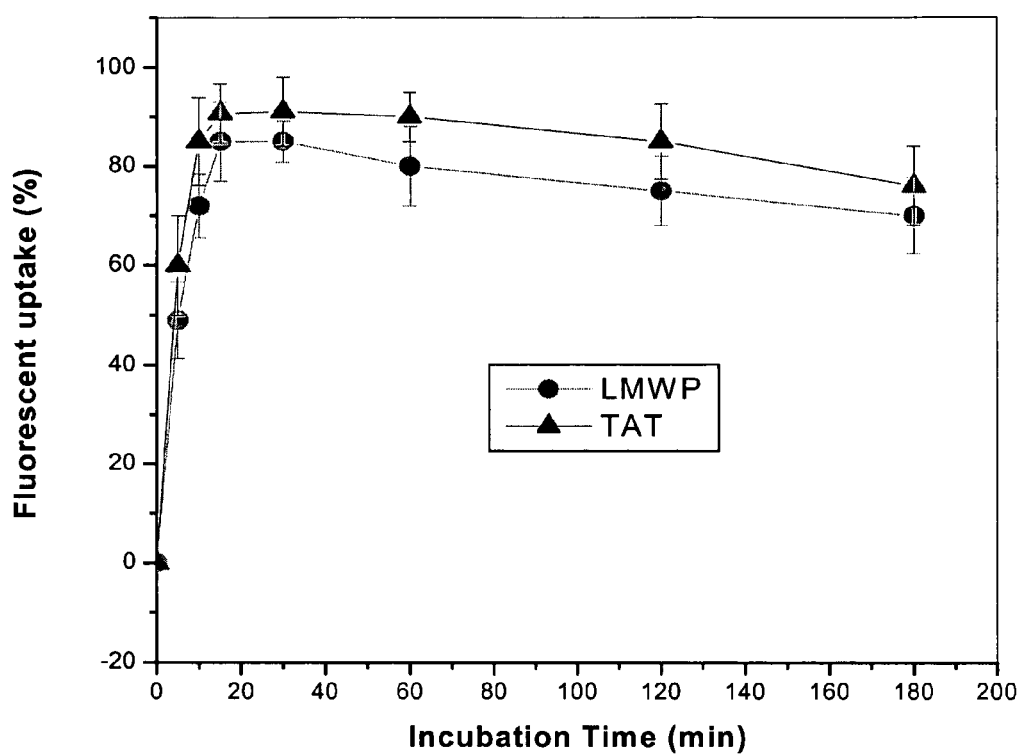
FIG. 14 shows the kinetics of cellular uptake of FITC-labeled LMWP and TAT in MCF-7 cell lines. Cells were incubated with the FITC-labeled peptides and then lysed. Fluorescence intensities in the supernatants were measured.

FIG. 14 provides a comparison of the rate of cellular uptake of LMWP and TAT. As shown, TAT displayed a slightly faster cellular uptake than LMWP, although the difference was nearly statically insignificant. The concentrations of both TAT and LMWP reached a maximum after 30 min of incubation with the MCF-7 cells, followed by a gradual decrease of the FITC intensity for both peptides.

3. LMWP Conjugate Capability in Translocating Gelonin

Figure 15A:
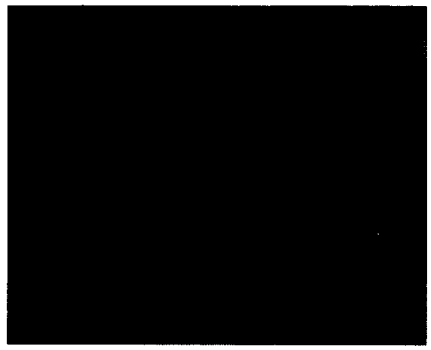
FIGS. 15A and 15B show the translocation of gelonin into the CT-26 cells with the aid of: TAT (FIG. 15A); or LMWP (FIG. 15B). Fluorescent microscopy was conducted on cells treated with rhodamine-labeled TAT- or LMWP-gelonin following 2 hrs of incubation in CT-26 cells.
Figure 15B:
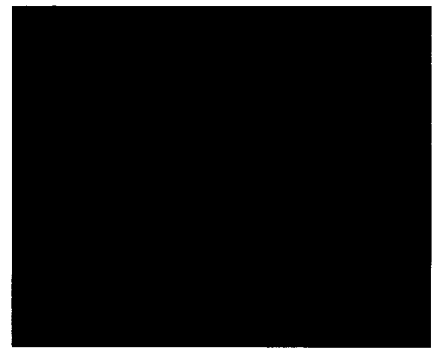

In some embodiments, studies were preformed to compare the capabilities of LMWP and TAT in protein translocation. In some of these embodiments, the LMWP and TAT peptides were conjugated to gelonin using the PDPH method described herein. To create a -SH group for coupling, LMWP was modified prior to its conjugation by treatment with SPDP and DTT, using the protocol established by J. Carlsson et al., (J. Carlsson et al., Biochem. J., 173:723-737 [1978]). Gelonin was labeled with rhodamine prior to conjugation. As seen in FIGS. 15A and 15B, both LMWP and TAT were capable of translocating gelonin, as rhodamine labels were clearly detected in both cases after 2 hrs of incubation with the CT-26 cells. Confocol microscopic analysis revealed a cytoplasmic localization not just attachment to the cellular membrane of the LMWP-gelonin conjugates.

4. LMWP-Mediated Gelonin Cytotoxicity

Figure 16:
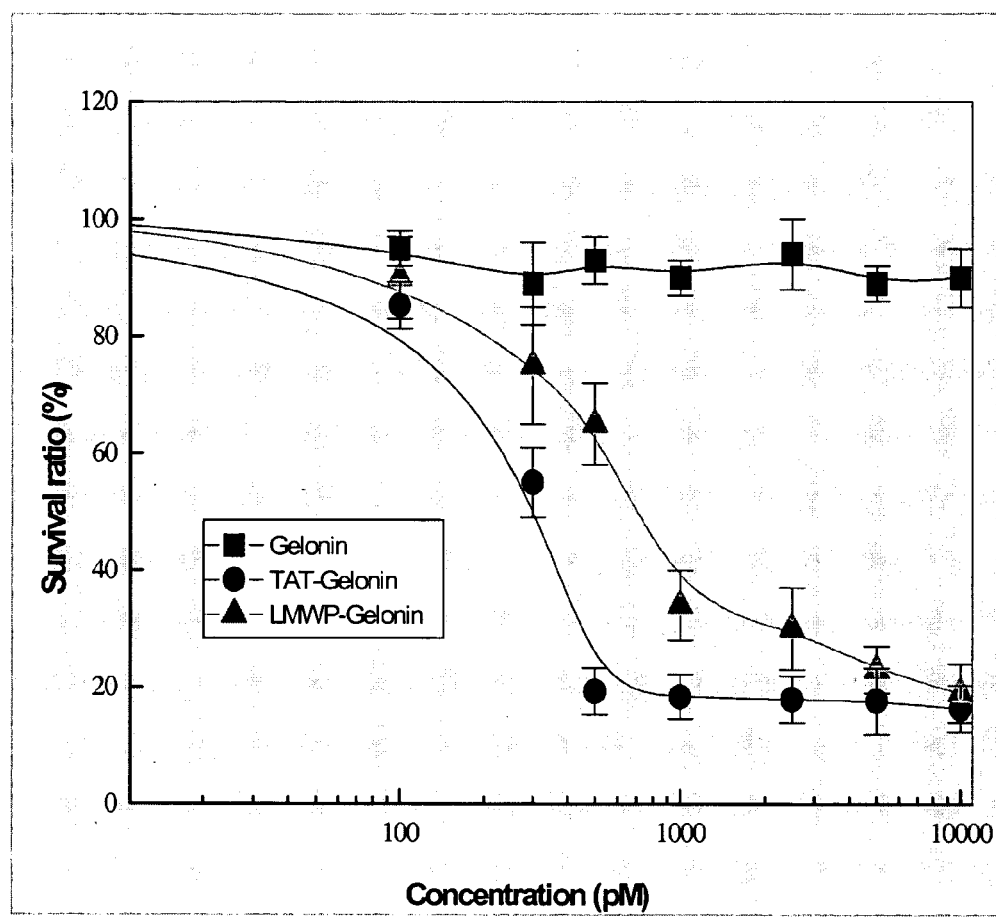
FIG. 16 shows the cytotoxicity of native gelonin (■); TAT-Gel conjugates (●); and LMWP-Gel conjugates (▲) against CT-26 murine adenocarcinoma colon cancer cells in log-phase culture. Various doses of each compound were added to 96-well culture plates containing approximately 5,000 cells/well. The plates were incubated for 48 hrs at 37° C. under an atmosphere of 5% $CO_2$ in humidified air in an incubator. Test cells were assessed by MTT assay and then compared to untreated cells in control wells. Values are represented as means±standard deviation. Each experiment was performed in triplicate.

As shown in FIG. 16, similar to that TAT-Gel conjugates, the LMWP-Gel conjugates successfully delivered gelonin to test cells. Although TAT-Gel conjugates seem to have a slightly lower $IC_{50}$ value than that of LMWP-Gel, the difference was rather insignificant and could possibly be attributable to inconsistencies in measurements in the cell culture medium.

V. Pharmaceutical Compositions

The present invention provides novel compositions and methods for treating a number of diseases in animals, preferably in mammalians, and even more preferably in humans. In preferred embodiments, the pharmaceutical compositions of the present invention comprise the two component drug delivery compositions described herein having one or more therapeutic agents, drugs, or prodrugs conjugated thereto. In some of these embodiments, the drug delivery compositions comprise common pharmaceutical carriers, including any sterile biocompatible pharmaceutical carrier (e.g., saline, buffered saline, dextrose, water, and the like). Accordingly, in some embodiments, the methods of the present invention comprise administering the compositions of the present invention in a suitable pharmaceutical carrier.

In some embodiments, the pharmaceutical formulations of the present invention comprise a mixture of two or more different formulations of drug delivery compositions. Different formulations of drug delivery compositions may comprises respective drug delivery compositions having one or more dissimilar molecular recognition elements and/or one or more therapeutic agents, drugs, or prodrugs being carried thereon.

In still further embodiments, the pharmaceutical compositions comprise a plurality of drug delivery compositions administered to a subject under one or more of the following conditions: at different periodicities, different durations, different concentrations, different administration routes, etc.

In some preferred embodiments, the compositions and methods of the present invention find use in treating diseases or altered physiological states characterized by pathogenic infection. However, the present invention is not limited to ameliorating (e.g., treating) infections. Indeed, various embodiments of the present invention are directed to treating a range of physiological symptoms and disease etiologies in subjects generally characterized by aberrant cellular growth or proliferation (e.g., cancer), autoimmunity (e.g., rheumatoid arthritis), and other aberrant biochemical, genetic, and physiological diseases and conditions.

Depending on the condition being treated, these pharmaceutical compositions are formulated and administered systemically or locally. Techniques for formulation and administration are found in the latest edition of "Remington's Pharmaceutical Sciences" (Mack Publishing Co, Easton Pa.). Accordingly, the present invention contemplates administering pharmaceutical compositions in accordance with acceptable pharmaceutical delivery methods and preparation techniques. For example, some compounds of the present invention are administered to a subject intravenously in a pharmaceutically acceptable carrier such as physiological saline. For injection, the pharmaceutical compositions of the invention are formulated in aqueous solutions, preferably in physiologically compatible buffers (e.g., Hanks' solution, Ringer's solution, or physiologically buffered saline). For tissue or cellular administration, penetrants appropriate to the particular barrier to be permeated are preferably used in the formulations. Such penetrants are generally known in the art. Standard methods for intracellular delivery of pharmaceutical agents are used in other embodiments (e.g., delivery via liposomes). Such methods are well known to those skilled in the art.

In some embodiments, present compositions are formulated for parenteral administration, including intravenous, subcutaneous, intramuscular, and intraperitoneal. In some embodiments, these compositions optionally include aqueous solutions (i.e., water-soluble forms). Additionally, suspensions of the active compounds may also be prepared as oily injection suspensions as appropriate. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Therapeutic coadministration of some contemplated compositions is also accomplished using gene therapy techniques described herein and commonly known in the art.

In other embodiments, the present compositions are formulated using pharmaceutically acceptable carriers and in suitable dosages for oral administration. Such carriers enable the compositions to be formulated as tablets, pills, capsules, dragees, liquids, gels, syrups, slurries, suspensions and the like, for oral or nasal ingestion by a patient to be treated.

Pharmaceutical preparations for oral use can be obtained by combining the active compounds (e.g., drug delivery compositions) with a solid excipient, optionally grinding the resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as cross-linked polyvinyl pyrrolidone, agar, alginic acid or a salt thereof such as sodium alginate.

Ingestible formulations of the present compositions may further include any material approved by the United States Department of Agriculture for inclusion in foodstuffs and substances that are generally recognized as safe (GRAS) such as, food additives, flavorings, colorings, vitamins, minerals, and phytonutrients. The term "phytonutrients" as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to tablets or dragee coatings for product identification or to characterize the quantity of active compound, (i.e., dosage).

Compositions of the present invention that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments of the present invention, the drug delivery compositions are administered to a patient alone or in combination with one or more other drugs or therapies (e.g., antibiotics and antiviral agents etc) or in pharmaceutical compositions where they are mixed with excipient(s) or other pharmaceutically acceptable carriers.

In some embodiments, pharmaceutically acceptable carriers are preferably pharmaceutically inert.

Pharmaceutical compositions suitable for use in the present invention further include compositions wherein the active ingredients are contained in an effective amount to achieve the intended purpose. For example, an effective amount of therapeutic compound(s) may be that amount that destroys or disables pathogens as compared to control pathogens.

In some embodiments, the pharmaceutical compositions used in the methods of the present invention are manufactured according to well-known and standard pharmaceutical manufacturing techniques (e.g., by means of conventional mixing, dissolving, granulating, dragee-making, levigating, emulsifying, encapsulating, entrapping or lyophilizing processes).

Dosing is dependent on severity and responsiveness of the disease state to be treated, with the course of treatment lasting from several days to several months, or until a cure is effected or a diminution of the disease state is achieved. Optimal dosing schedules are calculated from measurements of composition accumulation in the subject's body. The administering physician can easily determine optimum dosages, dosing methodologies and repetition rates. Optimum dosages may vary depending on the relative potency of compositions agents, and can generally be estimated based on the $EC_{50}$ values found to be effective in in vitro and in vivo animal models. Additional factors that may be taken into account, include the severity of the disease state; the age, weight, and gender of the subject; the subject's diet; the time and frequency of administration; composition combination(s); possible subject reaction sensitivities; and the subject's tolerance/response to treatments. In general, dosage is from 0.001 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the therapeutic agent is administered in maintenance doses, ranging from 0.001 µg to 100 g per kg of body weight, once or more daily, weekly, or other period.

For any compound used in the methods of the invention, the therapeutically effective dose can be estimated initially from cell culture assays. Then, preferably, dosage can be formulated in animal models (particularly murine or rat models) to achieve a desirable circulating concentration range that results in increased PKA activity in cells/tissues characterized by undesirable cell migration, angiogenesis, cell migration, cell adhesion, and/or cell survival. A therapeutically effective dose refers to that amount of compound(s) that ameliorate symptoms of the disease state (e.g., pathogenic infection). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from cell culture assays and additional animal studies can be used in formulating a range of dosage, for example, mammalian use (e.g., humans). The dosage of such compounds lies preferably, however the present invention is not limited to this range, within a range of circulating concentrations that include the $ED_{50}$ with little or no toxicity.

Guidance as to particular dosages and methods of delivery is provided in the literature (See, U.S. Pat. Nos. 4,657,760; 5,206,344; or 5,225,212, all of which are herein incorporated by reference in their entireties). Administration of some agents to a patient's bone marrow may necessitate delivery in a manner different from intravenous injections.

EXAMPLES

The present invention provides the following non-limiting examples to further describe certain contemplated embodiments of the present invention.

Example 1

General Experimental Design Considerations

The experiments described herein were designed to demonstrate the abilities of the present compositions to specifically target. and effectively deliver (e.g., translocate therapeutic molecules) across the cell membranes in a variety of cell and tissue types.

1. Model Tumor Systems

In preferred embodiments, an initial consideration in designing specific drug delivery compositions and accompanying validating experiments is the type of aberrant cells and tissues (e.g., diseased cells, and especially tumor cells) sought to be treated. For example, in some embodiments directed to providing drug delivery systems for treating (e.g., targeting and delivering therapeutic agents to cancer cells) cancerous cells and tissues, the present invention provides treatment models for both solid and diffuse tumors.

Testing the inventive compositions in two markedly different tumor types (i.e., solid and diffuse) provides insights into the feasibility of the delivery approach over a broad range of tumor treatments.

Solid tumors, including the prevalent carcinomas, make up more than 90% of all human cancer types. (T. R. Shockley et al., Ann. NY Acad. Sci., 617:367-382 [1991]). Effective drug delivery systems for treating solid tumors are thus of considerable therapeutic value. In some embodiments, CT-26 murine adenocarcinoma colon cancer cells are used to provide a model system of solid type tumors. In preferred embodiments, CT-26 murine adenocarcinoma colon cancer cells are injected subcutaneously into BALB/c mice to create a solid tumor type model. Likewise, finding effective treatments for soft tissue malignant tumors, which are diffuse, non-localized, or highly recurrent, remains a significant challenge in the field of cancer therapy. (T. R. Shockley et al., supra). It is therefore also of great interest to find effective treatments (e.g., drug delivery systems) for diffuse type of tumors. In preferred embodiments, the present invention provides B-cell lymphoma Raji cells as a model for system diffuse lymphoma tumors.

2. Exemplary Drug Types

Another important consideration when designing and fabricating the present drug delivery systems is the class, and more specifically the particular drug(s), chosen for transport and delivery. Two important classes of drugs contemplated for delivery by the compositions and methods of the present invention are conventional small hydrophobic anticancer drugs (e.g., doxorubicin) and macromolecular hydrophilic protein toxins (e.g., gelonin). The present invention is not limited however, to compositions and methods for targeting and delivery the above-mentioned classes of drugs and therapeutic agents or to delivering Doxorubicin and Gelonin.

In some embodiments, doxorubicin (Dox; MW: 560 Da) was selected to represent the class of small hydrophobic drugs whose therapeutic functions are governed less by their cell-entering ability but more by their poor solubility and bioavailability. Conjugation of this type of hydrophobic drugs with highly hydrophilic PTDs (e.g., TAT, TAT-like peptides, LMWP etc) enhances their solubility and bioavailability. In additional embodiments, the ability of hydrophobic doxorubicin to diffuse across cell membranes provides an ideal candidate drug for examining potential MDR developed towards PTD-based drug delivery conjugates. In still other additional embodiments, the small molecular nature of doxorubicin makes it an excellent candidate for demonstrating the capability of the polyrotaxane subcomponents of the drug delivery systems to effectively deliver large doses of particular drugs.

In other embodiments, gelonin (MW: 30 kDa) provides an exemplary of the class of hydrophilic macromolecular protein drugs. Gelonin belongs to the family of ribosome-inactivating proteins (RIPs) that inhibit protein synthesis by cleaving mRNAs. (M. Wu, Brit. J. Cancer, 75:1347-1355 [1997]). Thus, embodiments of the present invention that target and delivery gelonin to target cells (e.g., cancer cells) establish the applicability of the present compositions to deliver both protein and enzyme drugs. Still other embodiments provided chimeric fusion toxins for targeting the neovasculature of solid tumors (See e.g., L. M. Veenendaal et al., Proc. Natl. Acad. Sci. USA, 99:7866-7871 [2002]) comprising gelonin conjugates and molecular recognition elements (e.g., vascular endothelial growth factor [VEGF], antibodies, glycoproteins, etc).

3. Solid Tumor: Vascular Targeting ($VEGF_{121}$)

The dense packing of epithelial tumor cells and the fibrous tumor stroma present a formidable physical barrier to macromolecular transport. In addition, the absence of an efficient lymphatic drainage in most solid tumors results in elevated interstitial pressure in tumor core. (R. K. Jain et al., Cancer Res., 47:3039-3051 [1987]). In conventional antibody-mediated tumor penetration methods in humans, typically only 0.001-0.01% of the injected antibody dose localizes to each gram of solid. (See, H. Sands, Antibody Immunoconjugates and Radiopharm., 1:213-226 [1988]).

In some embodiments, vascular targeting provides selective delivery of therapeutic agents to the tumor neovasculature. Indeed, vascular targeting provides an effective avenue for overcoming typical limitations on delivering drugs to solid tumors (See e.g., U. Niesner et al., Bioconjugate Chem., 13:729-736 [2002]; P. E. Thorpe et al., Breast Cancer Res. Treatment, 36:237-251 [1995]; and P.E. Thrope and S. Ran: Targeting clotting factors to tumor vasculature. In: Proceedings of the International Symposium on Tumor Targeted Delivery System, pp. 1-4, [Sep. 25-27, 2000]). In some preferred embodiments directed to treating tumors, the compositions of the present invention provide vascular endothelial growth factor (VEGF) as the molecular recognition element for targeting solid tumors.

VEGF plays an important role in tumor angiogenesis. It binds to tyrosine kinase receptors, that are expressed almost exclusively on tumor endothelium. VEGF has been used in targeting toxin molecules to tumor vessels in anti-angiogenic therapies. However, recent studies indicated that VEGF also binds to an isoform of the neurophilin-1 (NP-1) receptor, which is widely expressed in normal tissues. Thus, existing VEGF-based drug delivery systems present a risk for developing toxic effects in untargeted cells. In contrast, the analogue $VEGF_{121}$, which lacks the binding domain to NP-1 receptor, avoids evoking toxic side effects in normal endothelium. Accordingly, in some preferred embodiments of the present invention directed to treating solid tumors, the present drug delivery compositions comprise $VEGF_{121}$ as a molecular recognition element.

In general, vascular targeting provides several advantages over other tumor targeting methods. For example, with vascular targeting, vascular endothelial cells are directly accessible to intravenously administered therapeutic agents. Tumor cells rely on blood vessels for their supply of nutrients and oxygen to satisfy their metabolic needs and thus the tumor tissues must establish vascularization to survive. Furthermore, studies estimate that typically 100 or more tumor cells rely on one endothelial cell for survival. Therefore, in preferred embodiments, vascular targeting can deliver anti-tumor agent to a large number of tumor cells. In addition, vascular delivery of antitumor agents provides a dual therapeutic effect, as damage of vascular endothelial cells has been shown to cause tumor cell death. (P. E. Thorpe et al., Breast Cancer Res. Treatment, 36:237-251 [1995]). One additional advantage of vascular targeting is that angiogenesis is common in aggressive solid tumors, thus vascular targeting agents should be effective on many different types of solid tumors. Moreover, vascular targeting retains the benefits of the EPR affect (H. Maeda et al., J. Controlled Release, 65:271-284 [2000]) in tumor vasculature.

4. Diffuse Tumor: Antibody Targeting (Anti-CD20 Antibody (C2B8; RITUXIMAB))

In preferred embodiments, targeting of diffuse tumors is provided by using conventional antibody targeting moieties known in the art. For example, in some embodiments, the anti-CD20 antibody C2B8 (RITUXIMAB or RITUXANA) is selected to target the drug delivery compositions to diffuse types of tumors. CD20 is a nonglycosylated phosphoprotein (MW: 33-37 KDa) that is expressed on over 95% of normal and neoplastic B cells. It is expressed on the cell surface from the pre-B stage of development until terminal differentiation to plasma cells occurs, and has been used as one of the most reliable markers for the B-cell lineage. (P. A. Leland et al., J. Biol. Chem., 276(46):43095-43102 [2001]). Recent studies suggest that CD20 is a B-cell surface protein that is serves as a calcium channel, initiates intracellular signals, and modulates cell growth and differentiation. (B. R. Kelemen et al., Nucleic Acids Res., 27: 3696-3701 [1999]). The ubiquitous, high-density expression of CD20 on the surface of malignant human B cells makes it an ideal target for immunotherapy of B-cell lymphomas. (M. G. Rosenblum et al., Clin. Cancer Res., 5:865-874 [1999]). RITUXIMAB is a chimeric human/mouse monoclonal antibody with anti-CD20 specificity. This antibody has been approved for use in patients with relapsed follicular low grade non-Hodgkin's lymphoma (NHL). In addition, RITUXIMAB has been shown to increase the chemosensitivity of the CD-20 positive cells including Raji, Daudi cells, since binding CD20 and C2B8 antibody appears to start apoptosis in these cells. RITUXIMAB is also particularly effective when combined with chemotherapeutic agents because of its chemo-sensitizing activity. For example, pretargeted radioimmunotherapies (PRITTM) for the treatment of non-Hodgkin's lymphoma using C2B8 have been adopted clinically.

5. Membrane-Translocating Type Peptide (LMWP)

As discussed previously, the low molecular weight protamine (LMWP) peptide described herein provides a suitable PTD in certain embodiments of the present invention. In some of these embodiments, LMWP is nearly as potent as TAT in mediating the cellular translocation of attached species (e.g., drug molecules). Without being limited to any particular mechanism, the present invention contemplates that protein species translocated by LMWP remain in the cytosol whereas those translocated by TAT are moved to the cell's nucleus.

In preferred embodiments, LMWP mediated translocation enables therapeutic agents to enter the core of the tumor mass and to avoid being trapped in the nucleuses of cells on the tumor's periphery. Importantly, the toxicity profiles of LMWP have been fully established. Animal studies demonstrate that LMWP is neither immunogenic (J. F. Liang et al., Biochemistry (Moscow), in press, 2002) nor antigenic. (B. Tsui et al., Thromb. Res., 101:417-420 [2001]). Administering LMWP to dogs does not elicit acute hypotensive responses or other toxicities such as complement activation. (L. M. Lee et al., AAPS PharmSci., 3(2) Article 19 [2001]). Large quantities of LMWP can be produced from native protamine relatively quickly and inexpensively. Since LMWP possesses only a single —$NH_2$ group at its N-terminal end, conjugation of LMWP to proteins or drug molecules can be precisely regulated (e.g., 1:1 molar ratio between LMWP and the protein or drug) and is easily carried out using the N-succinimidyl 3-(2-pyridyldithio) propionate (SPDP) activation and thiolation method known in the art. (J. Carlsson Biochem. J., 173:723-737 [1978]).

Example 2

Characterization (LMWP-Gel)

In some embodiments, the content of doxorubicin is determined using $^1$H-NMR analysis by comparing the integration of the proton signal on the $C_4$ position of tyrosine (7.03 ppm) with that of the $C_1$ position of doxorubicin (7.80 ppm), whereas the average number of α-CD in the polyrotaxane (PR) is determined by comparing the integration of the proton signals at 4.79 ppm ($C_1$ of α-CD) with that at 3.51 ppm ($C_2$ of PEG). It is estimated that approximately 25 doxorubicin molecules can be conjugated to a single polyrotaxane molecule with a MW of ~50 kDa. Chari reported that maximum doxorubicin drug loading per antibody (MW~150 kDa) is about 8 molecules. (R. V. J. Chari, Adv. Drug Deliv. Rev., 31:89-104 [1998]). In some embodiments, the polyrotaxane-based drug delivery compositions provide enhanced drug loading over antibody-based systems by about 10 fold on a weight-to-weight basis.

Example 3

Kinetics of Doxorubicin Release from LMWP-Dox Conjugates

Doxorubicin is slowly released from the polyrotaxane chain by hydrolysis. In order to assess the dose required for in vivo studies, the kinetics of doxorubicin release from the LMWP-Dox-PR conjugates are studied in PBS solution. A typical kinetics study of in vitro drug release is conducted. In general, LWMP-Dox-PR conjugates are incubated in buffer at 37° C. At various time intervals, samples are withdrawn and chromatographed on an HPLC column. The intensity of the doxorubicin peaks at different times are then analyzed and plotted versus time.

Example 4

Synthesis of LMWP-Gel Conjugates

This example describes the chemical synthesis of certain embodiments of LMWP-Gel conjugates of the present invention. Other embodiments of the present invention use the protocol for producing fused TAT-protein chimeras using the recombinant DNA methodology described by M. Becker-Hapak et al., Methods, 24:247-256 [2001]).

In certain embodiments, LMWP is chemically linked to the carbohydrate moiety of gelonin for two major reasons: 1) this coupling strategy is contemplated to fully preserve the biological functions of gelonin, since the location of the carbohydrate chain is spatially distant from that of gelonin's active site; and 2) conjugation to the carbohydrate chain may prolong the blood clearance time for gelonin, because it masks the ligands on the carbohydrate chains from being recognized by receptors in the liver. In an in vivo study of glycoprotein-based plant toxins, Thorpe (P. E. Thorpe et al., Eur. J. Biochem., 147:197-206 [1985]) demonstrated that the recognition sites for RES are located at the carbohydrate structures of such toxins, and chemical modification of these carbohydrate chains resulted in improved tissue distribution and pharmacokinetics of plant toxins.

To prepare LMWP-Gel a conjugate, the carbohydrate chain on gelonin is activated by oxidation with sodium periodate. Following incubation at room temperature for 1 hr, PDPH, which is a heterobifunctional crosslinker that contains an oxidized carbohydrate-specific hydrazide and a pyridylthio reactive group, is added to the reaction mixture. After incubation at room temperature for 2 hr, LMWP that has already been thiolated at the N-terminal using the SPDP method is added to the PDPH-treated gelonin to produce LMWP-Gel conjugates via a disulfide bond.

Example 5

Characterization of LMWP-Gel Conjugates

The number of LMWP molecules incorporated per gelonin molecule is estimated using both MALDI-MS and SDS-PAGE analyses according to the procedures described previously for FIGS. 6A-6C and the description thereof.

Example 6

Translational Inhibition Assay

In this example, the functional activity of LMWP-Gel conjugates is assayed by the cell-free translational reticulocyte assay using the Promega (Madison, Wis.) assay kit. In brief, free gelonin (control) or LMWP-Gel is added to vials containing rabbit reticulocyte lysate reagent and luciferase, mRNA-Luc. After incubation at 37° C. for 90 min, aliquots of samples are then withdrawn and assayed for luciferase activity using procedures reported previously in S. F. Atkinson et al., J. Biol. Chem., 276 (30): 27930-27935 (2001).

Example 7

TAT-Gel Conjugate Enzyme Kinetic Assays

In this example, assays for determining the activity of gelonin on RNA cleavage using an enzyme kinetic assay using fluorogenic 6-FAM-dArU(dA)2-6-TAMRA as the substrate are conducted. Upon ribonuceolytic cleavage, the substrate should yield an increase of the fluorescent intensity by about 180 fold. (See, L. M. Veenendaal et al., Proc. Natl. Acad. Sci. USA, 99:7866-7871 [2002]).

Example 8

In vivo Studies of the TAT-Gel Conjugates

This example describes in vivo studies using CT26 colon carcinoma bearing BALB/c mice and TAT-Gel conjugates. Approximately 106 CT-26 tumor cells were implanted subcutaneously into each mouse, and drug treatments were started about 3 weeks after tumor implantation when the tumors reached about 100 mm$^3$. As there were no appropriate antibodies commercially available at the time of experiments, the targeting feature (e.g., molecular recognition element) of the drug delivery system was alternatively managed by intratumoral injections. Five test compounds were included in the animal study including: (1) PBS solution (control); (2) gelonin (100 μg); (3) TAT-Gel conjugate (100 μg gelonin equivalent); (4) TAT-Gel+heparin conjugates (20 μg); and (5) TAT-Gel+heparin conjugates (20 μg)+protamine (60 μg). Each CT-26-bearing mouse was given a total of 9 treatments; once per 2 days. Thirty days after initial treatment, mice were sacrificed and their tumors were excised and measured for weight.

1. Tumor Regression by TAT-Gel Conjugates: Effects of Heparin and Protamine

Figure 10A:
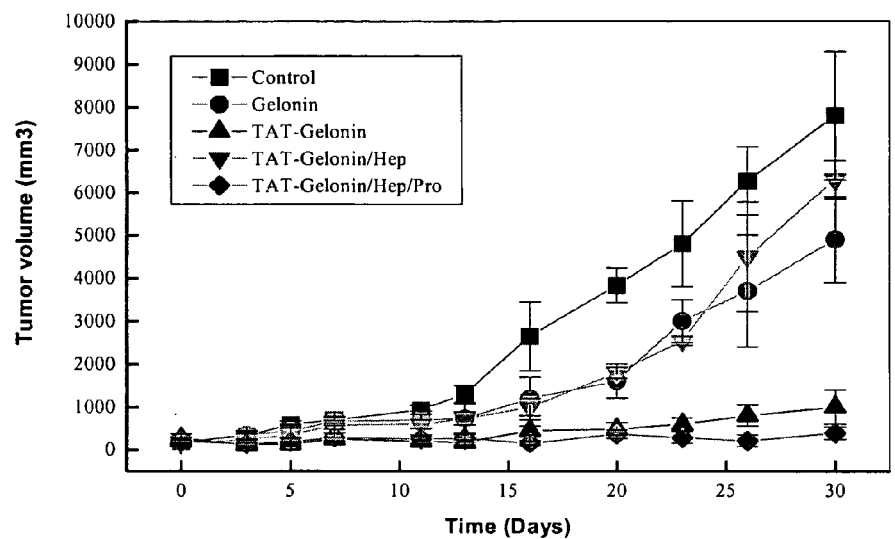
FIG. 10A shows the cytotoxic effects of: PBS (control) (■); 100 mg of gelonin (●); 110 μg of TAT-Gel conjugates (equivalent to 100 μg gelonin) (▲); 110 μg TAT-Gel conjugates+20 mg heparin (▼); and 110 μg TAT-Gel conjugates+ 20 μg heparin+60 μg protamine (♦).
Figure 10B:
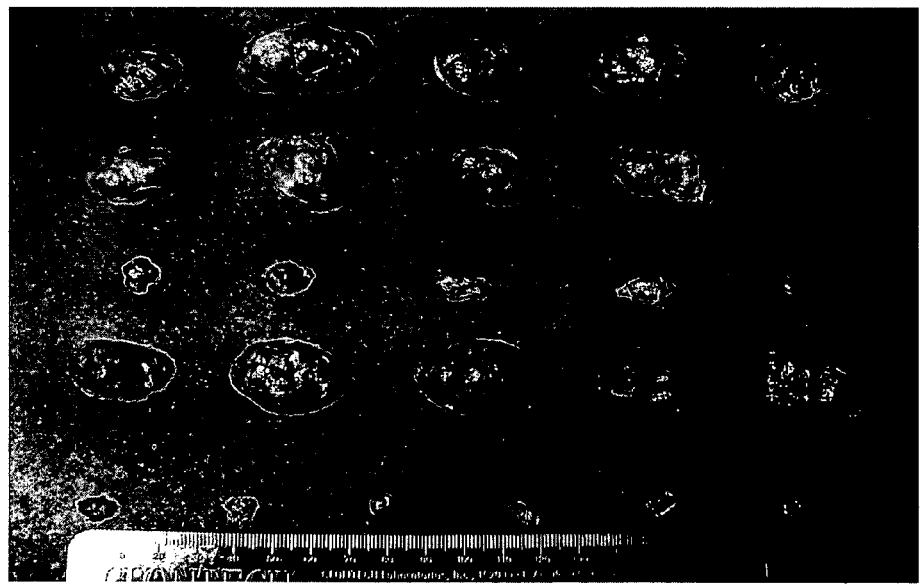
FIG. 10B shows excised tumors from treated mice, from top-to-bottom, the figure presents tumors excised from mice treated with: Lane No. 1: PBS solution (average tumor mass: 3.16±0.65 g; N=5); Lane No. 2: 100 μg of gelonin (2.62±0.53 g; N=4); Lane No.3: 110 μg of TAT-Gel conjugates (0.33±0.12 g; N=5); Lane No. 4: 110 μg TAT-Gel conjugates+20 μg heparin (2.86±0.57 g; N=5); and Lane No. 5: 110 μg TAT-Gel conjugates+20 μg heparin+60 μg protamine (0.17±0.19 g; N=6). Test compounds were administered by intratumoral injection. Injections were started 3 weeks after tumor cell implantation when tumors reached the size about 100 mm³. Thirty days after initial treatment, the mice were sacrificed and their tumors were excised, weighed, and photographed.

As shown in FIGS. 10A and 10B, tumor growth in the control group (injected with PBS solution) was significant, with tumors continuing to grow gradually over the four-week period of the experiment (FIG. 10A). Four weeks after PBS injection, the average tumor mass in the control group was 3.16±0.65 g (FIG. 10B). Mice treated with gelonin alone did not display tumor regression, since gelonin by itself cannot penetrate tumors. An average tumor weight of 2.63±0.5 g was observed four weeks after treatment in the group administered gelonin alone. The tumor mass in this group was statistically indistinguishable (p<0.05) from that of the control group. This suggests that the slight regression in tumor volume seen in FIG. 10A for the group treated with gelonin alone over the control group was attributable to inconsistency or inaccuracy in measuring tumor volumes. The administration of free TAT and gelonin in another group provided no difference in tumor regression, as an average tumor mass of 2.74±0.68 g (N=4) was observed four-weeks after treatment. On the other hand, mice treated with TAT-Gel conjugates displayed significant tumor regression, with tumor weights reduced to a relatively insignificant value of 0.33±0.12 g. The addition of heparin to the TAT-Gel conjugate solution prior to its injection revealed a complete inhibition of TAT-mediated gelonin uptake and only statistically insignificant tumor regression. Four weeks after this treatment, tumors grew to a mass of 2.86±0.57 g; which was comparable to that seen in the control group and the group administered gelonin alone. The slight tumor regression seen in the group administered heparin and the TAT-Gel conjugate solution over the control groups was likely due to artifact in volume measurements, because mice treated with gelonin alone showed a higher degree of tumor regression than the group administered heparin-inhibited TAT-Gel conjugates. The subsequent administration of protamine to the heparin-inhibited TAT-Gel conjugate group completely reversed inhibition and revived the cytotoxic activity of the TAT-Gel conjugates, as tumor regressed to an insignificant weight of 0.17±0.09 g.

Figure 17A:
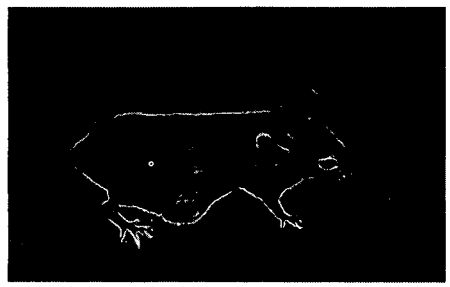
FIGS. 17A and 17B show the gross appearance of subcutaneously implanted tumors after treatment with free gelonin at two weeks (FIG. 17A), and four weeks (FIG. 17B).
Figure 17B:
Figure 17C:
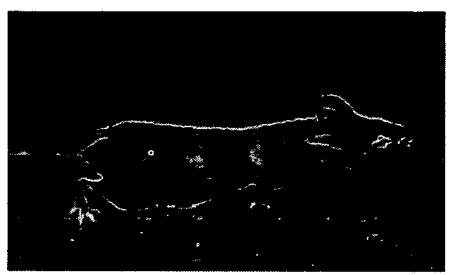
FIGS. 17C and 17D show the gross appearance of subcutaneously implanted tumors after treatment with TAT-Gel conjugates at two weeks (FIG. 17C), and four weeks (FIG. 17D).
Figure 17D:

FIGS. 17A-17D present a representative example of the gross appearance of mice following intratumoral injection of free gelonin or TAT-Gel conjugates. As seen in FIG. 17A, the tumor became evident at about 2 weeks and continued to grow 4 weeks (FIG. 17B) after free gelonin treatment. This indicates that free gelonin was not cytotoxic to the tumor. On the other hand, FIG. 17C shows that tumor regression was obvious two weeks after treatment with TAT-Gel conjugates. This confirms that the TAT based drug delivery compositions of the present invention are able to transduce gelonin into tumor cells. Four weeks after TAT-Gel conjugate treatment (FIG. 17D), tumor mass was largely collapsed into a scabrous tissue plug that later dropped off to reveal scar tissue at the former tumor site.

2. TAT-Gel Conjugate Tumor Penetration

Figure 18A:
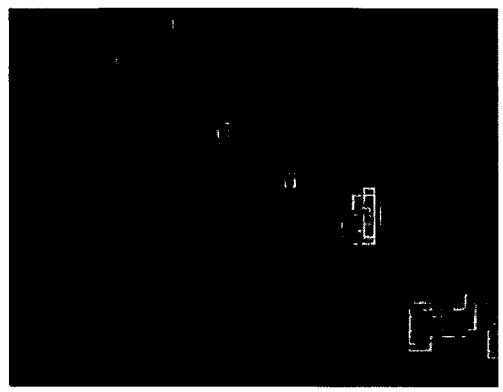
FIGS. 18A and 18B show tumor penetration of rhodamine-labeled TAT-Gel conjugates (FIG. 18A), and free gelonin (FIG. 18B). Tumors were isolated at 10 hrs after injection of the rhodamine-labeled TAT-Gel conjugate or free gelonin and then photographed.
Figure 18B:
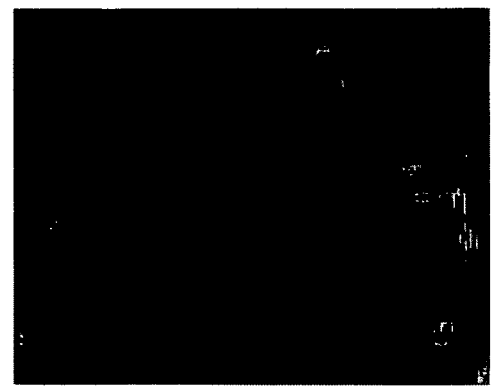

To further confirm that TAT-Gel conjugates penetrate into tumor tissues, rhodamine-labeled gelonin was used in several additional in vivo studies. As shown in FIG. 18A, murine tumor tissues excised from rhodamine-labeled gelonin in TAT-Gel conjugates displayed strong and uniform rhodamine staining. These results clearly demonstrate the successful entry of TAT-Gel conjugates into murine tumor tissues. On the other hand, mice injected with rhodamine labeled gelonin alone displayed virtually no staining or only sporadic weak staining (FIG. 18B). The extremely efficient tumor penetration and widespread drug distribution capabilities of the compositions and methods of the present invention are of great significance to anticancer therapy. As discussed previously, tumor treatments using existing methods of enhancing cellular drug uptake, including the most effective immunoconjugation methods, are hindered by a poor penetration of tumor tissues.

Example 9

Characterization of Heparin-VEGF/C2B8 Conjugates

This example describes experiments to characterize the heparin-VEGF/C2B8 conjugates. In one embodiment, after preparation of the heparin-VEGF/C2B8 conjugates the protein contents are determined using the Bradford protein assay. (M. M. Bradford, Anal. Biochem., 72:248-254 [1976]). The molar ratio between heparin and $VEGF_{121}$ (or C2B8), presumably 1:1 due to the use of end-point attachment for heparin, is confirmed using MALDI-MS and SDS-PAGE analyses.

Example 10

Targeting Functions of Heparin-VEGF/C2B8 Conjugates

The targeting functions of $VEGF_{121}$ and C2B8 is examined using specific cell lines. Results obtained from the heparin-linked conjugates are compared with those obtained from the parent compounds without heparin.

Example 11

Heparin-$VEGF_{121}$ Conjugates

Binding experiments of the heparin-$VEGF_{121}$ conjugates are conducted using the protein kinase receptor Flk-1. Binding to Flk-1 is examined on microtiter plates with wells treated avidin and then coated with biotinylated Flk-1. $VEGF_{121}$ (control) or heparin-$VEGF_{121}$ conjugates are added to the wells at various concentrations. Following incubation, the plates are washed and then contacted with the non-blocking mouse monoclonal anti-$VEGF_{121}$ antibody. The targeting functions of $VEGF_{121}$ is determined by adding horseradish peroxidase (HRP)-labeled goat anti-mouse antibody to the wells and measuring the absorbance at 490 nm using O-phenylenediamine and hydrogen peroxide as the substrates for peroxidase. (See, L. M. Veenendaal et al., Proc. Natl. Acad. Sci. USA, 99:7866-7871 [2002]).

Example 12

Heparin-Anti-CD20 C2B8 Conjugates

In this experiment, Raji human B-cell lymphoma cells and the competitive binding assay described by Newton et al., is used for determining the targeting functions of the heparin-C2B8 conjugate. (See, D. L. Newton et al., Blood, 97(2):528-535 [2002]). Briefly, Raji human B-cell lymphoma cells ($6 \times 10^5$ cells in 1.0 mL PBS buffer containing 1% bovine serum albumin) are placed in tubes, followed by addition of 10 μL of varying concentrations of either the C2B8 antibody or the heparin-C2B8 conjugates. After incubation on ice for 15 min, $^{125}$I-labeled C2B8 (20 ng per assay, $1.5 \times 10^8$ cpm/nmol) is added to the cells and the mixture is incubated on ice for 2 hrs. The amount of the $^{125}$I-antibody bound to the cells is measured using a gamma counter. $^{125}$I-counts between C2B8 and the heparin-C2B8 conjugate are compared to determine the retention of the targeting functions of the conjugate.

Example 13

In vitro Cell Culture Studies

This example describes several experiments to determine affects of the present drug delivery systems in in vitro cell systems. In vitro studies do not require use of the molecular recognition elements of the drug delivery compositions, thus only the drug delivery component, that is the PTD subcomponent and any attached drug(s) are used in these experiments. Unless otherwise noted, conjugate samples to be tested include: (i) doxorubicin alone; (ii) Dox-PR (polyrotaxane); (iii) LMWP-Dox-PR; (iv) LMWP-Dox-PR+heparin; and (v) LMWP-Dox-PR+heparin+protamine; whereas the sample for gelonine include: (i) gelonin alone; (ii) LMWP-Gel; (iii) LMWP-Gel+heparin; and (iv) LMWP-Gel+heparin+protamine.

The cytotoxicity ($IC_{50}$) of the LMWP-linked drug conjugates are analyzed by using the log-phase cytotoxicity assay. For cytotoxicity evaluation, both the CT-26 and Raji cell lines are used. The Raji cells is derived from the Burkitt's lymphoma cell line that is available at American Type Culture Collection (ATCC). These cell lines are maintained in culture in complete medium at 37° C. in a 5% $CO_2$-humidified air incubator. A RPMI 1640 medium supplemented with 10% heat-inactivated fetal bovine serum and 100 units of penicillin/streptomycin are used.

1. Log-Phase Cytotoxicity Assay

To conduct the log-phase cytotoxicity assay, the cell cultures are washed and cells are detached using Trypsin-EDTA. The cells are then resuspended in complete medium at a density of $5 \times 10^4$ cells/mL. Aliquots of suspended cells are dispensed into 96-well microtiter plates, and the cells are allowed to adhere for 24 hrs. The medium is then replaced with medium containing different concentrations of the test compounds, and the cells are incubated for an additional 48 hrs. Relative cell proliferation induced by each test compound are analyzed using the MTT staining assay. (M. G. Rosenblum et al., Cancer Chemother. Pharmacol., 44: 343-348 [1999]).

2. Confocol Microscopy Analysis

Cellular uptake of the test compounds is examined by confocol microscopy using the FITC-labeled drugs. Test compounds are added to cells ($10^4$ CT-26 or Raji cells) cultured in Lab-Tek-chambered cover glasses. After a 1 hr incubation, cells are fixed with 1% paraformaldehyde and then mounted with PBS:glycerol mixture containing anti-fading agent. Confocol laser scanning microscopy is performed on the cells using a Zeiss (Gottingen, Germany) inverted LSM-510 laser scanning microscope equipped with a Plan-Apochromat 63×1.4 N.A. or 40×1.4 N.A. lens. The laser is set to produce 488 (blue) and 543 (yellow) excitation wavelengths for fluorescein and rhodamine. Z-series is taken of a 1 to 2 micron optical section at 2 mm intervals.

3. Flow Cytometry Analysis of Cell Uptake

Cells (CT-26 or CA46) are seeded at a density of 106 cells per well in 6-well plates in 1.5 ml culture medium. After a 24 hr incubation, FITC-labeled test compounds are added to the wells and cells are incubated for 1 hr. Following washing, these cells are fixed with 1% paraformaldehyde. Analysis is carried out on a Beckton Dickinson (San Jose, Calif.) FACS-caliber flow cytometer equipped with a 488 nm air-cooled argon laser. The filter settings for emission is at 530/30 nm bandpass (FL1) and 585/42 nm bandpass (FL2) for FITC and rhodamine, respectively. The fluorescence of 10,000 vital cells are acquired and data is visualized in logarithmic mode.

4. Heparin/Protamine-Dependent Cytotoxicity

A slightly modified colorimetric assay using MTT is used to assess the effects of heparin and protamine on the cytotoxicity of test compounds on the exponential growing cells. Briefly, cells are seeded at $10^4$ cells/well in 96-well plates 24 hrs before incubation with the drugs (or their conjugates) in the presence of heparin. Thirty minutes after addition of these test compounds, protamine are added. The cells are incubated for another 2 days, and the relative cell proliferation are analyzed using the MTT staining method described previously.

5. Analysis of Apoptotic Cell Death

Annexin V-FITC (MBL, Naka-ku, Nagaya, Japan) is used to evaluate the number of cells that undergo apoptosis. (C. Vitali et al., Proc. Natl. Acad. Sci. USA, 98 (10):5764-576 [2001]). Briefly, aliquots of cells exposed to the test samples are washed, re-suspended in the binding buffer (10 mM Hepes solution containing 140 mM NaCl and 2.5 mM $CaCl_2$ at pH 7.4), and then mixed with 1 μL of Annexin V-PITC/$10^5$ cells and 1 μL of propidium iodide (PI) at a final concentration of 2 μg/mL. After 5 min incubation in the dark at room temperature, cells are analyzed by using flow cytometry. The percentage of Annexin V-positive cells is calculated based on the PI-negative cell population. The criteria used for measuring cell death is based on changes in the light-scattering properties (forward side scattering and side scattering) of dead cells due to cell shrinkage and increased granularity. For estimation of apoptotic DNA fragmentation, the Boehringer (Mannheim, Germany) ELISA Cell-Death Detection Kit is used by following the procedures described by the manufacturer. (C. Vitali et al., supra). After treatment with different stimuli, cells ($15 \times 10^3$) are harvested at the 18th and 40th hr and analyzed. The principle of this test is based on detection of mono- and oligo-nucleosomes in the cytoplasmic fractions of the cell lysate by using biotinylated anti-histon- and peroxidase-coupled anti-DNA antibodies. The enrichment of mono- and oligo-nucleosomes released into the cytoplasm is calculated by comparing the absorbance of treated and untreated cells.

Apoptosis is monitored by microscopic observation using the TUNEL method. (K. A. Reed and J. M. Gallo et al., Cancer Res., 62:1382-1387 [2002]). Briefly, cells are treated with the test samples for 0, 8, and 24 hr. After trypsin digestion, cells are combined with the dead ones floating in the medium and then fixed with 7% formalin. The fixed cells are placed on slides prepared according to the instructions by the manufacturer, and then analyzed by using a fluorescent microscopy. The cells with a bright blue fluorescence are counted as apoptotic cells.

6. MDR Effects towards LMWP-Dox-PR

Previous studies have shown that the membrane-translocating function of TAT can offset the MDR effects towards small drugs such as doxorubicin. The polyrotaxane-based small drug delivery systems described herein enhance the anti-MDR effects towards small drugs. The resistant A2780/AD cell line is employed in these studies. All of the above-mentioned experiments are carried out on samples including: (i) doxorubicin alone; (ii) Dox-PR; and (iii) LMWP-Dox-PR; as well as in the presence or absence of the P-glycoprotein inhibitor. Results among the experimental groups are then compared.

Example 14

In vivo Studies

The following example describes various contemplated in vivo experiments. These experiments establish the feasibility, efficacy, toxicity, and pharmacokinetics of the proposed drug delivery compositions and methods. The in vivo experiments are divided into two categories by tumor type: solid tumors and diffuse tumors. Unless otherwise noted, each experiment includes 6-9 mice to provide statistically meaningful results for analysis. In some embodiments, for the solid tumor in vivo studies, $VEGF_{121}$ is used as the molecular recognition element.

1. Solid Tumors

A. LMWP-Dox-PR Drug Delivery Systems

In some embodiments, the toxicity of the drug and drug conjugates are assessed by examining both the maximum tolerated bolus i.v. dose and the systemic toxicity on viability of bone marrow haematopoietic precursor cells and splenocytes.

To conduct maximum tolerated bolus intravenous dose (MTBD) studies, free doxorubicin, Dox-PR, and LMWP-Dox-PR are prepared by dissolving them in HBSS buffer and tested. The 4-6 week-old BALB/c mice are injected with increasing doses (e.g., 1, 5, 10, 20, 50, and 100 mg) of the test compounds via the tail vein and observed for 24 hrs post the injection. Each experimental group consists of 3 mice for each dose of the test compound. The mice are anesthetized and sacrificed by intraperitoneal injection of the ketamine cocktail (44 mg Ketamine; 2.5 mg Xylazine; 0.75 mg acepromazine in PBS per kg of body weight). The livers of the mice are observed under a dissecting microscope for signs of toxicity, according to an established protocol. (O. L. Padilla De Jesus et al., Bioconj. Chem., 13: 453-461 [2002]). The maximum tolerated dose are represented as mg of doxorubicin or equivalent (in the PR-conjugate) per kg of weight. (T. Minko et al., Pharm. Res., 17: 505-514 [2000]). A total number of 54 mice (18 mice for each of the 3 test compounds) are used.

In the contemplated systemic toxicity studies the difference in toxicity between doxorubicin and Dox-PR conjugates is compared by injecting these test compounds into the BALB/c mice. Following injection, haematopoietic precursors in bone marrow of the mice are examined using the colony-forming unit-spleen assay. (B. Rhihoba et al., Biomaterials, 10(5): 335-342 [1989]). In additional embodiments, the inhibition of [$^3$H] thymidine incorporation by mouse splenocytes and human peripheral blood lymphocytes is also determined. (Rhihoba et al., supra). A total of 14 mice, 7 for each of the two test compounds, are used in these studies.

B. Efficacy on Tumor Regression

The efficacy of the LMWP-Dox-PR conjugates is examined by monitoring the tumor regression in the allograft tumor-bearing BALB/c mouse model. Four-six week old BALB/c mice are injected subcutaneously in the middle of the left flank with 100 µL of a single-cell suspension containing $10^6$ CT-26 cells. Tumors are measured with vernier calipers, and volumes are calculated according to the formula of: volume=$0.52 \times W^2 \times L$, where W and L represent the width and length respectively. Treatment of the tumors starts 2-3 weeks after tumor implantation when their sizes reach about 100-150 mm$^3$. Test compounds include: (i) PBS solution (control); (ii) LMWP-Dox-PR (at the above determined maximum tolerated dose); (iii) LMWP-Dox-PR+ heparin; and (iv) LMWP-Dox-PR/heparin-$VEGF_{121}$ complex. Each animal group contains 10 mice. Nine drug treatments are administered intravenously to each of the tumor-bearing mice. For experimental groups (iii) and (iv), protamine (60 µg, 3:1 w/w ratio to heparin dose) is injected intravenously 30 min after the drug treatment. Tumor volume is monitored once every 3-4 days after sample injections. Changes in body weight and the survival time for each mouse is recorded following an established protocol. (A. Evrard et al., Int. J. Cancer, 80:465-470 [1999]. At the end of the observation period (8-9 weeks after the treatment), the mice are sacrificed and autopsied; their tumors are removed, weighed, and fixed with formalin. Mean tumor weight and standard deviation is presented for each group. Gross morphology of representative tumors from each group is prepared using hematoxylin and eosin staining. A total of 40 mice, 10 for each of the 4 test compounds, are used.

C. Assessment of EPR Effects

The EPR effects of the PR-based doxorubicin drug delivery compositions are assessed by the distribution and retention of doxorubicin in the tumor according to established procedures. (T. Minko et al., Pharm. Res., 17:505-514 [2000]). Two test compounds; doxorubicin and LMWP-Dox-PR both containing $^{13}$C-labeled doxorubicin, are injected intraperitoneally to the CT-26 bearing BALB/c mice (prepared as described previous). At 1, 4, 6, 24, 48, 72 hr time intervals after drug administration, animals are sacrificed and their organs and tumors dissected. Radioactivity in the organs and tumor of each mouse is measured using the β-emitting scintillation counter and presented as the percent of dose per gram of the organ or tumor. Three mice are used for each time interval, and a total of 36 mice (18 for each test compound) are used.

D. Assessment of MDR Effects

Chemoresistant A2780 cell lines are produced by chronic exposure of the cell lines to doxorubicin. In brief, sensitive A2780 cells are grown in 25 cm$^2$ cell culture treated flasks in parallel. These cells are then exposed to two drug samples (doxorubicin and LMWP-Dox-PR) for 24 hr. After incubation, the drug(s) are removed, the cells placed in fresh medium, and then promptly illuminated for 18-30 min (6.0-3.1 mW cm$^{-2}$) and incubated under cell culture conditions for 72-96 hr. After this initial recovery period, $2 \times 10^6$ cells are seeded in 25 cm$^2$ flasks and incubated under cell culture conditions for 48-72 hr to ensure an adequate time for recovery. Cells are harvested for characterization and $2 \times 10^6$ cells are seeded in 25 cm$^2$ flasks to continue the chronic exposure experiment. During the first two months of the experiment, a second recovery is employed. To achieve a more rigorous treatment in subsequent drug exposures, the second recovery period is abandoned after the ninth exposure. A total of 14 exposures to each drug are performed over a period of 78 days. Both the sensitive A2780 and resistant A2780/AD cells are utilized as negative and positive controls, respectively. (M. Mazel et al., Anticancer Drugs, 12:107-116 [2001]).

E. Tumor Regression in MDR Model

MDR-induced mouse model are prepared by subcutaneous injection of A2780/AD cells using the same protocol discussed above except that BALB/c nude mouse are used for this study. Each experimental group consists of 10 mice for the tumor regression study. The same procedures for tumor regression studies discussed above are followed to examine the MDR effects towards the use of the LMWP-Dox-PR conjugate. Parallel studies are performed using free doxorubicin on the A2780/AD-bearing control mice. A total of 20 mice (10 for doxorubicin and 10 for LMWP-Dox-PR) are used.

F. LMWP-Gel System

Due to the absence of EPR or MDR effects for gelonin (because of its lack of cellular uptake), in vivo studies are limited to only examination of the efficacy of the LMWP-Gel/Heparin-VEGF$_{121}$ approach.

To examine the specific localization of the LMWP-Gel conjugates, three CT-26 tumor-bearing mice (prepared using the same procedures described above) are injected intravenously with one of the two test compounds: (i) LMWP-Gel/Heparin (without VEGF$_{121}$ and containing 100 mg gelonin equivalence; used as the control) or (ii) LMWP-Gel/Heparin-VEGF$_{121}$ (contains 100 mg gelonin and 50 mg VEGF$_{121}$ equivalence). Thirty minutes after injection, the mice are sacrificed, exsanguinated, and all major tissues are snap-frozen. Sections of the tissues are cut and double stained with pan-endothelial marker MECA-32, followed by detection of the specific localization of the test compounds using the rabbit anti-gelonin antibody. The MECA-32 rat IgG is visualized using goat anti-rat IgG conjugated to rhodamine (red fluorescence). The anti-gelonin antibody is detected using the goat anti-rabbit IgG conjugated to Cy-3 (green fluorescence). Colocalization of both markers is indicated by a yellowish color. In addition, to determine the percentage of vessels with the localized test compound, the number of vessels stained with MECA-32 (red), gelonin (green), or both (yellow) are counted from the specimen. Two slides from each mouse are analyzed and the average percentage of positive vessels calculated. (R. M. Shaheen et al., Cancer Res., 59:5412-5416 [1999]).

G. Maximum Tolerated Dose

To determine the maximum tolerated dose of the LMWP-Gel conjugates that can be use for subsequent tumor regression studies, the same experiments described above for the LMWP-Dox conjugates are carried out in BALB/c mice. Two test compounds, gelonin and LMWP-Gel conjugates, are included in the study. Three mice are used for each dose study for a total of 6 different dose for each test compound as described above. Thirty-six mice are used for the entire study. The maximum tolerated dose is determined as mg of gelonin or equivalent (in the LMWP-Gel conjugate) per kg of weight using an established protocol. (T. Minko et al., Pharm. Res., 17:505-514 [2000]).

H. Tumor Regression in Allograft Model

The same experimental procedures described above are followed to prepare the CT-26 tumor-bearing mice and to examine the efficacy of the LMWP-Gel conjugates on tumor regression. Test compounds include: (i) PBS solution (control); (ii) LMWP-Gel conjugates; (iii) LMWP-Gel conjugates+heparin (100 mg gelonin equivalence); and (iv) LMWP-Gel/Heparin-VEGF$_{121}$ conjugates (100 mg gelonin and 50 µg VEGF$_{121}$ equivalence). For experimental groups (iii) and (iv), protamine (60 µg, 3:1 w/w of the injected heparin dose) are injected intravenously 30 min after the drug treatment. Each experimental group includes 10 mice. Tumor volume, body weight, survival time, and gross tumor morphology studies are conducted as described above.

As described above, vascular targeting could have a dual antitumor therapeutic effect. Thorpe and coworkers (P. E. Thorpe and F. J. Burrows, Breast Cancer Res. Treatment, 36:237-251 [1995]) reported that damage of the vascular endothelial by VEGF-gelonin conjugates resulted in massive tumor cell death. Accordingly, the present invention contemplates that the present LMWP-Gel drug delivery compositions damage tumor cell vasculature in Group (iii) and (iv) mice. Additional studies are conducted on these two test groups. The above (iii) and (iv) test compounds that contain rhodamine-labeled gelonin are injected into the mice, followed by the injection of protamine solution 30 min later. After a 6 hr rest period, mice are sacrificed and their tumors collected. Distribution of fluorescent rhodamine is examined using the confocol microscopy. Results obtained from this study provide information about of the dual therapeutic affects produced by certain embodiments of the present delivery compositions comprising vascular molecular recognition elements.

I. Histology Analysis

To confirm endothelial cell destruction and apoptosis in the tumor caused by LMWP-Gel conjugates, histology studies are performed on CT-26 tumor-bearing mice following drug treatment. Two test compounds, including: (i) LMWP-Gel; and (ii) LMWP-Gel/Heparin-VEGF$_{121}$ conjugates+protamine (both contain 100 mg gelonin equivalence) are injected directly into the tumors. After a 48 hr waiting period, mice are sacrifice and their organs and tumors are removed and fixed in buffered formalin. Paraffin sections are prepared, stained with hematoxylin and eosin, and examined by light microscopy. (L.M. Veenendaal et aL, Proc. Natl. Acad. Sci. USA, 99:7866-7871 [2002]). Further, apoptosis assays are performed on the dissected tumor tissues. Apoptosis among cancer cells in the tumor specimens is detected by a DNA nick end-labeling method using an in situ apoptosis detection kit according to procedures described by Ma et al. (A. J. Reed and J. M. Gallo, Cancer Res., 62: 1382-1387 [2002]). The sections are counterstained with hematoxylin. The apoptotic cells are labeled blue. Apoptotic cells are counted under a light microscope (×200 magnification) in five random fields, and the apoptosis index is calculated as a percentage of all cancer cells in these fields. (A. J. Reed and J. M. Gallo, infra).

J. Pharmacokinetics and Biodistribution

Pharmacokinetics and biodistribution studies of both doxorubicin and gelonin conjugates are carried out in solid tumor models. Because in real-time application of the proposed delivery systems, only LMWP-drug/Heparin-VEGF$_{121}$ and LMWP-drug conjugates are exposed to the subject's blood stream, for simplicity, only three test compounds for each drug is included in the following pharmacokinetics and biodistribution studies. Three test compounds for doxorubicin-related studies include: (i) doxorubicin (control); (ii) LMWP-Dox-PR conjugates; and (iii) LMWP-Dox-PR/Heparin-VEGF$_{121}$ conjugates; whereas compounds for gelonin studies include: (i) gelonin (control); (ii) LMWP-Gel conjugates; and (iii) LMWP-Gel/Heparin-VEGF$_{121}$ conjugates.

In some embodiments, pharmacokinetic studies are conducted using the CT-26 tumor-bearing BALB/c mice prepared according to the procedures described above. Subsequently, the mice are injected with each of the aforementioned test compounds that contain $^{13}$C-labeled doxorubicin or $^{125}$I-labeled gelonin (0.5 µCi each). Three mice in each group are sacrificed by cervical dislocation at 15, 30, 60, 90, 120, 240 min, and 12, 24, 48 and 72 hr intervals after drug injection. Blood samples are removed from the chest cavity, weighed, and measured for radioactivity using a β-scintillation counter for doxorubicin- and γ counter for gelonin-contained compounds. The blood samples are then centrifuged and the supernatant decanted and counted for estimating the amount of plasma-associated radiolabels. The ratio of the peak to that of the internal standard is used as the assay parameter. Pharmacokinetic parameters are calculated by using the KINFT (M. L.

Kaltenbach and R. Vistelle, Anticancer Res., 14(6A):2375-2377 [1994]) nonlinear least-squares computer program by fitting the plasma radioactivity data to a biexponential equation (M. G. Rosenblum et al., Clin. Cancer Res., 5: 865-874 [1999]):

$$A(t) = A_{1e}^{-k_1^1 t} + A_{2e}^{-k_2 t} \quad \text{(Equation 1)}$$

where A(t)=% ID/mL plasma and ID=injected dose. The area under the plasma concentration-time curve (AUC), the steady-state volume of distribution (Vss), total plasma clearance (Cl), and the mean residence time (MRT) is calculated from $A_1$, $A_2$, $k_1$, $k_2$, and the body weight (kg) of the rat as described by Gibaldi and Perrier (M. Gibaldi and D. Perrier, Pharmacokinetics, Marcel Dekker, Inc., New York [1982]). The organ permeability-surface area (PS) product is calculated as:

$$PS = [V_d - V_0] C_{p(60\ min)} / AUC_{(0-60\ min)} \quad \text{(Equation 2)}$$

where $CP_{(60\ min)}$ is the terminal plasma concentration (dpm/mL) at 60 min after injection, $V_d$ is the tissue volume of distribution determined from the ratio of disintegrations per minute per gram of the tissue to $C_{p(60\ min)}$, and $V_0$ is the organ plasma volume. The organ delivery of the samples is determined as:

$$\%\ ID/g = PS \times AUC_{(0-60\ min)} \quad \text{(Equation 3)}$$

where % ID/g is the percent injected dose taken up by per gram of organ.

The plasma metabolic stability of the LMWP-Gel/Heparin-VEGF$_{121}$ complex is also determined by trichloroacetic acid (TCA) precipitation of 50 µL aliquots of the plasma sample removed 60 min following intravenous injection of 5 µCi of $^{125}$I-Gelonin-LMWP/Heparin-VEGF$_{121}$ and unlabeled complex.

In still other embodiments, biodistribution studies are conducted in conjunction with the pharmacokinetics studies described in the previous section. Briefly, after completion of blood sampling for the pharmacokinetic studies tumors and normal tissues are removed, weighed, and measured for radioactivity using a β-scintillation and a γ counter for doxorubicin and gelonin-contained samples, respectively. The amount of radioactivity distributed to the tumor or various organs is expressed as the percentage of the injected drug dose per gram of the tissues. The data is expressed as ratios to the concurrent blood levels using a previously established protocol. (See, M. G. Rosenblum et al., Clin. Cancer Res., 5: 865-874 [1999]). To obtain further information of the MDR effects, the same sets of experiments are conducted on doxorubicin and its related conjugates against resistant AD2780/AD tumor-bearing mice. In preferred embodiments, for the entire pharmacokinetic/biodistribution studies, 3 mice are involved in measurements of each of the 10 time intervals, and a total of 180 BALB/c mice are used for the three test compounds involved in each of the test drugs (e.g., doxorubicin and gelonin).

2. Diffuse Tumors

In some contemplated diffuse tumor (e.g., B-Cell lymphoma) studies, anti-CD20 antibody C2B8 serves as the sole molecular recognition element in the targeting component of the present drug delivery systems.

A. LMWP-Dox-PR Conjugate System Feasibility Studies

Since studies of the polyrotaxane-based doxorubicin delivery approach require intravenous administration of the drug conjugates, it is important to examine the blood retention situation before assessing the therapeutic efficacy of this system in treating diffuse tumor. In preferred embodiments, studies to examine the blood retention time provide two test compounds: (i) LMWP-Dox-PR conjugates; and (ii) LMWP-Dox-PR/Heparin-C2B8 conjugates. The test compounds are $^{13}$C-labeled at doxorubicin and injected (100 µL) via the tail vein of BALB/c female mice (4-6-week old). Each experimental group includes 3 mice. At time intervals of 3, 10, 30, 60, and 90 min post the injection, 50 µL blood samples are collected from the orbital sinus of each anesthetized mouse using a heparinized capillary. Radioactivity (cpm) in the blood samples is determined using a β-scintillation counter. The blood elimination rate of the test compounds is calculated using a log-linear regression of cpm/mL versus time. (See, O. L. Padilla De Jesus et al., Bioconj. Chem., 13: 453-461 [2002]).

B. Tumor Regression in Xenograft Model

In some embodiments, tumor regression studies for LMWP-Dox-PR conjugates are conducted in the manner described above for solid tumors, except that 6-week-old athymic nude mice with severe combined immunodeficiency (SCID) are used. A 100 µL suspension containing $1.8 \times 10^7$ of B-cell lymphoma Raji cells is implanted into each mouse by subcutaneous injection. Two days after tumor implantation, the mice are treated with the test compounds by tail vein injection every day for 4 consecutive days. Four test compounds, including: (i) PBS solution (control); (ii) LMWP-Dox-PR conjugates; (iii) LMWP-Dox-PR conjugates+heparin; and (iv) LMWP-Dox-PR/Heparin-Anti-CD20 complex are used. For the Group (iii) and (iv) animals, protamine (60 pg, 3:1 w/w ratio to the heparin dose) is injected 12 hr after drug injection. The appearance of tumors is monitored daily for 30 days after the first drug treatment. All measurements described above in the solid tumor regression xenografts model are carried out as described above.

C. LMWP-Gel Drug Delivery Systems

The same procedures described previously is employed in preparing the CA46 lymphoma-bearing athymic nude (SCID) mice and testing the efficacy in tumor regression by the LMWP-Gel system. The four test compounds include: (i) PBS solution (control); (ii) LMWP-Gel conjugates; (iii) LMWP-Gel conjugates+heparin (100 µg gelonin equivalence); and (iv) LMWP-Gel/Heparin-Anti-CD20 complex (100 µg gelonin and 50 µg anti-CD20 equivalence). For the Group (iii) and (iv) animals, protamine (60 µg, 3:1 w/w ratio to heparin dose) is injected 12 hr after complex injection. Each experimental group includes 6-9 mice. Tumor volume, body weight, and survival time of each mouse, as well as the flow cytometry analysis is performed according to the procedures described previously.

D. Pharmacokinetics and Biodistribution

Similar pharmacokinetics and biodistribution studies as described previously in regard to solid tumor studies are conducted for the diffuse tumor model. For the same reasons described above, the three test compounds selected for studying doxorubicin-related conjugates are: (i) doxorubicin (control); (ii) LMWP-Dox-PR conjugates; and (iii) LMWP-Dox-PR/Heparin-C2B8 conjugates; whereas for gelonin the test compounds are: (i) gelonin (control); (ii) LMWP-Gel conjugates; and (iii) LMWP-Gel/Heparin-C2B8 conjugates.

E. Pharmacokinetics

The same procedures as described previously are employed to prepare B-cell lymphoma Raji-bearing athymic nude (SCID) mice. Each experimental group includes 3 mice for each observation. To these mice, test compounds labeled with either $^{13}$C or $^{125}$I at the drug moiety are administered (at a dose of 0.5 µCi per mouse). All pharmacokinetic parameters are determined as described above and as according to a well established protocol. (M. C. Chan and R. M. Murphy, Cancer Immunol. Immunother., 47:321-329 [1999]).

F. Tissue Distribution

Similar to studies in the solid tumor models described above, biodistribution studies are conducted in conjunction with pharmacokinetics studies described in the previous section on the B-cell lymphoma Raji-bearing athymic nude (SCID) mice. At each time period, after completion of blood sampling for the pharmacokinetic study, tumors and normal tissues are removed, weighed, and measured for radioactivity using a β-scintillation counter and γ counter for doxorubicin and gelonin treated sample, respectively. Organs from the sacrificed animals including the lung, spleen, thymus, bone marrow, and pancreas, as well as with their surrounding connective and lymph tissues, are removed. Radioactivity in these organs/tissues is determined by using a β-scintillation counter and y counter for doxorubicin samples and gelonin samples, respectively. The results are expressed as the percentage of the injected dose per gram of tissue (% ID/g) using a well-established protocol. (D. J. Buchsbaum et al., Cancer Res., 52: 6476-6481 [1992]).

Example 15

Preparation of TAT/Dopamine-Coated MION

In preferred embodiments, the TAT/dopamine-coated MION conjugates are prepared by co-coating the MION with TAT- and dopamine-linked dextran polymers, and then cross-linking these two polymers as described below.

1. TAT-Dextran Polymer

Figure 23:
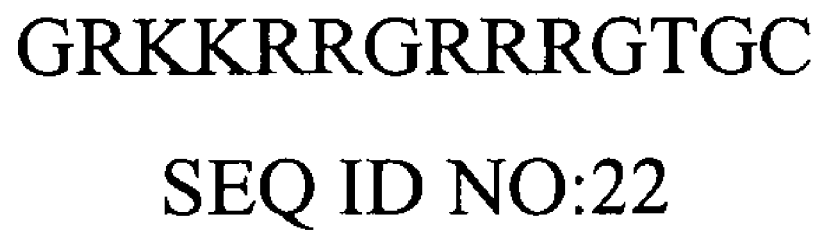

Dextran-$NH_2$ is synthesized by reacting dextran-100 with epichlorohydrin and ammonia, using the protocol described in U.S. Pat. No. 5,262,176 (incorporated herein by reference in its entirety). The Dextran-$NH_2$ is then be activated with N-succinimidyl-3-(2-pyridyldithio)propionate (SPDP) in sodium acetate buffer (pH 7.4) for 3 hr, according to the procedures described in J. F. Liang et al., J. Pharm. Sci., 89:664-673 (2000). TAT is synthesized using standard synthetic peptide chemistries contains the specific amino acid sequence GRKKRRGRRRGTGC (SEQ ID NO:22) (FIG. 23). It is added to the SPDP-activated dextran, followed by stirring the mixture at room temperature for 3 hrs. The final dextran-TAT product is purified using a Sephadex G-25 column.

2. Dopamine-Dextran Polymer

To achieve a dextran coating containing hydrolyzable dopamine, dopamine is linked to dextran-100 using the cyanogen bromide (CNBr) activation method described by of Kim et al. (D. S. Kim et al., Drug Dev. nd. Pharm., 27:97-101 [2001]). Ample evidence has been presented in the literature (D. S. Kim, supra; V. C. Yang and C. L. Teng, An immobilized protamine system for removing heparin in extracorporeal blood circulation. In: Biomimetic Polymers (C. Gebelein, ed.), pp. 175-190 [1990]; and J. Porath and R. Axen, Immobilization of enzymes to agar, agarose, and sephadex supports. In: Methods in Enzymology (K. Mosback, ed.) Vol. 44, pp. 19-45, Academic Press, NY, [1976]) to indicate that compounds immobilized by using this CNBr method can be slowly detached from the support material by a kinetically controlled hydrolysis process.

It should be pointed out that the kinetics of dopamine release can be regulated by adjusting the dopamine loading on the dextran polymer. Furthermore, more rapid or slower release kinetics can also be achieved by using linkages that are more (e.g., anhydride bonds) or less (e.g., ester bonds) susceptible to hydrolysis. (V. C. Yang and C. L. Teng, supra).

3. TAT/Dopamine-Coated MION

The protocol developed described in U.S. Pat. No. 5,262,176 (incorporated herein by reference in its entirety) is followed to prepare TAT/dopamine co-coated MION conjugates. Briefly, 125 mL of a solution containing 450 mg of the above two modified dextran-derivatives (at a TAT/dopamine weight ratio of 1:20) and 31.56 mg (117 nM) of ferric chloride hexahydrate is cooled to 4° C. A freshly prepared (i.e., within 15-30 min) solution containing 12.6 mg (63 nM) of ferrous chloride tetrahydrate dissolved in 4.3 mL water is then added to this cooled mixture. Under continuous stirring, the solution is neutralized by a drop-wise addition of 4.5 mL of cold 28-30% $NH_4OH$ solution. The greenish suspension is then stirred and heated to 75° C. over a period of 1.5 hours. The residuals are removed by ultrafiltration using a hollow fiber cartridge with a MW cutoff of 300 Da. The colloidal product is then concentrated by ultrafiltration using a membrane with a MW cutoff of 30 kDa. The colloidal MION particles should yield a single peak on a Sepharose-2B column, with a particle size of 10-20 nm and a MW of 600-900 kDa. Since each MION particle is shown to contain more than 25 dextran molecules (See, M. Harisinghani et al., AJR, 172:1347-1351 [1999]), and since the iron:dextran mole ratio in each particle is about 80: 1, each TAT/dopamine-MION contains about 5 to 6 TAT molecules and a dopamine loading of approximately 62 mg/mg iron.

Example 16

Preparation of Tat/Peroxidase-Coated MION Conjugates

Since peroxidase is an enzyme that may not be stable under the high temperature, TAT/peroxidase-coated MION conjugates are prepared slightly differently than described above by directly reacting the above TAT-dextran-$NH_2$ mixture with SPDP-activated peroxidase, according to the procedures described by J. F. Liang et al., J. Pharm. Sci., 89:664-673 [2000]).

Example 17

Characterization of the TAT/Drug-Coated MION Conjugates

The final TAT/drug-coated MION products are characterized prior to use for content of each individual component. Briefly, samples of the TAT/dopamine-coated MION conjugates are completely hydrolyzed under highly basic conditions. Based on the structural similarity of the TAT peptide with the low molecular weight protamine (LMWP) peptide described in L. C. Chang et al., the TAT content in these samples are measured using the same HPLC method for LMWP. (L. C. Chang et al., AAPS Pharmsci., 3(2), article 17 [2001]). Dopamine content in these samples is determined using the HPLC assay of Sagar and Smyth (K. A. Sagar and M. R. Smyth, J. Pharm. Biomed. Anal., 22:613-624 [2000]), whereas iron content is measured by the method described by Peterson et al. (C. M. Peterson et al., Blood, 46:583-590 [1975]). Intact TAT/peroxidase-MION samples are used to determine peroxidase activity, using a modified procedure developed by Yang (H. Bernstein et al., Biotechnol. Bioeng., 30:197-207 [1987]) for assaying the activity of immobilized enzymes. The MION samples are then be hydrolyzed and assayed for TAT and iron contents.

Example 18

In vitro Studies

Certain compositions of the present invention provide a chronic release of dopamine in the brain. In order to assess and regulate the amount of dosing and daily dopamine release for the in vivo studies, experiments are conducted to determine the kinetics of drug release from MION in vitro. The MION product prepared above are suspended in the physiological buffered saline (PBS) solution, and the suspension is incubated at 37° C. with mild agitation. At various time points, samples are withdrawn, centrifuged, and dopamine contents in the supernatant is analyzed using the method described by K. A. Sagar and M. R. Smyth, supra. Iron contents in the supernatant is determined (See, C. M. Peterson et al., Blood, 46:583-590 [1975]) to obtain data on the degradation rate of MION. This study is continued for 7 days. The period of time contemplated for the in vivo studies of the dopamine-MION described herein.

Example 19

In vivo Studies

1. Dopamine

Responses to brain dopamine is assessed by monitoring the neurobehavioral changes in a PD rat model. To correlate results with extracellular dopamine concentrations, an intracerebral microdialysis system is implemented for sample collections and assays. In preferred embodiments, neurobehavioral studies are also conducted.

A. Experimental PD Model

A number of PD animal models had been developed for testing the effects of anti-PD drugs (See e.g., U. Ungerstedt, Acta Physiol. Scand. Suppl., 367:69-93 [1971]; T. Hayakawa et al., Clin. Exp. Pharmacol. Physiol., 26:421-425 [1999]; F. B. Jolicoeur et al., Brain Res. Bull., 26:317-320 [1991]; and R. K. Schwarting et al., Brain Res., 554:46-55 [1991]). Among the PD animal models, the rotational model following unilateral lesion of the substantia nigra with 6-hydroxydopamine (6-OHDA) in rats (U. Ungerstedt, supra) has been most widely used for examining clinical anti-PD drugs, and are used in the present invention.

B. Surgical Procedures

To install the microdialysis unit, Sprague-Dawley rats weighing 250±50 g are anesthetized with Equithesin and a microdialysis probe is implanted into the left striatum (from bregma AP: +0.8 mm; ML: +3.45 mm; DV: −7.0 mm from dura). After implantation, the probe is continuously perfused with the artificial cerebrospinal fluid. The rats are then allowed to recover for 18-24 hrs. At least 2 baseline samples are collected prior to the experiments. Intracerebral microdialysis studies are conducted using the procedures described by Gerin (C. Gerin, Neurosci. Lett., 330:5-15 [2002]).

For 6-OHDA lesion, rats are placed in a stereotaxic frame to facilitate injection. A 30 gauge stainless steel cannula is connected to a microsyringe by PE20 polyethylene tubing filled with freshly made 6-OHDA solution and positioned at 1.6 mm lateral, −5.0 mm posterior and −8.0 mm ventral to the bregma on the left side of the rat at a site near the substantia nigra pars compacta. One minute after cannula placement and 30 min after desipramine treatment, rats are infused with 8 mg of 6-OHDA hydrobromide in 4 µL 0.02% ascorbic acid over 8 min using an infusion pump. The cannula is left in place for 5 min after completing the 6-OHDA infusions and then slowly withdrawn. During surgery and 1 hr thereafter, body temperature is monitored via a rectal thermometer probe and maintained using either a heating pad or radiant heat. To assess the efficacy of the lesion, rats are tested 17 and 24 days later for their response to an apomorphine challenge. (See, T. Hayakawa et al., supra). Rats are injected with S-(+)-apomorphine HCl (0.5 mg/kg i.p.) and observed for 20 min. Only rats that complete a minimum of 100 contralateral rotations in 20 min during both testing sessions are used in the subsequent studies. Significant PD-like neurobehavioral changes should be observed in the rats one month after 6-OHDA injections, and such changes should last for at least up to six months. For further confirmation of PD development in all of the 6-OHDA-treated rats one month after injection, 5 rats are randomly selected and sacrificed to compare the tyrosine hydroxylase (TH) immunocytochemistry (as described herein) in the removed brains with those of the control rats receiving no 6-OHDA treatment. A detectable decrease in density of TH-immunoreactive nerve terminals in these rats in comparison with the controls would confirm the full development of PD in the entire 6-OHDA treated rat group.

In vivo studies include 4 animal groups: Groups D1 and D2 serve as the controls whereas Groups D3 and D4 function as experimental groups. In Group D1, the rats are surgically handled the same way but receive 4 µL saline containing 0.02% ascorbic acid instead of 6-OHDA. In Group D2, the rats are surgically treated with 6-OHDA. Neither of the control group rats receive any anti-PD drug(s). In Groups D3 and D4, rats are subjected to experiments one month after 6-OHDA treatments. It should be noted that one-month represents the time interval after which stable physiological conditions are expected for the 6-OHDA treated animals. Of the experimental groups, Group D3 rats are tested by treatment with levodopa, whereas Group D4 rats are treated with TAT/dopamine-coated MION conjugates. Twenty rats are included in each animal group to provide sound statistical analysis of data.

C. Experimental Protocol

In preferred embodiments, a modification of experimental setup described by Pulfer and Gallo is followed. (S. K. Pulfer and J. M. Gallo, J. Drug Targeting, 3:215-227 [1998]). Rats are placed ventrally on a platform so that the head is centered between the poles (2 cm in diameter) of the electromagnet. A drug solution containing a dose of 6 mg levodopa (for Group D3) or an equivalence of dopamine of the dopamine-coated MION conjugates (for Group D4) is injected through the tail vein of the rats. Immediately following drug administration, a magnetic field strength of 0.6T is applied to the rats for 30 min. Parameters reflecting neurobehavioral changes of the rats (as described herein) are monitored every 30 min over a period of 3 hrs. Blood samples are collected from the microdialysis port at time intervals in parallel to those in the neurobehavioral studies and measured for dopamine concentrations using the HPLC method described by K. A. Sagar and M. R. Smyth, supra.

In preferred embodiments, dopamine is slowly hydrolyzed from MION in the brain over an extended period. A chronic study is conducted in order to examine the real-time effects and benefits of the present compositions and methods. Measurements of the neurobehavioral changes are conducted once a day for a total period of 7 days. On the 8th day, the same drug and dose are administered again to the respective rats, and the same experiments is repeated for another seven days. On the 15th day, all rats are sacrificed and subject to histology study (as described herein). Data obtained from the two experimental rat groups are compared amongst each other, as well as with those obtained from the two control groups.

D. Neurobehavioral Changes

Several key parameters are monitored to identify neurobehavioral changes in 6-OHDA-treated rats including: rotational tests, catalepsy, and reaching performance.

Rats are placed into automated rotometer bowls for counting turns in the direction ipsilateral and contralateral to the lesion, using the procedures described by J.F. Marshall and U. Ungerstedt, supra. Behavior is recorded after apomorphine injection. The turning bias is used as a measure of lesion size. Two outcomes are expected form the rotational test with regard to the proposed dopamine-MION treatment. One is that the acute dopamine-MION treatment may induce rotation; just as conventional levodopa treatment does. The other outcome is that, if a chronic dopamine release is achieved with our approach, then it may diminish the rotation asymmetry observed after apomorphine administration.

The catalepsy of the rats is measured according to the method by T. Hayakawa et al., supra. Briefly, the forepaw of the rat is placed on a parallel wooden bar (10 cm high, 10 mm in diameter), and the latency time for removal of the forepaw from the bar is recorded. Unilateral 6-OHDA lesions cause unilateral deficits on the catalepsy and reaching performance (see below) tasks, and thus the proposed dopamine-MION treatment should either eliminate or improve the asymmetric behaviors.

The reaching performance of the rats is examined using the procedures described by Metz and Whishaw. (See, G. A. Metz G A and I. Q. Whishaw, Behav. Brain Res., 116:111-122 [2000]). Briefly, each rat is given a shelf filled with pasta, and the reaching performance is calculated as the number of pasta pieces broken in 10-min intervals up to 30 min. The pattern of the pasta pieces broken is recorded for evaluation of the area in which the animals breaks the pasta. Qualitative evaluation of the reaching movement is achieved by using a modified reaching rating scale (U. Ungerstedt, supra) of the Eshkol—Wachman Movement Notation (N. Eshcol and A. Wachman, Movement Notation. Weidenefeld and Nicholson, London, Englan [1958]). The video recordings are inspected frame by frame.

E. Histology Studies

Histology studies are conducted as follows: fourteen days after the experiments, all rats are sacrificed and subjected to general (i.e., other organs) and specific (i.e., brain) histology studies. The rats are deeply anaesthetized and perfused through the heart with a 0.9% NaCl solution and 4% paraformaldehyde. For general study, histology is performed on tissues from liver, spleen, lung, kidneys, spinal cord, heart, pancreas, bladder, and bowel.

For specific histology study, the brain is removed and post-fixed for 14 days. To perform tyrosine hydroxylase (TH) immunohistochemistry, the brain is cut in 50 µm sections on a vibratome. The sections are washed in 1 M phosphate buffer and then incubated with diluted (1:10000) anti-TH monoclonal antiserum (from mouse IgG; Sigma) overnight at room temperature. The treated sections are processed by the ABC method (Vectastain, Burlingame, CA) with antimouse antiserum IgG and horse serum, and reacted with 3,3'-diaminobenzidine tetrahydrochloride (DAB; 0.06%), hydrogen peroxide (0.03%) and nickel solution. Certain sections are processed with either monoclonal antiserum or anti-mouse antiserum (without anti-TH antiserum) and used as controls. The stained sections are mounted on gelatine-coated slides. For histological analysis, the three sections through the mesencephalon with the highest TH-positive cell density in the lesion hemisphere is chosen. On each section, the area of mesencephalic TH-positive cells are subdivided into the medial area extending from the midline to the ventral tegmental area (VTA), the ventral tegmental area, and substantia nigra pars compacta and substantia nigra lateral portion. The number of TH-positive cell bodies in each quadrant on the lesioned and non-lesioned hemisphere are counted and a ratio of lesion versus non-lesion side are calculated.

F. Toxicity/Serologic Studies

Preliminary toxicity evaluation is carried out by monitoring the weight change, food consumption, mortality, morbidity of the animals during the entire study, as well as by autopsy and histology evaluation (as described herein). In addition, blood samples are taken before the start of the animal study and on the last day of the study. The hematocrit, hemoglobin, cell (e.g., erythrocyte) counts, ion (e.g., $Ca^{+2}$) content, albumin, globulin, urea nitrogen, lactate dehydrogenase, and iron in the serum are examined.

2. Peroxidase

Unlike dopamine, there are no symptomatic parameters that directly reflect the effects of brain peroxidase on neuronal protection. For this reason, success of the present compositions in delivering peroxidase directly into the brain is assessed by measuring changes of certain specific chemical parameters (e.g., concentrations of hydroxyl radicals) in the brain after treatment using the same intracerebral microdialysis techniques for sample collections. In addition, neuroprotection by peroxidase is indirectly assessed by monitoring the behavioral changes in peroxidase-treated rats following insult by the 6-OHDA agents.

A. Experimental PD Model

The neurotoxicity of 6-OHDA comes from its oxidation to quinone and $H_2O_2$. The latter is converted to the reactive OH species via a non-Fenton reaction, exerting its insult on neuronal destruction. Since peroxidase acts primarily as a $H_2O_2$ scavenger, an inverse of the 6-OHDA-induced PD model employed previously for the dopamine studies is used to assess the effects of peroxidase on neuroprotection of the treated animals.

B. Surgical Procedures

The same surgical procedures described above for installing the microdialysis system and performing the 6-OHDA lesions are followed.

C. Experimental Procedures

The same experimental setup as described above is followed. In vivo studies include 4 animal groups: Groups P1 and P2 function as controls, and are prepared similarly to those described previously, except that both groups are surgically managed with installation of the intracerebral microdialysis system. Group P3 is tested by treatment of peroxidase, whereas Group P4 is treated with TAT/peroxidase-MION conjugates. Injections of peroxidase (20 mg or equivalence for Group P3 and P4 animals, respectively) start on day 1 and be repeated for 3 days, whereas the 6-OHDA surgery is performed on day 2. Collection of blood samples from the microdialysis port starts on day 3 on every hour for 6 hours; every 6 hours for 66 hours; and then every 12 hours for 96 hours. On the 8th day, animals are allowed to recover for 2-3 weeks; the incubation period expected to observe obvious PD-like neurobehavioral changes induced by the 6-OHDA lesion (see above). On the 22nd and $29^{th}$ days, animals are subject to apomorphine challenge. Rats are then sacrificed and subject to histology study.

D. Parameters Measured

To measure the concentrations of hydroxyl radicals in the brain, samples collected from microdialysis experiments are added to the trapping agent salicylate that reacts with the hydroxyl radicals to generate 2.5- and 2,3-dihydroxybenzoic acid (DHBA). The produced DHBA are assayed using the HPLC method described by Moussaoui et al. (S. Moussaoui et al., Exp. Neurol., 166:235-245 [2000]).

On both the 22nd and 29th days, animals are tested for their response to an apomorphine challenge, using the rotational test described above.

Histology studies are performed on the organs of the sacrificed rats whereas TH-immunocytochemistry studies are performed on the brains of these rats according to the same procedures described above.

3. Dopamine/Peroxidase

It has been speculated that dopamine in the brain can be converted by MAO to produce $H_2O_2$, which subsequently could undergo the Fenton reaction to yield hydroxyl free radicals causing an enhanced oxidative stress. Taking advantage of the current experimental setup for peroxidase in detecting the generation of such radicals (see above), it is of interest to test this hypothesis to examine if delivery of peroxidase to the brain would alleviate free radical generation. To ensure that any generation of free radicals would come solely from dopamine, healthy rats without 6-OHDA treatment (similar to Group P1 control group described above) are employed. An intracerebral microdialysis system is installed to the rat according to the procedures described above. Two animal groups are included in this study; in Group DPI, rats are administered with dopamine (6 mg)-MION (similar to Group D4 above) whereas in Group DP2, rats are administered simultaneously with dopamine (6 mg)-MION and peroxidase (20 mg)-MION. The same procedures as described herein are followed to magnetically deliver the drugs to the brain. Immediately following delivery, blood samples are drawn from the microdialysis port at time intervals of: every hour for 6 hrs; every 6 hrs for 42 hrs; and then every 12 hrs for 48 hrs. Thereafter, the rats are allowed to rest, and on the 7th day, the entire experiment is repeated. Concentrations of the hydroxyl radicals are measured using the procedures described above.

Example 20

Statistical Analyses

In general, statistical analysis are performed using a Statview software package 4.5 (Abacus Concepts, Inc., Calif.). The results are subject to analysis of variance (anova) for repeated measurements across testing sessions. Comparisons of means between groups are performed using unpaired t-tests and follow-up t-tests for within-subject comparison. Unpaired nonparametric data is analyzed with the Mann-Whitney U-tests. For correlation analysis, Fisher's R-to-Z transformation and a z-test are applied to calculate the significance of the correlation coefficients. In all statistical analysis, a P-value of <0.05 is chosen as the significance level. All data is presented as mean±SEM.

All publications and patents mentioned in the above specification are herein incorporated in their entireties by reference. Various modifications and variations of the described compositions and methods of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition, comprising:
   a. a first targeting component, wherein said first targeting component comprises
      i. a molecular recognition element, wherein said molecular recognition element has established cell specificity, wherein said molecular recognition comprises a polypeptide selected from the group consisting of Vascular Endothelial Growth Factor (VEGF) and C2B8, and
      ii. an anionic molecule having net negative charge, wherein said anionic molecule is heparin, wherein said anionic molecule is conjugated with said molecular recognition element; and
   b. a first drug delivery component, wherein said first drug delivery component comprises
      i. a cationic molecule having a net positive charge, wherein said cationic molecule comprises a protein transduction domain, wherein said protein transduction domain comprises a protein selected from the group consisting of TAT protein and Low Molecular Weight Protamine (LMWP) protein, and
      ii. at least one therapeutic agent conjugated with the cationic molecule.

2. The composition of claim 1, wherein said positively charged cationic molecule associates with said negatively charged anionic molecule.

3. The composition of claim 2, said positively charged cationic molecule associates with said negatively charged anionic molecule through electrostatic interaction.

4. The composition of claim 1, wherein said molecular recognition element comprises a peptide signal sequence.

5. The composition of claim 1, wherein said cationic molecule mediates the translocation of said therapeutic agent into a cell.

6. The composition of claim 1, wherein said therapeutic agent comprises a hydrophilic moiety.

7. The composition of claim 1, wherein said at least one therapeutic agent is attached to said cationic molecule.

8. A drug delivery composition, comprising
   a magnetic nanoparticle associated with a positively charged cationic molecule, molecule, at least one therapeutic agent, and a molecular recognition element,
   wherein said molecular recognition comprises a polypeptide selected from the group consisting of VEGF and an anti-CD20 antibody,
   wherein said therapeutic agent comprises a small molecule drug,
   wherein said positively charged cationic molecule comprises at least a portion of a protein transduction domain, wherein said protein transduction domain comprises at least a portion of a protein selected from the group consisting of TAT protein and Low Molecular Weight Protamine (LMWP) protein.

9. The composition of claim 8, wherein said molecule recognition element binds to a biological target.

10. The composition of claim 8, wherein said molecular recognition element comprises a peptide signal sequence.

11. The composition of claim 8, wherein said positively cationic molecule mediates the translocation of said at least one therapeutic agent into a cell.

12. The composition of claim 1, wherein said first targeting component separates from said first drug delivery component upon exposure of said composition to protamine sulfate.

13. The composition of claim 8, wherein said drug is a chemotherapeutic agent.

14. The composition of claim 13, wherein said chemotherapeutic agent is doxorubicin.

15. The composition of claim 1, wherein said therapeutic agent is a chemotherapeutic agent.

16. The composition of claim 15, wherein said chemotherapeutic agent is doxorubicin.

17. The composition of claim 8, wherein said molecular recognition element has cell specificity.

18. The composition of claim 8, wherein said anti-CD20 antibody is C2B8.

* * * * *

SEQUENCE LISTING

<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Cys Asp Cys Arg Gly Asp Cys Phe Cys
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic

<400> SEQUENCE: 2

Cys Asn Gly Arg Cys Val Ser Gly Cys Ala Gly Arg Cys
1               5                   10

```
<210> SEQ ID NO 3
<211> LENGTH: 3
<212> TYPE: PRT
<213> ORGANISM: Artificial Sequence
<220> FEATURE:
<223> OTHER INFORMATION: Synthetic

<400> SEQUENCE: 3

Gly Ser Leu
1

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Met Leu Ser Leu Arg Gly Ser Ile Arg Phe Phe Lys Pro Ala Thr Ala
1               5                   10                  15

Thr Leu

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Pro Pro Lys Lys Lys Ala Lys Val
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Tyr Gly Arg Lys Lys Arg Arg Gln Arg Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Lys Arg Ile His Pro Arg Leu Thr Arg Ser Ile Arg
1               5                   10
```

```
<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Pro Pro Arg Leu Arg Lys Arg Arg Gln Leu Asn Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Orn
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Arg Arg Xaa Arg Arg Thr Ser Lys Leu Met Lys Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Val Ser Arg Arg Arg Arg Arg Gly Gly Arg Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Tyr Gly Arg Lys Lys Arg Arg Gln Arg Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 14

Lys Arg Ile His Pro Arg Leu Thr Arg Ser Ile Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Pro Pro Arg Leu Arg Lys Arg Arg Gln Leu Asn Met
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Orn
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Arg Arg Xaa Arg Arg Thr Ser Lys Leu Met Lys Arg
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Cys Asp Cys Arg Gly Asp Cys Phe Cys
1               5

<210> SEQ ID NO 18
<211> LENGTH: 13
<212> TYPE: PRT
<213> ORGANISM: Artificial Sequence
<220> FEATURE:
<223> OTHER INFORMATION: Synthetic

<400> SEQUENCE: 18

Cys Asn Gly Arg Cys Val Ser Gly Cys Ala Gly Arg Cys
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Synthetic

<400> SEQUENCE: 19

Gly Ser Leu
1
```

```
<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Met Leu Ser Leu Arg Gln Ser Ile Arg Phe Phe Lys Pro Ala Thr Arg
1               5                   10                  15

Thr Leu

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Pro Pro Lys Lys Lys Arg Lys Val
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Gly Arg Lys Lys Arg Arg Gly Arg Arg Arg Gly Thr Gly Cys
1               5                   10
```